United States Patent [19]

Redmond et al.

[11] Patent Number: 5,831,077
[45] Date of Patent: Nov. 3, 1998

[54] GLYCOSYLHYDRAZINES, PREPARATION, IMMOBILIZATION AND REACTIONS OF: GLYCOPROTEIN ANALYSIS AND O-GLYCAN REMOVAL

[76] Inventors: John William Redmond, 39 Stockdale Street, Dickson, ACT 2602; Nicolle Hannah Packer, 9 Yarabah Avenue, Gordon, NSW 2072; Andrew Arthur Gooley, 14 Vimiera Road, Eastwood, NSW 2122; Keith Leslie Williams, 23 Nandi Avenue, Frenchs Forest, NSW 2086; Michael Batley, 2 Calool Road, Beecroft, NSW 2119; Warren Charles Kerr, 10/3 Trafalgar Place, Marsfield, NSW 2122; Anthony Pisano, 39 Robertson Road, Chesterhill, NSW 2162; Helen Joan Tweeddale, 26 Burraneer Avenue, St. Ives, NSW 2075; Catherine Anne Cooper, 23 Lord Street, Mount Colah, NSW 2079, all of Australia

[21] Appl. No.: 656,277

[22] PCT Filed: Dec. 9, 1994

[86] PCT No.: PCT/AU94/00764

§ 371 Date: Sep. 23, 1996

§ 102(e) Date: Sep. 23, 1996

[87] PCT Pub. No.: WO95/15969

PCT Pub. Date: Jun. 15, 1995

[30] Foreign Application Priority Data

Dec. 9, 1993 [AU] Australia .................. PM2890
Sep. 21, 1994 [AU] Australia .................. PM8328

[51] Int. Cl.[6] .................. C07H 1/00; C07H 5/06
[52] U.S. Cl. .................. 536/55.3; 530/395; 536/17.2; 536/17.9; 536/18.2; 536/18.5; 536/18.7; 536/29.1; 536/29.12; 536/53; 536/54; 536/55; 536/124

[58] Field of Search .................. 536/18.5, 18.7, 536/17.2, 29.2, 124, 17.9, 18.2, 29.1, 29.12, 53, 54, 55, 55.3; 530/395

[56] References Cited

U.S. PATENT DOCUMENTS

| 4,021,542 | 5/1977 | Schmidt et al. .................. 424/180 |
| 5,403,927 | 4/1995 | Bendiak .................. 536/124 |
| 5,585,473 | 12/1996 | Bendiak .................. 536/18.7 |

FOREIGN PATENT DOCUMENTS

| 0 462 795 A2 | 12/1991 | European Pat. Off. . |
| 0 462 798 A2 | 12/1991 | European Pat. Off. . |
| 067267 | 5/1979 | Japan . |
| WO 93/24503 | 12/1993 | WIPO . |

OTHER PUBLICATIONS

El–Khadem, Hassan. *Carbohydrate Chemistry: Monosaccharides and Their Oligomers,* Academic Press, pp. 112–122, (1988).

Bendiak et al., *Carbohydrate Research,* vol. 144: 1–12 (1985).

Maćkiewiczowa et al., *Polish Journal of Chemistry,* vol. 55: 2333–2339, (1981).

(List continued on next page.)

*Primary Examiner*—Marian C. Knode
*Assistant Examiner*—Howard C. Lee
*Attorney, Agent, or Firm*—Fish & Richardson PC

[57] ABSTRACT

The present invention consists in methods of preparing sugar derivatives either in isolation or from glycopeptides or glycoproteins. The methods comprise producing sugar hydrazones, sugar pyrazoles, glycosylpyrazones, azoglycan dyes and hydrazoglycan dyes. The present invention also relates to the removal of O-glycans from glycopeptides or glycoproteins, immobilizing reducing sugars onto solid supports and methods to obtain sugars from a glycopeptide or glycoprotein comprising subjecting the glycopeptide or glycoprotein to solid phase Edman degradation followed by separating and characterizing the sugars.

45 Claims, 35 Drawing Sheets

OTHER PUBLICATIONS

JP 02 038 858 A (Nat. Sci Counc. China); 8 Feb. 1990; Abstract.

Barba, et al., *Diisothiocyanatopolystyrene and some of its polymer–analogous transformations.*, Chemical Abstracts, 89(16):130113n, 2,4, 1978.

Gooley, et al., *Glycosylation Sites Identified by Detection of Glycosylated Amino Acids Release from Edman Degradation: The Identification of Xaa–Pro–Xaa–Xaa as a Motif for Thr–O–Glycosylation,* Biochemical and Biophysical Research Communications, 178(3):1194, 1991.

Gooley, et al., *Characterization of a single glycosylated asparagine site on a glycopeptide using solid–phase Edman degradation,* Glycoconjugate Journal, 11:180, 1994.

Haas, et al., *Rates of Reaction of Nitrogen Bases with Sugars. I. Studies of Aldose Oxime, Semicarbazone and Hydrazone Formation,* 84:4910, 1962.

Jezo, et al., *Aminolysis of sucrose. IX. Reactions of sucrose with aqueous hydrazine solutions at elevated temperatures,* 33 Carbohydrates, 66:11145, 11142u, 1967.

Pisano, et al., *Glycosylation sites identified by solid–phase Edman degradation: O–linked glycosylation motifs on human glycophorin A,* Glycobiology, 3(5):429, 1993.

Schmidt, et al., *Synthese von Pyrazol–, Pyrazolo[3,4–d] pyrimidin–und 1H–1,2,4–Triazolgluconucleosiden aus Glucosehydrazonen,* Liebigs Ann. Chem., pp. 2309–2317, 1981.

Strel'tsova, et al., *Synthesis of pyrazole N–glycosides,* 33–Carbohydrates, 119:1147, 95943x, 1993.

Settineri, et al., *Characterization of O–Glycosylation Sites in Recombinant B–Chain of Platelet–derived Growth Factor Expressed in Yeast Using Liquid Secondary Ion Mass Spectrometry, Tandem Mass Spectrometry and Edman Sequence Analysis,* Biomedical and Environmental Mass Spectrometry, 19:665, 1990.

Stroh, et al., *Uber die Reaktionsprodukte des Hydrazins mit Zuckern,* Eingeganen am 7, pp. 1404 1964.

Takasaki, et al., *Hydrazionolysis of Asparagine–Linked Sugar Chains to Produce Free Oligosaccharides,* Methods in Enzymology, 83:263, 1982.

Talbo, et al., *Determination of the covalent structure of an N– and C–terminally blocked glycoprotein from endocuticle of Locusta migratoria,* Eur. J. Biochem., 195:495, 1991.

Williams, J.M., *Tautomerism of Saccharide Hydrazones in Solution and their Reaction with Nitrous Acid,* Carbohydrate Research, 117:89, 1983.

Either type of immobilisation procedure can be used

Time (min)

5,831,077

GLYCOSYLHYDRAZINES, PREPARATION, IMMOBILIZATION AND REACTIONS OF: GLYCOPROTEIN ANALYSIS AND O-GLYCAN REMOVAL

This application is a 371 of PCT/AU 94/00764 filed on 9 Dec., 1994.

TECHNICAL FIELD

The present invention relates to methods for the production of sugar derivatives, the elimination of sugars from glycoproteins, binding carbohydrates to solid supports and analysis of glycoamino acids using solid phase Edman degradation. All of the disclosures can be applied to monosaccharide or oligosaccharide moieties.

BACKGROUND ART

In view of the developing interest in the importance of the glycosylation of proteins, it has become essential to develop new methods for the study of the detailed structure of complex glycans.

The glycans of glycoproteins are typically either N-linked (attached to asparagine) or O-linked (attached to serine or threonine) [1]. In order to carry out structural analysis of glycoproteins, it is desirable to release the glycans from the protein backbone. To this end, several enzymatic and chemical methods are available. Enzymatic release of N-glycans can be achieved with peptide N-glycosidases and endoglycosidases [2], but relatively few enzymes are available for removal of O-glycans [3]. Chemical treatment with anhydrous hydrazine [4] has been used to remove glycans of both classes, and has been adapted, using milder conditions, for the selective removal of O-glycans [5]. The usual method for the release of O-glycans however is by digestion of the glycoprotein in mild alkali, usually in the presence of borohydride [6]. A significant disadvantage of this method is a reduction of the glycans to alditols and that the reaction is not truly specific for O-glycans as there is significant release of N-glycans due to the inclusion of borohydride.

To date, the most common method for immobilising reducing sugars has been reductive amination [7], whereby the sugars are first attached to polymer-bound primary amino groups by a labile glycosyl amine linkage which is then stabilised by reduction. This reduction is slow and the efficiency of binding is rather low when limited amounts of sugars are available. In recent variations on this approach, the glycosyl amine linkage is stabilised by acylation [8] or Amadori rearrangement [9].

There is a need for site specific identification and characterisation of protein associated glycosylation. Edman degradation is the ideal chemical method for identifying single sites of glycosylation in proteins. The predominant technology of absorption-phase Edman degradation, however, fails to extract the glycosylated amino acid for subsequent analysis. In contrast solid-phase Edman degradation extracts the N- and O-glycosylated amino acids in anhydrous trifluoroacetic acid and each glycosylated amino acid can be collected and subjected to carbohydrate analysis and/or modification (10). The harsh conditions of Edman degradation, however, result in the hydrolysis of sialic acid from the oligosaccharides (FIG. 1). In addition, unless the sialic acid is removed the sialylated oligosaccharide is attached to the solid-support during the immobilisation procedures (FIG. 2). Hence, there is a need to develop a method of modifying sialic acid so as to prevent its immobilisation during the covalent-coupling chemistry and to impart stability during the acid conversion of the sialylated thiazilinone to the thiohydantoin (FIG. 3).

There is a strong need to have simple experimental conditions for the specific release of O-linked glycans from glycoproteins, and for their isolation in an unreduced form suitable inter alia for chemical derivatisation, reductive incorporation of labels or the attachment of polymer supports.

The present inventors have developed chemical modification procedures for the analysis and manipulation of sugars (FIG. 4). It will be appreciated by one skilled in the art that the following disclosures can be applied to monosaccharide or oligosaccharide moieties.

DISCLOSURE OF THE INVENTION

Accordingly, in a first aspect the present invention consists in a method for the production of a sugar hydrazone comprising reacting aqueous hydrazine hydrate with a reducing sugar in the presence of a base, optionally followed by the removal of the hydrazine hydrate and the base.

In one embodiment of the first aspect, the base is sodium hydroxide, preferably at a concentration of 0.1M.

In another embodiment of the first aspect the base is triethylamine, preferably at a concentration of 0.2M.

Preferably, the removal of the hydrazine hydrate from the reaction mixture is by evaporation under reduced pressure or in a stream of inert gas, e.g. $N_2$. When an inorganic base is used, it is removed from the reaction mixture by neutralisation followed by subsequent desalting.

The use of a volatile organic base has the advantage that the base may be removed from the reaction mixture by the same evaporative means used to remove the hydrazine hydrate. In this preferred embodiment of the invention, both the organic base and the hydrazine hydrate are removed by the one step.

Sugar hydrazones are labile to hydrolysis in water, with liberation of the starting sugar. When first isolated in the crude form after formation in hydrazine hydrate, a sugar hydrazone exists substantially in the form of open-chain isomers (true hydrazones) but, in water at pH 7 or below, it rapidly converts to the ring isomers (glycosylhydrazine). Of these isomers, the preferred form is beta-pyranose form, but lesser amounts of the less stable forms, including the furanose forms are also present. The proportions of the precise forms differ for different sugars.

In a second aspect of the present invention the sugar hydrazone of the first aspect is further converted to a sugar pyrazole by reacting the sugar hydrazone with a beta-dicarbonyl compound.

Glycosylhydrazones have not previously been used for the preparation of sugar pyrazoles (glycosylpyrazoles), except for a single report which reported (erroneously) that it was necessary to protect the hydroxyl groups of a glycosylhydrazine before carrying out the reaction [11].

In a preferred embodiment of the second aspect the beta-dicarbonyl compound is acetylacetone.

If the sugar hydrazone is present as a glycosylhydrazine then the corresponding 1-glycosylpyrazole is formed.

A sugar hydrazone, as a ring-form glycosylhydrazine, can form a 1-glycosylpyrazole. This reaction occurs extremely rapidly, and is complete within a few minutes at room temperature. If a sugar hydrazone is present as a mixture of isomeric glycosylhydrazines, a corresponding mixture of glycosylpyrazoles is formed. The open-chain form can react directly with a beta-dicarbonyl compound to form a mixture of glycosylpyrazoles, as cyclisation of the sugar occurs concurrently with formation of the heterocyclic ring.

A mixture of isomeric products is typically formed from a monosaccharide. The situation is more simple in the case of an oligosaccharide or polysaccharide, particularly those in which the reducing terminal sugar residue is substituted in the 4-position, precluding the formation of furanosylpyrazoles.

If one predominant product is required, it is desirable to allow the ring forms of a hydrazone to reach equilibrium, with the beta-pyranose form predominating, before addition of the beta-dicarbonyl compound.

The isomeric forms of the 1-glycosylpyrazoles prepared from glucose, galactose and mannose can be separated by reversed-phase hplc. Particularly good preparative separations have been obtained using a polymeric column, and the pure fractions have been examined by proton nmr spectroscopy and gas chromatography/mass spectrometry (gc-ms) of their trimethylsilyl derivatives. A good feature of their gc-ms is the presence of molecular ions, which allows the determination of the molecular mass of the sugars. This is an advantage over the standard method for gc-ms, using alditol acetates, which does not give molecular ions. Furthermore, the fragmentation modes of the furanose and pyranose isomers are distinctive, with a major fragmentation mode corresponding to loss of side chains. Gc-ms of the glycosylpyrazoles of partially methylated sugars therefore has promise in methylation analysis of glycans.

Given the ease of preparation of glycosylpyrazoles, another promising application is their use in soft-ionisation forms of mass spectrometry, notably fast atom bombardment mass spectrometry (FAB-MS) and electrospray ionisation mass spectrometry (ESI-MS).

In a third aspect of the present invention the glycosylhydrazine of the first aspect is further converted to a 1-glycosylpyrazolone by reacting the glycosylhydrazine with a derivative of a beta-keto acid. A suitable derivative of a beta-keto acid, most simply an ester, is ethyl acetoacetate. Other more reactive derivatives are suitable for this reaction and these include O-hydroxyl succimidyl ester of acetoacetic acid.

In a fourth aspect the present invention consists in a method of converting the glycosylpyrazolone of the third aspect to an azoglycan dye by subjecting the glycosylpyrazolone to azo coupling.

The advantage of the conversion of a glycosylpyrazolone to an azoglycan dye is the intense colour of the dye, which improves the detection of the sugar derivative. A further advantage is that it provides a method for the incorporation of other functional groups. As a simple example, if a glycosylpyrazolone is reacted with diazotised sulfanilic acid (4-aminobenzenesulfonic acid), an acidic dye is obtained. The sulfonic acid group confers a negative charge on the molecule which can then be separated by either anion-exchange chromatography or, more advantageously, by electrophoresis. The electrophoresis will optimally be conducted in a gel, either of polyacrylamide, agarose or a soluble polymer of equivalent properties, and may be used in either the flat bed of capillary configuration.

If desired, the technique of azo coupling can be used to incorporate basic groups, in the form of primary, secondary, tertiary or quaternary amines, in order to confer one or more positive charges on the sugar derivative. This provides great flexibility in the subsequent separation of the derivatives.

A mixture of glycosylpyrazolones can be converted directly to a mixture of azoglycan dyes, or carried out as part of a two-dimensional separation, whereby the glycosylpyrazoles separated by HPLC in the first dimension (such as anion-exchange at high pH with UV detection) and the separated fractions individually converted to charged azoglycan dyes and separated in a second dimension by electrophoresis.

The combination of charge and intense colour of the azoglycan dye makes it ideal for electrophoresis, as an arbitrary amount of charge can be incorporated to give optimal separation and intense colour, making detection simple and sensitive. Furthermore, the colour of the azoglycan dye can be selected by selecting the particular primary amine used for the azo coupling.

Another application of the flexibility of the azoglycan dye chemistry of the fourth aspect of the present invention is the incorporation of hydrophobic groups, by using a primary aromatic amine with for example, a long alkyl subsituent or a polycyclic aromatic amine, such as 4-decylaniline, aminoanthracene, aminopyrene or aminofluorene. The hydrophobicity of the derivative can then be used to immobilise the azoglycan dye on a membrane or hydrophobic plate in such techniques as blotting and immuno assays.

As a further application, exploiting the resistance of the glycosylpyrazolone linkage to acid, an azoglycan dye can be submitted to graded acid hydrolysis, during which a series of oligosaccharide fragments is generated. As noted above, these can be converted to azoglycan dyes which might be of a different colour from the starting compound. When the mixture is separated by electrophoresis, two distinctive series of oligosaccharides will be distinguished on the basis of difference in colour. Given adequate amounts of material, these fragment azoglycan dyes can be isolated and treated further to obtain valuable structural information.

In a fifth aspect the present invention consists in a method for the production of a glycoazomethine dye derivative comprising reacting at the 4-position of a glycopyrolazone of the third aspect with an aromatic C-nitroso compound.

Similar to azoglycan dyes of the fourth aspect, this reaction confers intense colour to the compound and can be used to introduce charge functional groups to assist in, for example, separation of the derivative. Alternatively, this class of derivatives can be prepared by oxidative coupling with a primary aromatic amine. A suitable oxidant for this reaction is a silver salt, but hypochlorite and ferricyanide can also be used. This approach requires the presence of an appropriate second amino substituent on the primary amine. Despite this limitation, the oxidative coupling can be used for displacement coupling to an azoglycan dye. A particularly powerful aplication of this technique is the oxidative covalent blotting onto an arylamine membrane after gel electrophoresis of azoglycan dyes.

A wide range of colours can be obtained for azoglycan and glycoazomethine dyes by selection of the appropriate primary aromatic amine for the reaction. This is of potential value in the stepwise degradation of a complex glycans by either enzymatic or chemical methods. As an illustration, if a glycan is converted to an azoglycan and glycoazomethine dye of colour 1 and treated with an exoglycosidase to liberate a monosaccharide subunit, the liberated subunit can be converted, without separation, to an azoglycan dye of colour 2 in the presence of the remaining colour 1. The distinction between these colours will often be of value in assessing the outcome of exoglycosidase treatment.

The derivatisation methods may be suitable to further analyse Edman sequencing fragments from glycoproteins whereby the modified PTH-glycoamino acid is isolated from sequencing and further treated with aqueous hydrazine hydrate to form glycosylhydrazones, converted to glycosylpyrazolones and azo coupled with aminonaphthalene sulfonic acid, reduced to hydrazoglycan dyes and separated by electrophoresis using fluorescence as a detection.

The flexibility of incorporation of charge functional groups in azoglycan dyes enables the formation of derivatives for soft-ionisation mass spectrometry, as they permit the localisation and stabilisation of either positive or negative charge in a glycan. This has a particular promise for sequencing of glycans as there is no ambiguity in the location of the charge. This has particular potential for the determination of structures of complex glycans, by integration of separation (by HPLC and/or by electrophoresis) with on-line electrospray mass spectrometry (ESI-MS). This is turn can be integrated with controlled degradation using enzymatic or chemical methods.

In a sixth aspect the present invention consists in a method of producing a hydrazoglycan dye comprising reacting an azoglycan dye of the fourth aspect with a reducing agent.

The reducing reagent for this conversion is selected from the group consisting of hydrosulfide, diimide (preferably generated in situ by oxidation of hydrazine), and formamidinesulfinic acid. The hydrogen donor is methanol in alkaline solution and the hydride transfer catalyst, is a quinone or an aromatic ketone.

The reaction is carried out without cleaving the azolinkage of the dye. Improved detection of some azoglycan dyes can be obtained by converting them to the reduced hydrazoglycan dyes. In general, these will not be intensely coloured but, where there are appropriate moities present, notably napthalene, pyridine, quinoline, anthracene and fluorene, the hydrazo will have intense fluorescence. This reduction coverts the azo group of the azoglycan dye to the hydrazo form (by addition of 2 atoms of hydrogen).

In a seventh aspect the present invention consists in a method of cleaving the azo linkage of an azoglycan dye of the fourth aspect comprising treating the azoglycan dye with a reducing agent.

The reducing agent preferably being dithionite in either neutral or alkaline solution, sulfide or polysulfide. A useful application of this aspect is the removal of polymer-bound azoglycan dyes.

The availability of a method for the reductive cleavage of azoglycan dyes can be exploited in various ways, such as:
1. The covalent attachment of a glycosylpyrazolone to a polymer support, to permit convenient and efficient modification of the structural modification (remodelling) of the glycan using a combination of glycosidases and glycosyltransferases. The modified glycan can then be removed by reductive cleavage to give a 4-aminoglycosylpyrazolone, which can be coupled by a variety of condensation or acylation reactions to give derivatives with highly favourable properties for separation and detection.
2. The covalent blotting of an electrophoresis gel onto a diazotised arylamine membrane, followed by immunochemical detection. Following detection, the antibody or lectin can be removed by manipulation of pH, or by hapten displacement, and the glycan recovered from excised sections of the membrane by reductive cleavage. As before, the recovered 4-aminoglycosylpyrazolone can be modified before submitting to further study.

In an eighth aspect, the present invention consists in a method of production of an azoglycan dye comprising the following steps:

i) reacting an aqueous hydrazine hydrate with a reducing sugar to form a glycosylhydrazone;
ii) reacting the glycosylhydrazone of step (i) with a derivative of a beta-keto acid to form a glycosylpyrazolone; and
iii) subjecting the glycosylpyrazolone of step (ii) to azo coupling to form an azoglycan dye.

In one embodiment of the eighth aspect of the present invention consists in a method for the production of an hydrazoglycan dye comprising reacting the azoglycan dye of step (iii) above with a reducing agent to form a hydrazoglycan dye.

In another embodiment of the eighth aspect of the present invention consists in a method for the production of a glycoazomethine dye derivative comprising reacting at the 4-position of the glycosylpyrazolone of step (ii) above with an aromatic C-nitroso compound to form a glycoazomethine dye.

In a further preferred embodiment of the eighth aspect, the derivative of the beta-keto acid, most simply an ester, is ethyl acetoacetate. Other derivatives are also suitable for this reaction and include the O-hydroxyl succimidyl and trifluoroethyl esters of acetoacetic acid.

In a still further prefered embodiment of the eighth aspect, the reducing agent is selected from the group consisting of hydrosulfide, diimide (preferably generated in situ by oxidation of hydrazine) and formamidinesulfinic acid. Most preferably, the reducing agent is hydrosulfide or formamidinesulfinic acid. The hydrogen donor is methanol in an alkaline solution and the hydride transfer catalyst is a quinone or an aromatic ketone.

In a ninth aspect, the present invention consists in a method for the removal of O-glycans from a glycopeptide or glycoprotein having O-glycans comprising reacting a glycopeptide or glycoprotein with aqueous hydrazine hydrate in the presence of a base at an elevated temperature, eg. greater than 20° C., for a period sufficient to remove the O-glycans in the form of glycan hydrazones without releasing N-glycans.

In a preferred embodiment of the ninth aspect, the glycopeptide/glycoprotein is reacted with 0.2M triethylamine in 50% (v/v) aqueous hydrazine and the reaction is incubated at 25°–45° C. for a period up to 16 hours.

In a further preferred embodiment of the ninth aspect, the removed glycan hydrazone which is protected from betaelimination is further converted to a reducing sugar. Preferably the conversion is by N-acetylation with acetic anhydride and a mild base (preferably sodium hydrogen carbonate) and followed by treatment with an excess of aqueous acetone.

The deglycosylated peptide/protein can be separated from the removed glycan derivative(s) using standard chromatography techniques. Preferably, the separation is by gel or reversed-phase chromatography.

In a further embodiment of the ninth aspect, the removed glycan hydrazones are converted to heterocyclic pyrazole derivatives by treatment with a beta-dicarbonyl compound at room temperature. The newly formed derivatives may be separated by standard techniques including ion-exchange reversed-phase or straight-phase HPLC. They are also suitable for separation by micellar electrokinetic capillary chromatography.

In a still further embodiment of the ninth aspect, the sugar hydrazone derivatives are further converted to 1-glycopyrazolones by the method of the third aspect of the present invention which are further converted to azo dyes by the method of the fourth aspect of the present invention.

The existing literature methods of releasing glycans from glycoproteins use anhydrous hydrazine and this leads to extensive fragmentation of the protein chain. The present inventors however have determined that the release of glycans from glycoproteins can be controlled by the treatment with aqueous hydrazine. In one form, O-glycans can be released specifically in the presence of N-glycans by treatment with 50% aqueous hydrazine containing 0.2M triethylamine at 45° C. for 4 to 6 hours. In addition, N-glycans can be released specifically in the presence of O-glycans by treatment with aqueous hydrazine without the addition of triethylamine. As the glycans are released, they are rapidly converted to hydrazones, which are stable under basic conditions (the free reducing sugars are not stable).

The reducing sugars can be regenerated from the hydrazones by methods including acetylation followed by very mild acid hydrolysis. The reducing sugars so produced are suitable for the incorporation of ultraviolet-absorbing and fluorescent tags to enable detection of the sugar derivatives at low concentrations. As a result, the present invention for the release of reducing sugars represents an important advance over the existing method of reductive elimination of glycans, as the reducing glycans can be obtained simply and efficiently.

Furthermore, the present inventors have developed an important new use of the sugar hydrazones produced by the present invention for the incorporation of new groups onto the sugar, such as pyrazoles, pyrazolones, azopyrazolones (azoglycan dyes), hydrazopyrazolones (hydrazoglycan dyes) and azomethines. The present invention represents an important tool for the study and analysis of glycans from glycoproteins.

Many forms of aqueous hydrazine are suitable for the reaction with reducing sugars including mono-and di-substituted forms of hydrazine. In particular methyl hydrazine and N, N-dimethylhydrazine are preferred forms, but only unsubstituted hydrazine is suitable for the present application if the glycosylhydrazine is to be used directly for formation of heterocyclic derivatives.

The sugar hydrazones produced by the present invention also include modified sugar hydrazones, including FMOC and other fluorescent derivatives, condensation products, prepared by linkage of aromatic aldehydes and ketones (with or without subsequent reduction to stabilise the linkage) and alkylation and arylation products, such as those prepared with a benzylic or phenacyl halide or an active arylhalide, such as fluorodinitrobenzene and NBD chloride.

The glycan derivatives of the present invention have many uses and such uses include the following:
(a) incorporation of groups to improve ultraviolet and fluorescence detection of glycans;
(b) the improvement of chromatographic properties of the glycans to enable more effective separation;
(c) a combination of (a) and (b) above to provide more effective methods for chromatographic analysis of glycans;
(d) the incorporation of charged groups to enable the electrophoretic separation of glycans (in conjunction with (a) above this would lead to further improvement in analysis of glycans);
(e) the incorporation of a hydrophobic tag which will confer amphiphatic properties on the glycan conjugate;
(f) the use of the glycan carrying a hydrophobic tag for the immobilisation of the glycan for use in immunochemical analysis (optimally, this would use 96-well plates coated with the tagged glycan and optimally, the glycan tag will be colourless, such as in the hydrazoglycan, in order to minimise interference in the immuno-assay);
(g) the use of the glycan carrying the hydrophobic tag as an antigen for the production of anti-glycan antisera, in conjunction with established adjuvants; and
(h) the use of various methods, employing glycan hydrazones and intermediates, for the preparation of specialist packings with immobilised glycans for the affinity chromatography of anti-glycan antisera and lectins. The methods for the preparation of these packings include the reaction of glycan hydrazones with isothiocyanato-functionalised activated packings, the formation of glycan pyrazolones and coupling to a diazonium-functionalised packing and the direct linkage of the glycan hydrazones with a packing carrying a beta-dicarbonyl moiety.

The present invention is suitable for integration with other separation and biological techniques used in the art. In particular the glycan derivatives of the present invention are suitable for analytical methods to glycoprotein samples in all forms of presentation, including solutions, electrophoretic gels after separation, and blots obtained after electrophoretic separation.

As one example of the integrated separation and analysis of a biological sample is whereby the sample is separated by two-dimensional electrophoresis, the resultant gel blotted onto a membrane and stained.

Sections of the membrane, corresponding to single molecular species of glycoproteins, are then excised and subjected to the following sequence manipulations:
(a) amino acid analysis;
(b) total sugar analysis;
(c) N-terminal sequence analysis;
(d) protease digestion and profiling of the resultant peptides;
(e) chemical release of the glycans followed by profiling and analysis using a selection of the aspects of the present invention.

It is recognised that the information obtained from this combination of techniques, together with other information on pI and molecular size obtained from electrophoresis and gene sequences available in data bases, will often be sufficient to permit full characterisation of the protein present in a particular electrophoretic blot.

In a tenth aspect, the present invention consists in a method of immobilising a reducing sugar to a solid support having primary or secondary amine groups comprising converting the reducing sugar to a sugar hydrazone, converting the amine groups on the solid support to isothiocyanate groups and reacting the sugar hydrazone with the isothiocyanate-substituted support so as to cause the binding of the sugar to the support.

In a preferred embodiment of the tenth aspect, the solid support is a polystyrene or any other chemically inert polymer support.

In a further preferred embodiment of the tenth aspect, reducing sugar is bound irreversibly to the solid support by heating the solid support at slightly acidic pH.

Carbohydrates bound to polymer beads can be examined using immunological or lectin affinity techniques before or after treatment with glycosidases or using appropriate chemical means to remove terminal sugars. In this way, oligosaccharide structures can be examined.

Alternatively the bound carbohydrates can be modified (e.g. by methylation) and the linkage structure determined after hydrolysis.

In an eleventh aspect, the present invention consists of a method to obtain sugars from a glycopeptide/glycoprotein comprising subjecting the glycopeptide/glycoprotein to Edman degradation, separating the glycoamino acid derivative, collecting, quantitating and characterising the glycoamino acid derivative. It will be obvious to one skilled in the art that the glycoamino acid derivatives recovered from Edman degradation (the thiohydantoin, thiocarbamyl or thiazilinone) can be manipulated using the first, second and third aspects of the present invention.

In a preferred embodiment of the eleventh aspect, the glycoamino acid derivative is analysed by high performance liquid chromatography, electrophoresis or mass spectrometry either directly or after chemical glycosidase treatment.

In a further preferred embodiment of the eleventh aspect, free carboxyl groups of the glycoprotein/glycopeptide are manipulated so as to prevent either:
1. the hydrolysis of terminal sialic acids during Edman degradation of peptides or proteins bound via amino acid side chain amine groups to an immobilised isothiocyanate group; or
2. amide coupling of the free carboxyls to an immobilised amine group.

Preferably the manipulation is by removal of the sialic acids on the sugars and/or amidation of the free carboxyl groups.

In order that the nature of the present invention may be more clearly understood, preferred forms thereof will be described with reference to the following examples and the accompanying drawings.

MODES FOR CARRYING OUT THE INVENTION

Figure 1A:
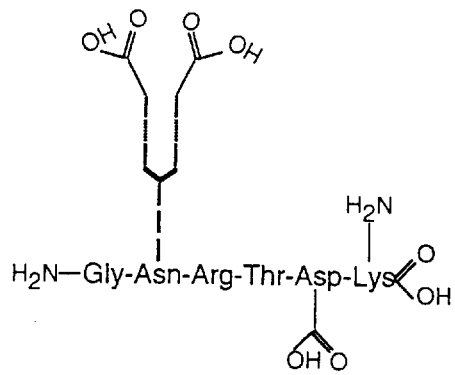
FIG. 1 shows a diagram of binding chemistry in Edman degradation. A) N-linked glycopeptide which contains both alpha and side chain carboxyls, including terminal carboxyls on the N-linked oligosaccharide. B) Immobilisation via the amine groups of the protein to immobilised isothiocyanate groups demonstrates that a C-terminal lysine is necessary for prolonged sequencing. Note that no part of the oligosaccharide is immobilised. C) Following two cycles of Edman degradation the terminal sialic acids are lost during the acid conversion of the thiazilinone to the thiohydantoin. Therefore only the desialylated oligosaccharide is recovered attached to the PTH-Asn.
Figure 1B:
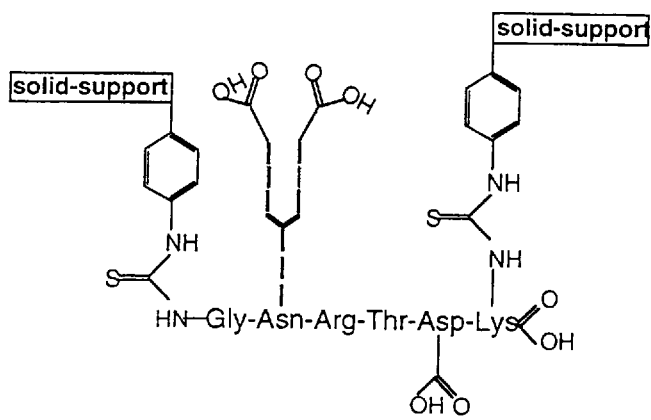
Figure 1C:
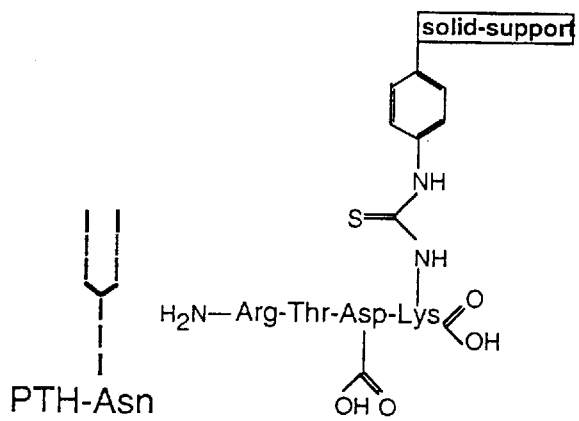
Figure 2A:
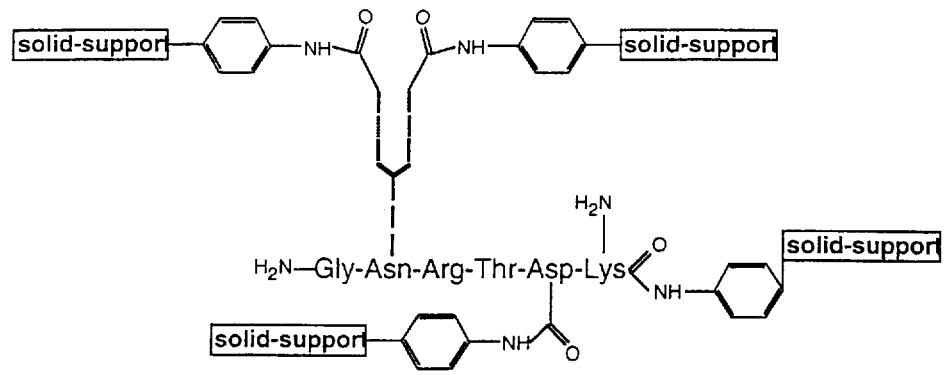
FIG. 2 shows a diagram of binding chemistry. A) Coupling via the side chain and terminal carboxyls to an immobilised amine via water soluble carbodiimide demonstrates that all carboxyls groups, including the terminal sialic acid carboxyls, are immobilised. B) Following two cycles of Edman degradation the ATZ-glycoamino acid is cleaved from the peptide but remains bound to the solid support. C) Desislylation of the glycopeptide prior to immobilisation prevents coupling of the terminal sialic acid carboxyls to the solid support. As in FIG. 1C only the desialylated oligosaccharide is recovered attached to the ATZ-Asn.
Figure 2B:
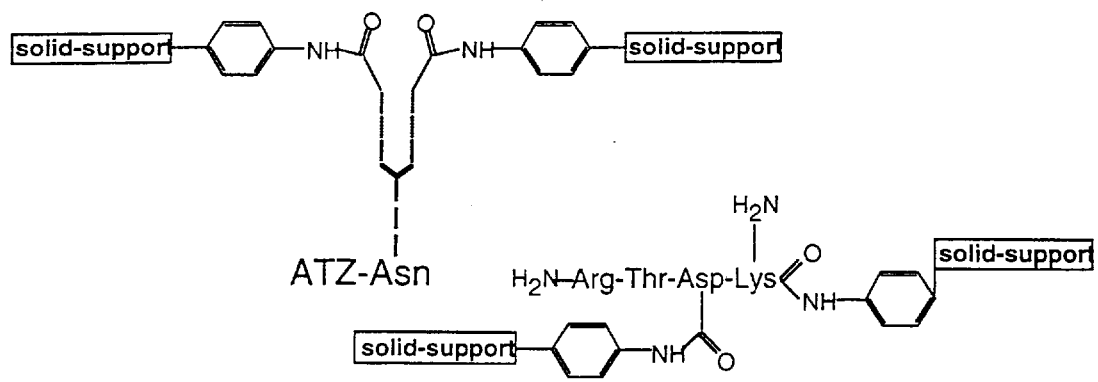
Figure 2C:
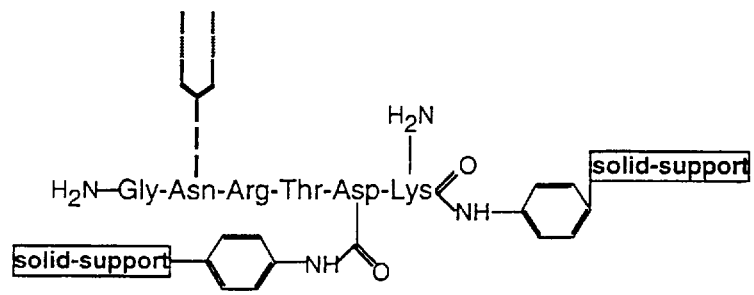
Figure 3A:
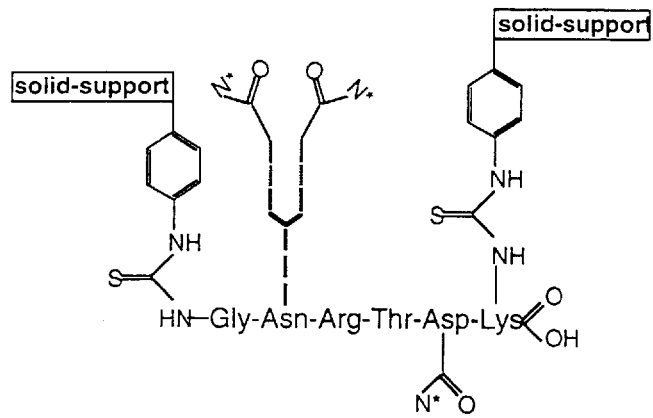
FIG. 3 shows a diagram of binding chemistry. A) Amidation of the peptide does not effect isothiocyanate immobilisation as long as the peptide contains a Lysine C-terminal to the glycosylation site. B) Arylamine immobilisation of the amidated peptide is dependent on the generation of a free alpha carboxyl. In this figure an alpha carboxyl is obtained following trypsin or End Lys-C digestion. C) Following two cycles of Edman degradation the ATZ-glycoamino acid is recovered regardless of how the peptide is immobilised. Importantly the amidated form of the glycoamino acid is resitant to acid hydrolysis.
Figure 3B:
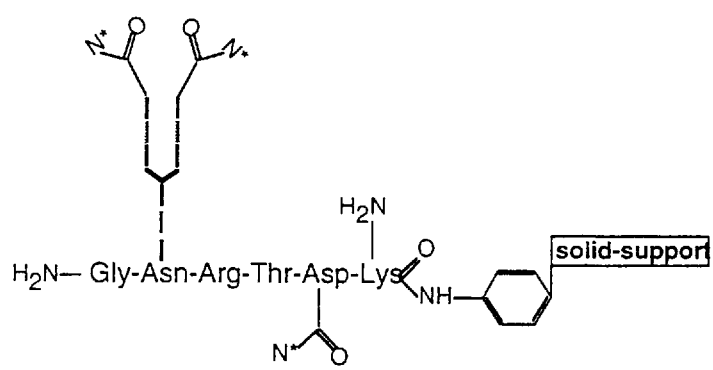
Figure 3C:
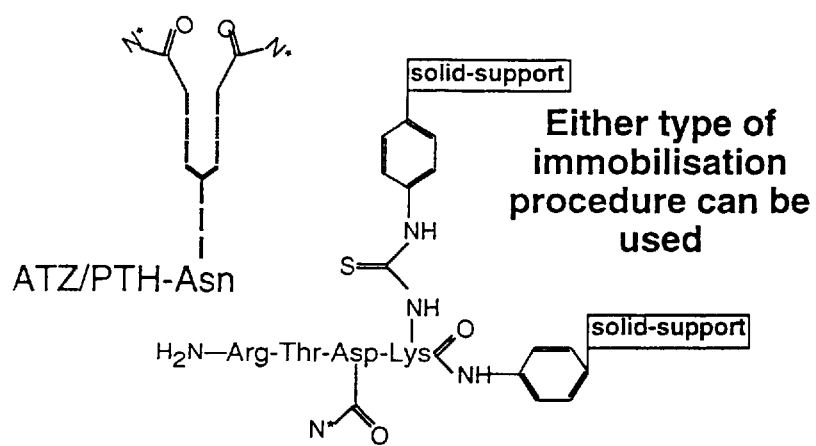
Figure 4:
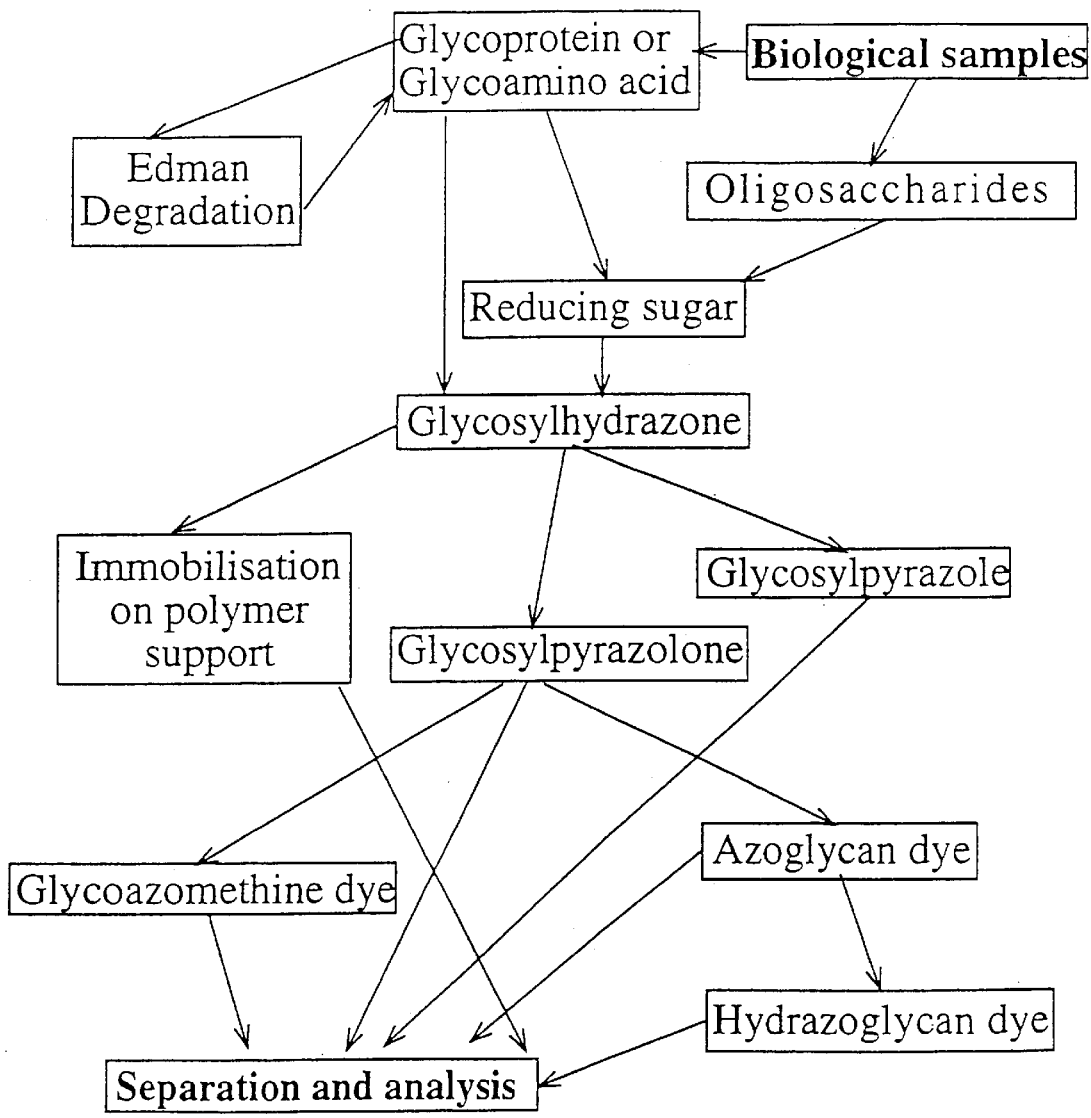
FIG. 4 is a schematic representation of the proposed uses of the sugar derivatives of the present invention.
Figure 5:
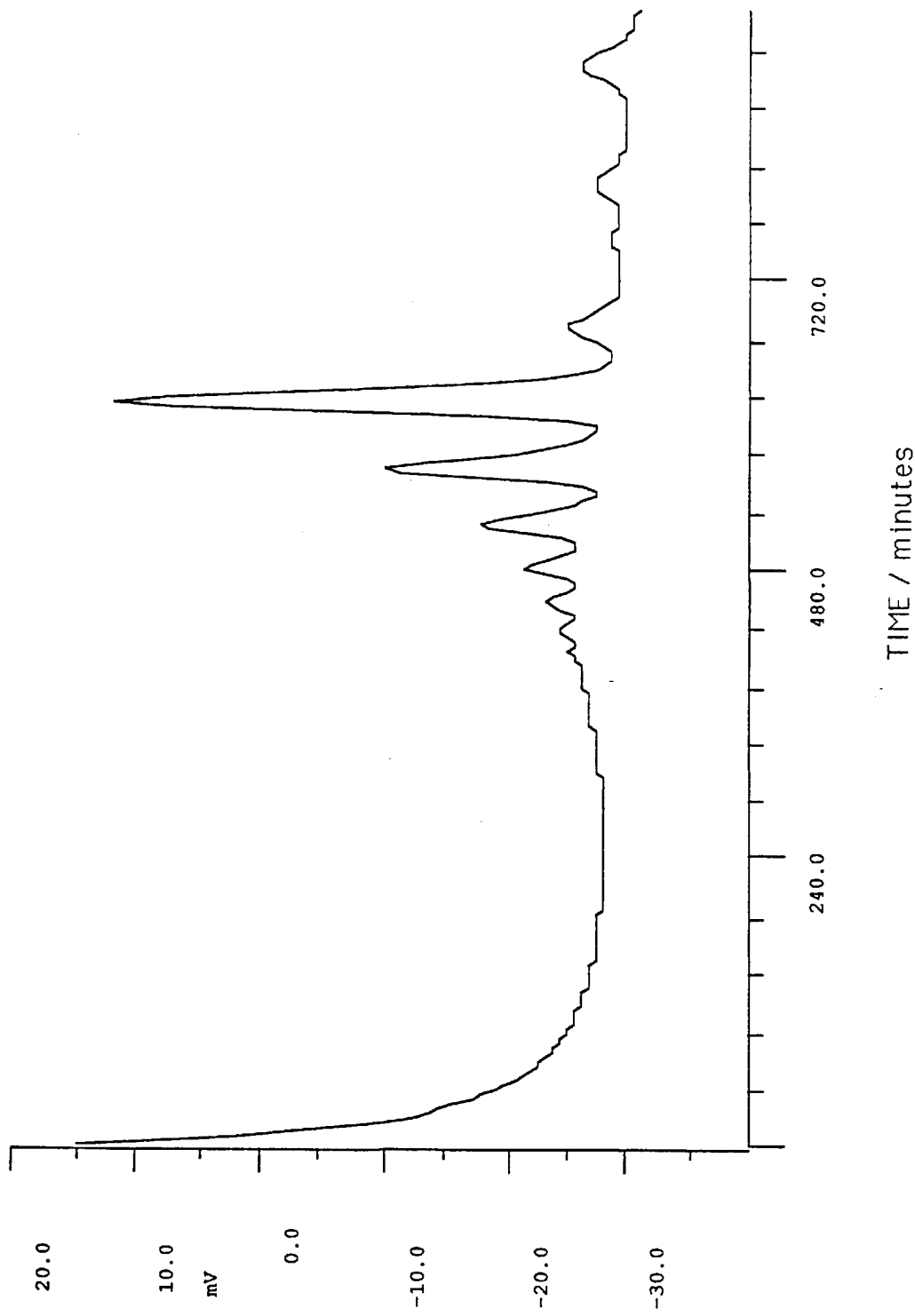
FIG. 5 shows separation of 25 µg glucose syrup pyrazoles on an open Fractogel HW40S column (60 cm×25 mm) at a flow rate of 0.2 ml/min. Detection was by UV absorbance at 220 nm with full scale absorbance at 0.01 AU.
Figure 6:
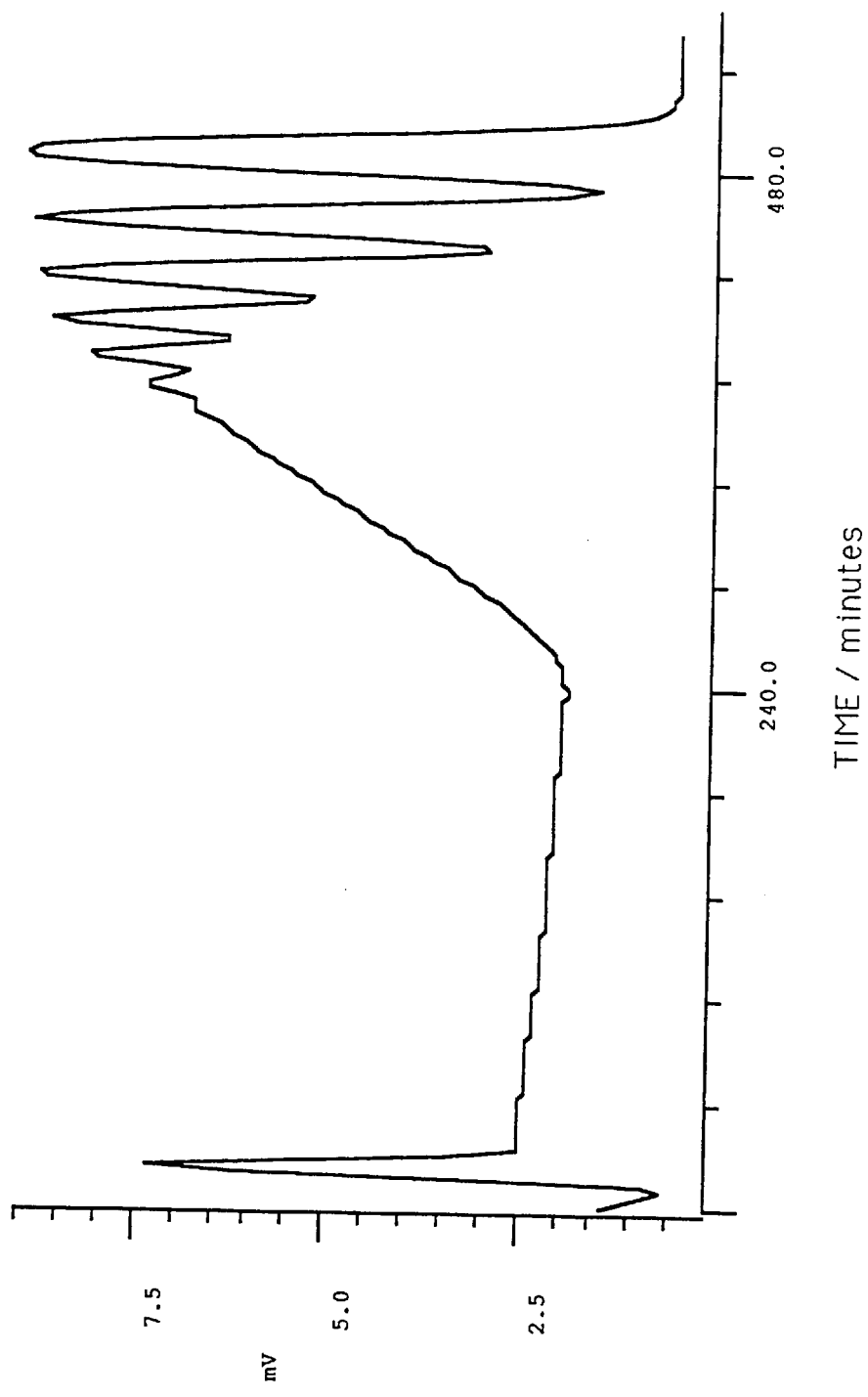
FIG. 6 shows comparison of separation of 25 mg non derivatised glucose syrup on Fractogel HW40S (60 cm×25 mm) at a flow rate of 0.2 ml/min. Detection was by RI with a full scale refractive index units of $1 \times 10^5$.
Figure 7:
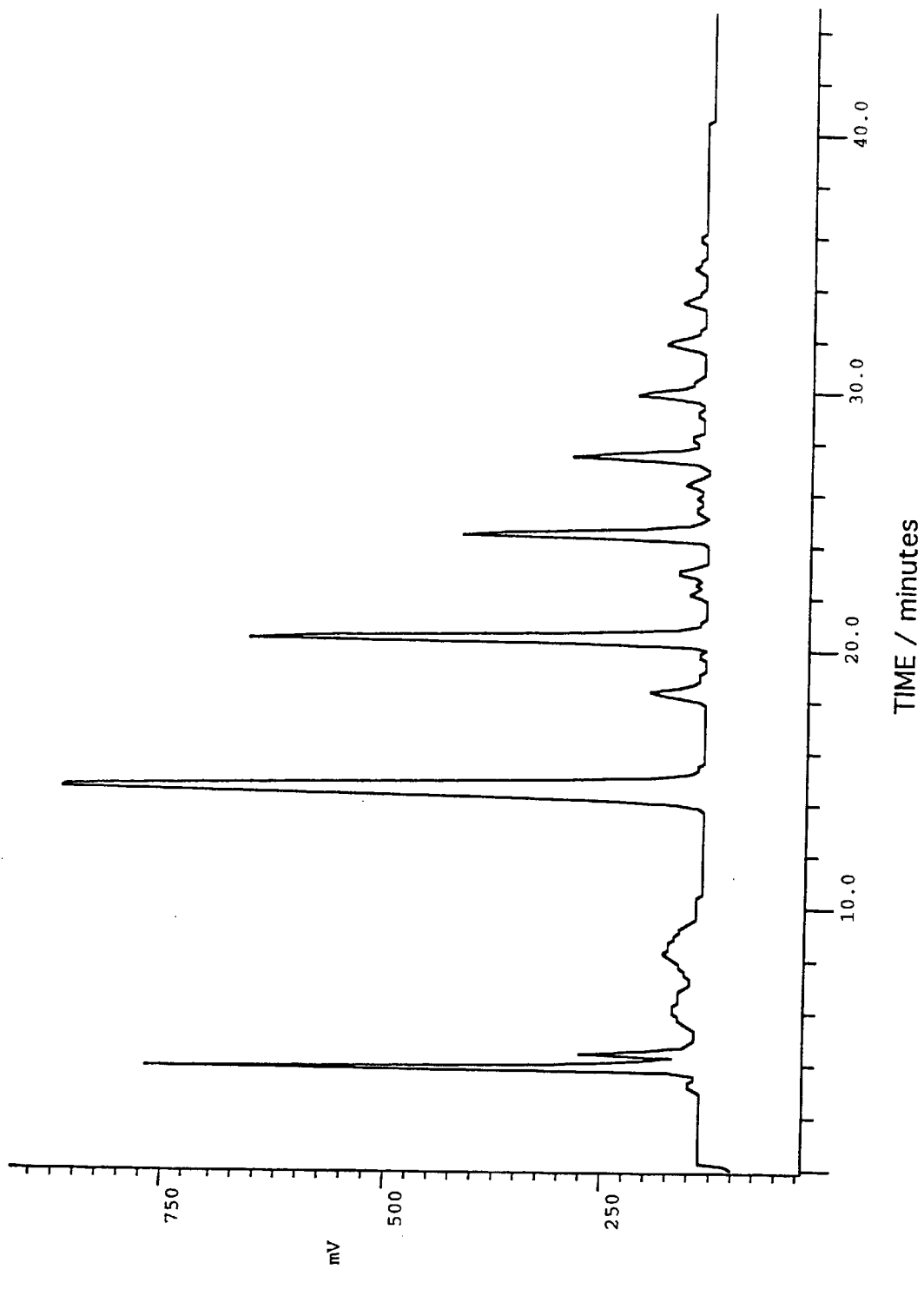
FIG. 7 shows separation of 25 µg glucose syrup pyrazoles on an aminopropyl HPLC column (250 mm×4.6 mm) usind a gradient of 10% acetonitrile to 60% acetonitrile in water over 40 min. Flow rate of 1 ml/min with detection at 220 nm Glucose pyrazole elutes at 15 min.
Figure 8:
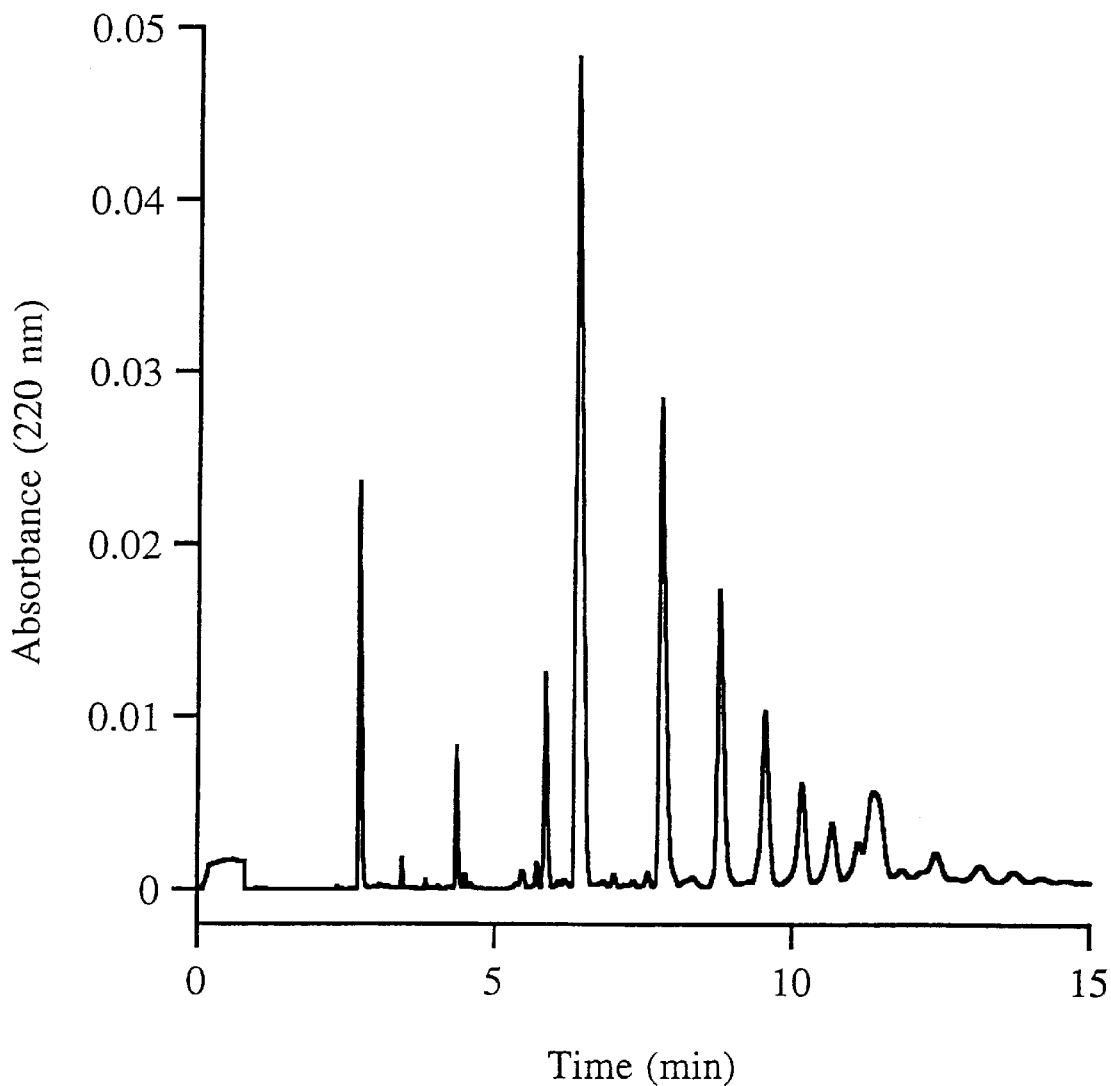
FIG. 8 shows separation of 25 µg glucose syrup pyrazoles by capillary electrophoresis (12 cm×0.75 µm ID) using 0.1M $H_3PO_4$, 8 kV, 70 µA, 3 sec inject of 2 mg/ml syrup. Detection was by UV absorbance at 226 nm. Glucose pyrazole is at 6.5 min.
Figure 9A:
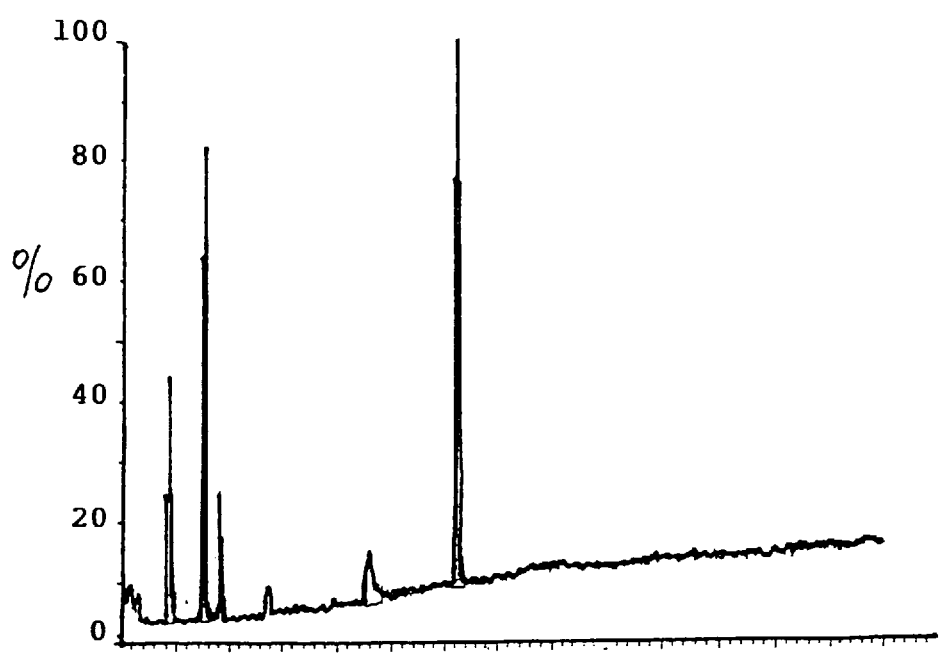
FIG. 9 shows GC-MS of TMS derivatives of a) galactose pyrazole and b) glucose pyrazole separated on a BPX5 column on a program of 180° C. to 300° C. at 5° C./min.
Figure 9B:
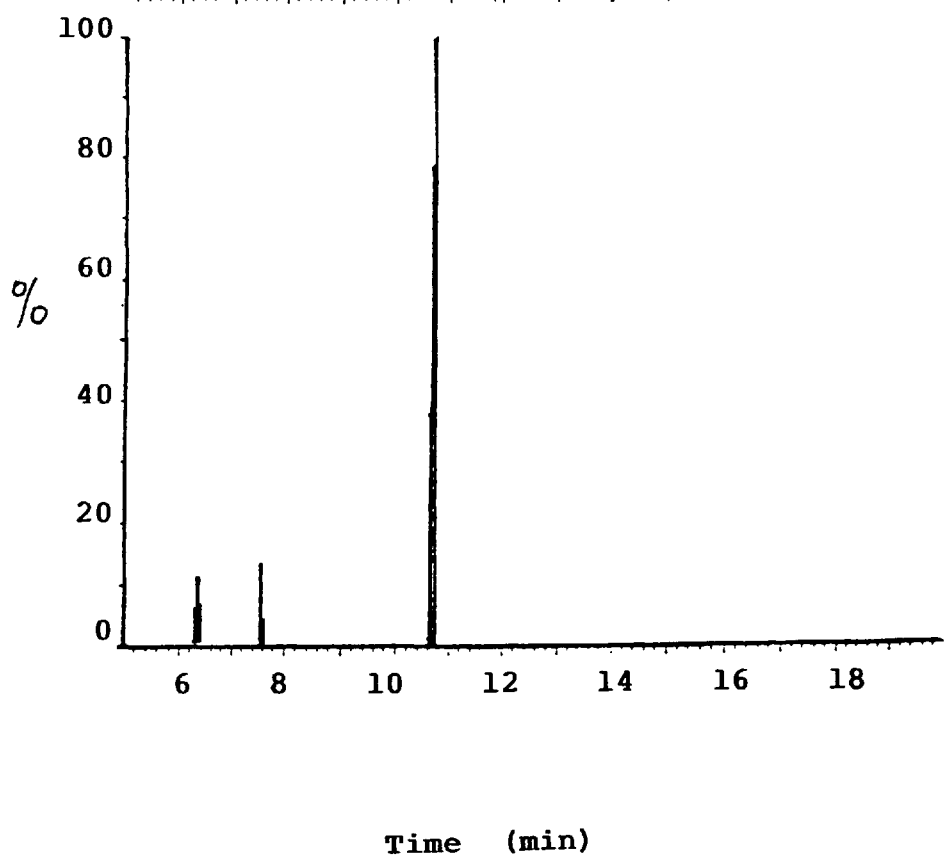
Figure 10:
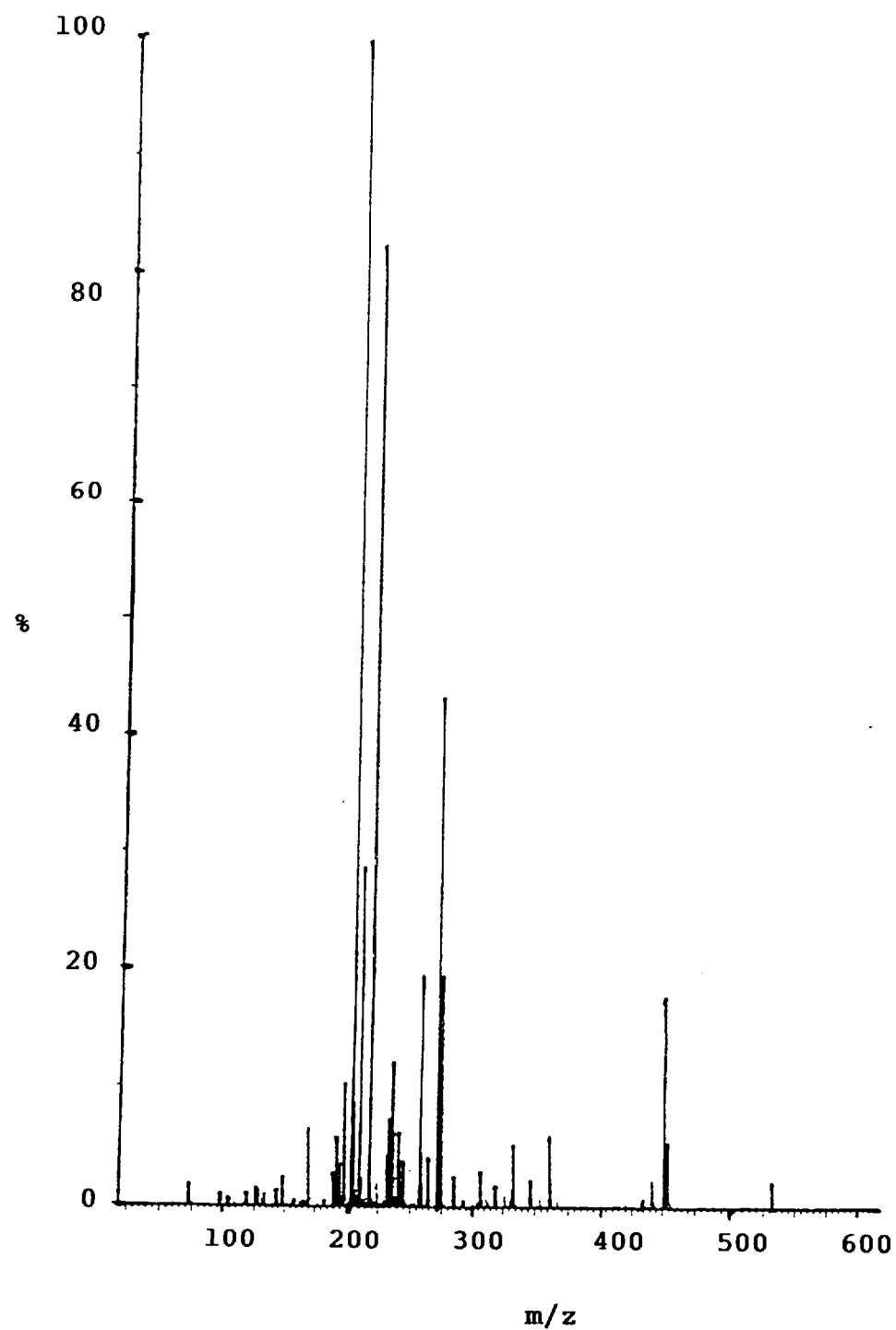
FIG. 10 shows EI fragmentation mass spectrum of the TMS derivative of glucose pyrazole. Molecular ion (546.28 mu) can also be seen.
Figure 11:
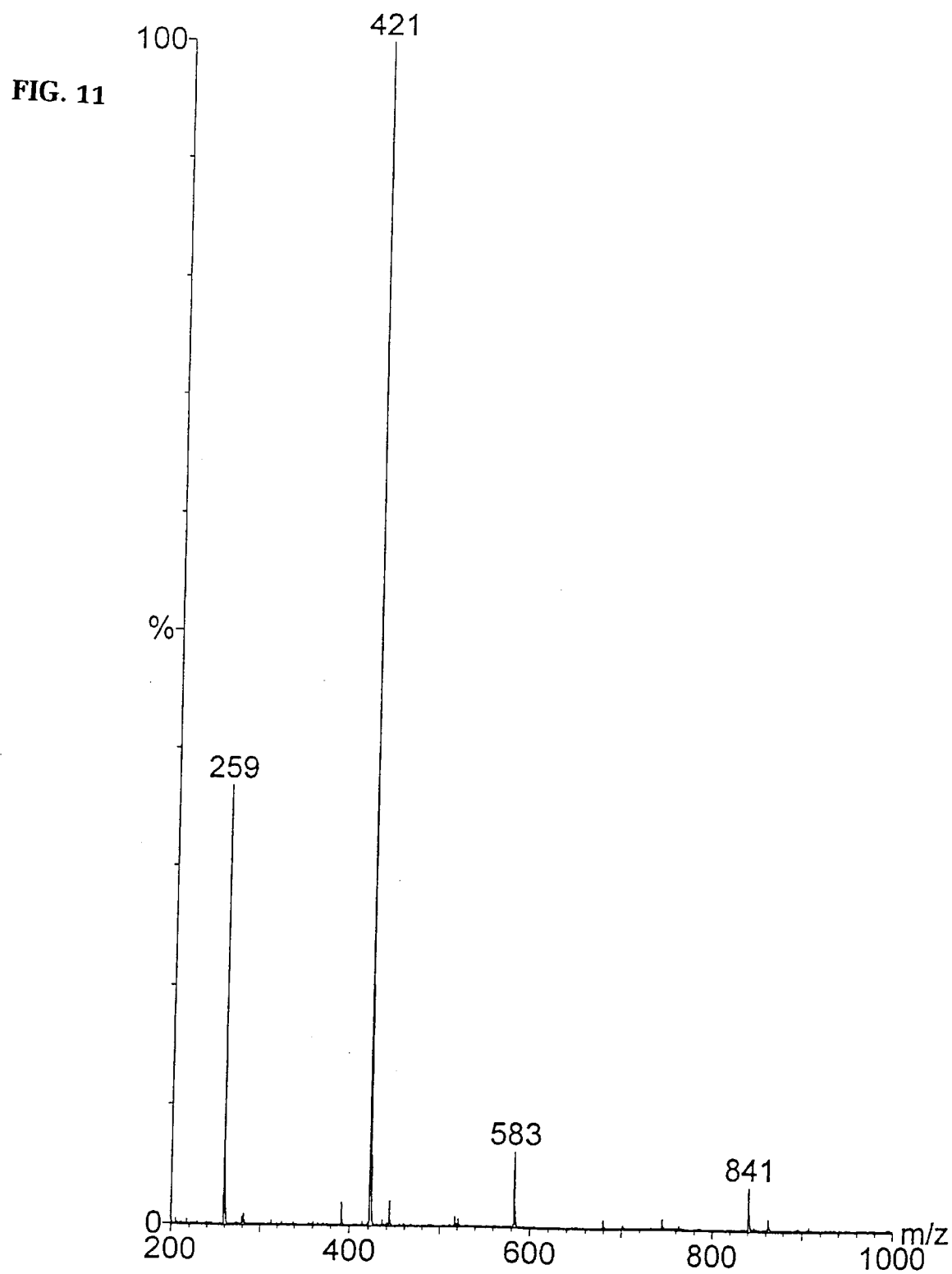
FIG. 11 shows the ionspray mass spectrum of maltose pyrazole.
Figure 12:
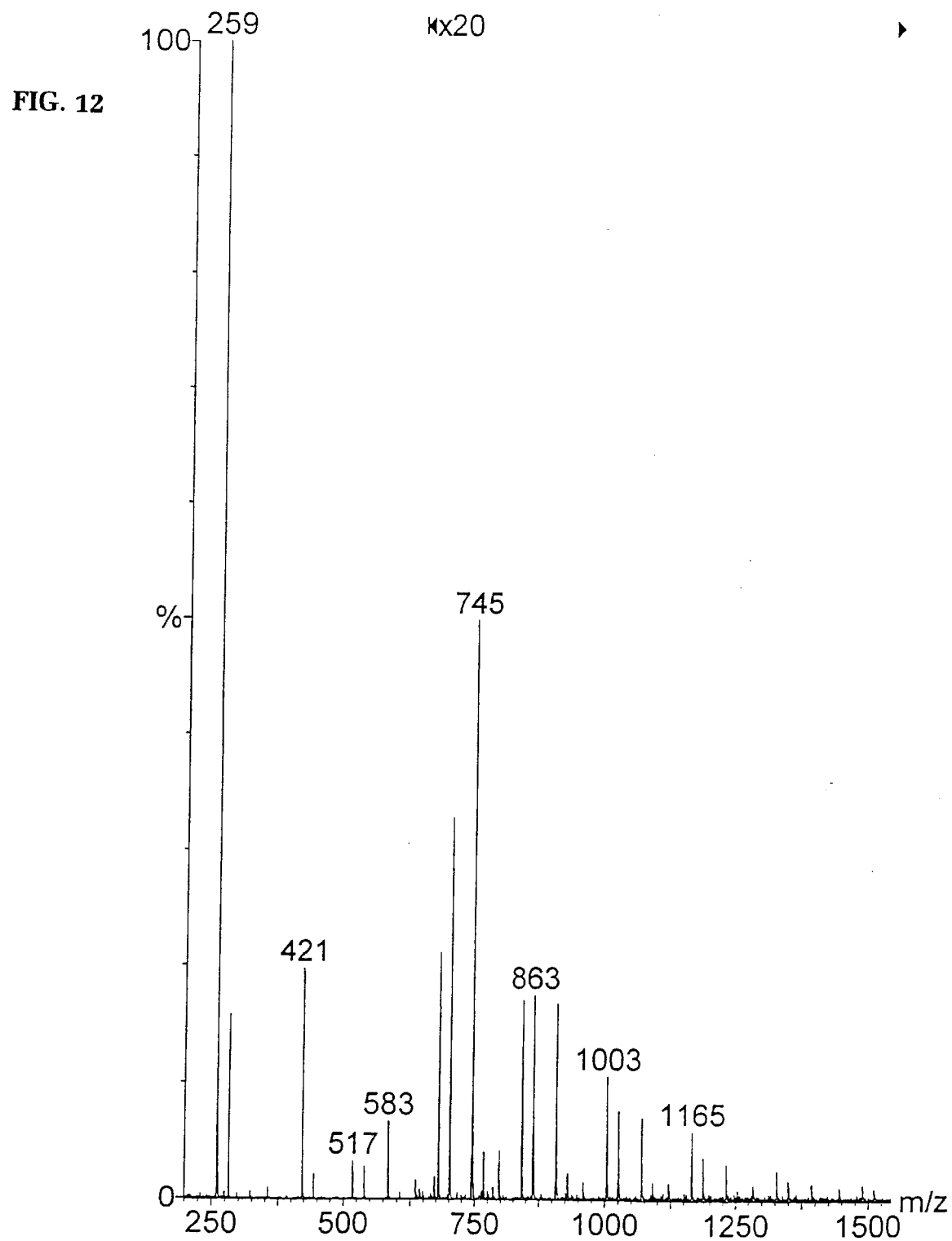
FIG. 12 shows the ionspray mass spectrum of the pyrazoles derived from glucose syrup. The sugar pyrazoles (pyrazole-SAC) of chain length 1–11 have clearly been identified.

I. FORMATION OF HETEROCYCLIC DERIVATIVES OF SUGARS: GLYCOSYLPYRAZOLES AND GLYCOSYLPYRAZOLONES

Sugar hydrazones can be prepared by addition of aqueous hydrazine hydrate to reducing sugars and evaporation under reduced pressure. At equilibrium in water, they do not exist as true open-chained hydrazones, but rather as the cyclic forms, with the β-anomer as the dominant isomer. The hydrazones have only limited shelf life, but can be converted to stable heterocyclic derivatives by standard procedures.

The present inventors have converted the hydrazones of monosaccharides and oligosacchardies into 1-glycosylpyrazoles by condensation with acetylacetone. This conversion occurs within minutes at room temperature, and is highly suitable for the preparation of derivatives for HPLC, as the products are stable and have good UV-absorption properties. 1-glycosylpyrazolidin-5-ones, which have even better absorption properties, can be prepared by condensation with ethyl acetoacetate.

This basic chemistry can be extended to the production of intensely colored sulfonic acid derivatives of 1-glycosylpyrazolidin-5-ones which are ideal for the separation of sugars by polyacrylamide gel electrophoresis. In general, these derivatives are prepared by condensation of sugar hydrazones with β-ketoesters, followed by coupling with diazotised primary aromatic amines, such as sulfonilic acid. The general approach provides great flexibility. For example, the glycosylpyrazolidinones can be prepared and separated in a first dimension by any suitable HPLC procedure, such as reversed-phase or ion-exchange HPLC. The fractions obtained can then be azo coupled to give a product with either sulfonic acid or quaternary ammonium substituents which will allow separation by capillary or slab-gel electrophoresis and a further dimension of characterisation by electrospray MS.

It should be noted that quite extraordinary resolutions of sulfonic acid derivatives of sugars have already been demonstrated by capillary gel electrophoresis and by a commercial slab gel system. Those methods do, however, involve cumbersome and inefficient derivatisation chemistry. The new approach by the present inventors helps to overcome the prior art deficiencies.

Formation of glycosylhydrazine

A solution of a reducing sugar (5 µg–5 mg) was evaporated to dryness in a 1.5 ml plastic centrifuge tube. The residue was dissolved in hydrazine hydrate (0.05 ml) and allowed to stand at room temperature for 30 min before evaporation in a vacuum desiccator containing concentrated sulfuric acid. The evaporation was complete after 2 h. To ensure effective removal of hydrazine, the residue was twice dissolved in water (0.05 ml) and re-evaporated. $^{14}$C N-acetylglucosamine was treated in the same way with 25% aqueous hydrazine hydrate for 6 h before evaporation. Sugar hydrazones were stored dry in the freezer for up to 2 months.

Formation of glycosylpyrazoles

A solution of glycosylhydrazone, prepared from 5 µg–5 mg of sugar as above, is added to a 1.5 ml plastic centrifuge tube and an aqueous solution of acetylacetone (10%, 0.05 ml) added. The solution was allowed to stand for 30 min at room temperature and evaporated to dryness in a desiccator or in a stream of nitrogen.

Separations of glycosylpyrazoles

The glycosylpyrazole derivatives have excellent properties for separation and detection using different modes of chromatography and electrophoresis (FIGS. 5–12).

Formation of glycosylpyrazolones

A solution of glycosylhydrazone, prepared from 5 µg–5 mg of sugar as above, is added to a 1.5 ml plastic centrifuge tube and water (0.050 ml) and ethyl acetoacetate (0.01 ml) added. The solution was heated in boiling water for 60 min and evaporated to dryness in a desiccator or in a stream of nitrogen.

Formation of azoglycan dyes

To a solution of a glycosylpyrazolone (formed from glucose syrup) in 0.01M sodium hydroxide (0.05 ml)was added a solution of freshly diazotised 1-naphthylamine or p-toluidine (0.05 ml). The intense colour of an azo dye was formed immediately.

Reduction of an azoglycan dyes to fluorescent hydrazoglycan dyes

To a solution of an azoglycan dye which has been adjusted to pH approximately 10 by the addition of ammonium hydroxide, solid formamidinesulfinic acid is added and the mixture warmed at 30° C. for 5 min. During this time, the intense colour of the azoglycan dye was discharged, with the production of the corresponding colourless hydrazoglycan derivative. In the case of the reduction of the azoglycan dye formed using 1-naphthylamine, the hydrazoglycan derivative was highly fluorescent.

Figure 14:
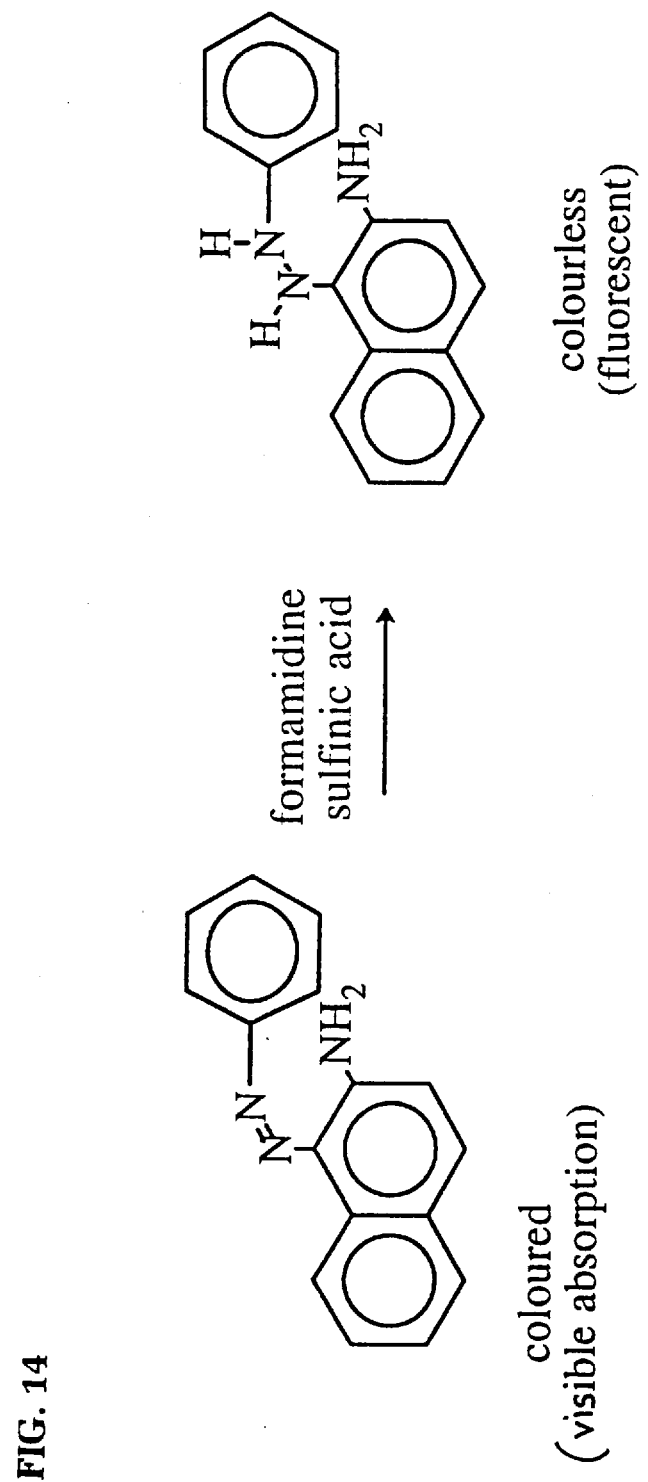
FIG. 14 shows the reduction reaction, whereby an azo dye is reduced to a colourless, fluorescent product.

The validity of this chemistry was confirmed by the reduction of a commercial azo dye, benzeneazo-β-naphthylamine, (FIG. 14). Under identical conditions, the characteristic orange colour was discharged, with the production of a highly fluorescent, colourless product.

Formation of azoglycan and hydrazoglycan derivatives from a polysaccharide

Figure 13:
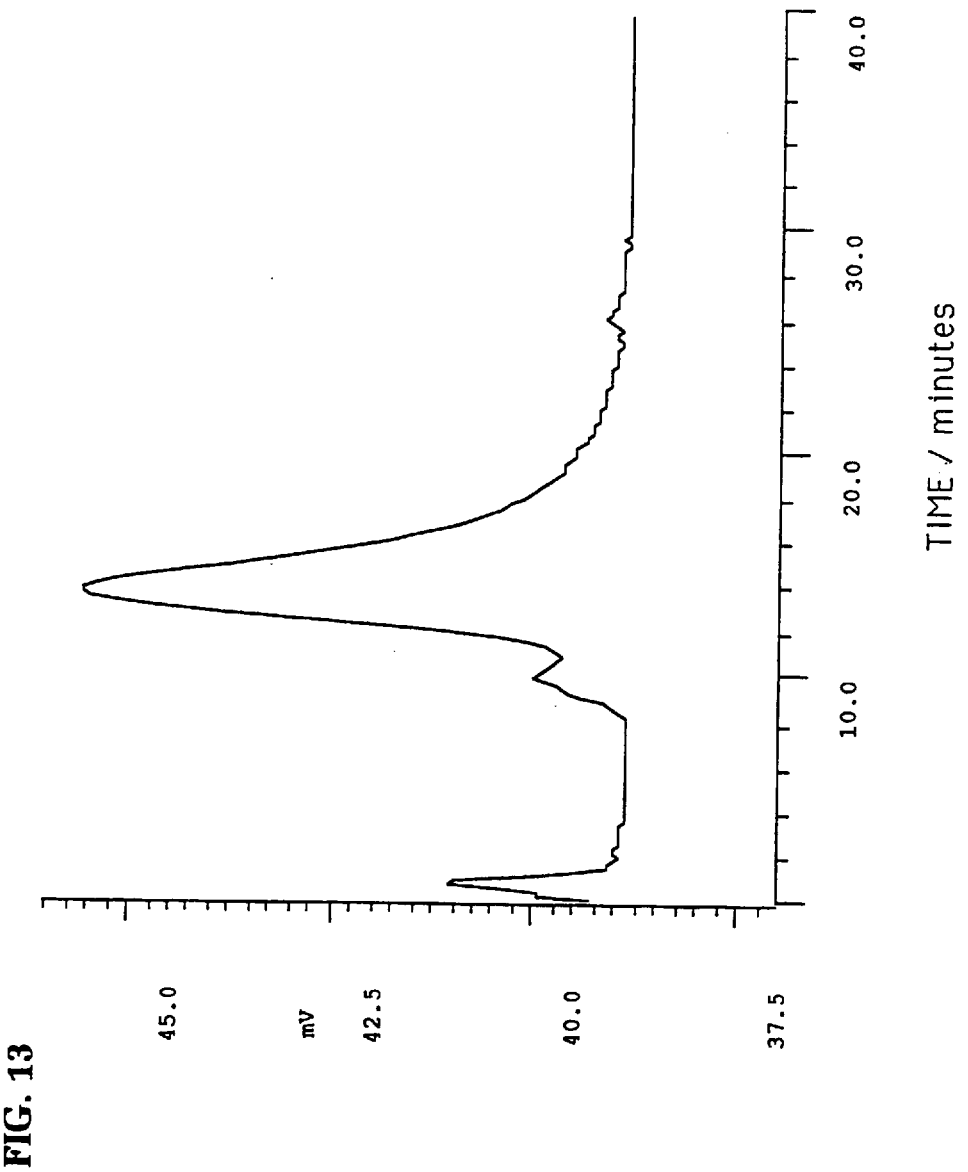
FIG. 13 shows Dextran 40 azo dye formed from dextran pyrazalone coupled to toluidine eluted on a TSK-30XL HPLC column (7.5 mm×300 mm) eluted in water at 0.5 ml/min with UV absorbance at 420 nm

Azoglycan and hydrazoglycan model derivatives were prepared from commercial dextran (of average molecular mass 40000 Da), and the methodology was identical to that outlined above, except that it was possible to isolate the glycosylhydrazine and glycosylpyrazolone intermediates by precipitation from 80% ethanol. The azoglycan and hydrazoglycan derivatives were used for size-exclusion chromatography, with detection by visible absorption (FIG. 13) and fluorescence, respectively.

II. ELIMINATION OF O-LINKED GLYCANS FROM GLYCOPROTEINS

Materials and methods

High-Performance Anion-Exchange Chromatography

High-performance anion-exchange chromatography at high pH was performed using a Waters Model 625 LC system, with a Model 464 amperometric detector operating in pulsed mode (E1=80 mV, E2=733 mV, E3=−675 mV; T1=0.400 sec, T2=0.400 sec, T3=0.200 sec). Separation was carried out with a Dionex CarboPac PA1 column (4×250 mm), with the following eluents: Monosaccharide analysis: isocratic elution at 1 ml/min with 0.015M sodium hydroxide for 20 min, followed by a 10 min wash with 0.4M sodium hydroxide (Program 1); Oligosaccharide and neuraminic acid analysis: a linear gradient of sodium acetate (0.02M to 0.25M in 0.1M sodium hydroxide over 50 min), followed by a wash with 0.4M NaOH for 10 min (Program 2) [5].

Monosaccharide Analysis

Samples were hydrolysed in 2M trifluoroacetic acid for 4 h at 100° C. The acid was removed by evaporation, the residue dissolved in water (0.100 ml), 2-deoxy-D-glucose (2 g) was added as an internal standard and aliquots (0.050 ml) analysed by high-performance anion-exchange chromatography.

Neuraminic Acid Analysis

Samples were hydrolysed in 0.1M trifluoroacetic acid for 40 min at 80° C., evaporated in a stream of nitrogen and analysed by high-performance anion-exchange chromatography.

Reversed Phase Chromatography of Hydrazones

After hydrazinolysis the mixture of protein and glycan hydrazones was dissolved in water (0.3 ml), applied to an Alltech C18 Extract Clean disposable column (500 mg) and eluted at 0.25 ml/min. Three successive fractions were collected on elution with water (10 ml), 5% aqueous acetonitrile (5 ml) and 10% aqueous acetonitrile (5 ml).

Gel Chromatography

Hydrazine-treated bovine submaxillary mucin (2–3 mg) in water (0.1 ml) was applied to a column (1.5×100 cm) of Fractogel HW-50(S) and eluted with water at 0.5 ml/min, with UV detection at 206 nm and collection of fractions (2 ml).

Desalting of Glycans by Gel Chromatography

The sample (0.2–0.5 ml) was applied to a Sephadex G-10 column (1.0×9.5 cm) and eluted with water at 0.25 ml/min, with UV detection at 206 nm and collection of fractions (0.25 ml). Fractions 16–22, which typically contained the glycans, were batched and freeze dried.

Elimination of O-Glycans

Bovine submaxillary mucin (2–3 mg) was dissolved in 50% (v/v) aqueous hydrazine hydrate (0.20 ml), with 0.1M sodium hydroxide or 0.2M triethylamine, and incubated at 45° C. for 18 h. When sodium hydroxide had been used, 0.1M hydrochloric acid (0.20 ml) was then added. The solution was dried under a stream of nitrogen and the last traces of hydrazine removed by evaporation with toluene (3×0.2 ml).

N-Acetylation of Glycan Hydrazones

Glycan hydrazones (5–50 g) were dissolved in saturated sodium hydrogen carbonate solution (0.040 ml) and acetic anhydride (2 l) added. The mixture was kept at room temperature for 20 min, with occasional mixing, and desalted by gel chromatography.

Deblocking of Glycan Hydrazones

Aqueous acetone method: Hydrazones (10–200 g) were dissolved in 20% aqueous acetone (0.2 ml) and incubated at 55° C. for 24 h. The mixture was evaporated in a stream of nitrogen, redissolved in water and freeze dried.

Copper Acetate Method: Hydrazones (10–200 g) were dissolved in copper acetate solution (1 mM, 0.5 ml) and incubated at 27° C. for 30 min. The mixture was applied to a mixed-bed ion-exchange column (0.5×5.0 cm), consisting of Chelex 100 (Na+form) and BioRad resin AG50W-X8 (H+), and eluted with water at 0.25 ml/min. The eluate (10 ml) was freeze dried.

Reduction of Glycans

Reducing oligosaccharides (25–250 g) were dissolved in 0.01M sodium hydroxide (0.04 ml) and solid sodium borohydride (2 mg) added. The mixture was kept at 4° C. overnight, acidified by dropwise addition of 1M acetic acid, freed of borate by repeated evaporation with methanol in a stream of nitrogen and desalted by gel chromatography.

RESULTS

Elimination of Glycans

Bovine submaxillary mucin was treated with 50% aqueous hydrazine and the mixture fractionated by gel chromatography. Aliquots of the eluate were hydrolysed with trifluoroacetic acid and examined by high-performance anion-exchange chromatography. Only fractions 18 to 45, corresponding to high molecular weight material, contained sugars, indicating that no significant release of sugars had taken place. Hence, in the absence of base, sugars remained attached to the protein.

When this experiment was repeated using 50% aqueous hydrazine containing 0.10M sodium hydroxide, no sugars were associated with the high molecular weight material but fractions 55 to 75, corresponding to oligosaccharides, contained glactose and galactosamine, indicating the effective release of the glycans. This experiment was repeated using 0.2M triethylamine in place of the sodium hydroxide, so that a desalting step could be avoided. The release of the glycans was equally effective.

In view of the time required for gel chromatography, the glycan-containing components were isolated by reversed-phase chromatography in subsequent experiments.

The recoveries of galactosamine in the three fractions were 72, 22 and 5%, respectively, corresponding to 99% total recovery. Fraction 1 was selected for further study, as pilot experiments had indicated that it contained all of the acidic glycans.

Conversion of Glycan Hydrazones to Reducing Glycans

Acetone Method

Figure 15A:
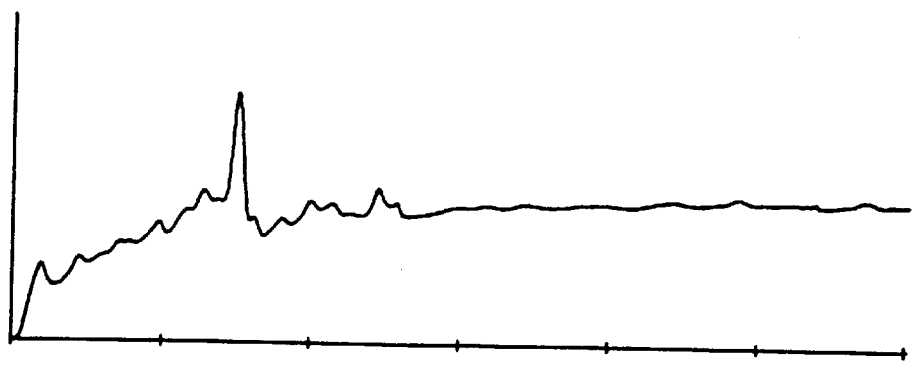
FIG. 15 shows high-performance anion-exchange chromatograms of glycans and glycan hydrazones from bovine submaxillary mucin. Panel a: hydrazones obtained by elimination in triethylamine-hydrazine; Panel b: acetone azines from treatment of hydrazones with acetone; Panel c: reducing glycans from treatment of acetohydrazones with acetone; Panel d: glycans from treatment of hydrazones with copper acetate.
Figure 15B:
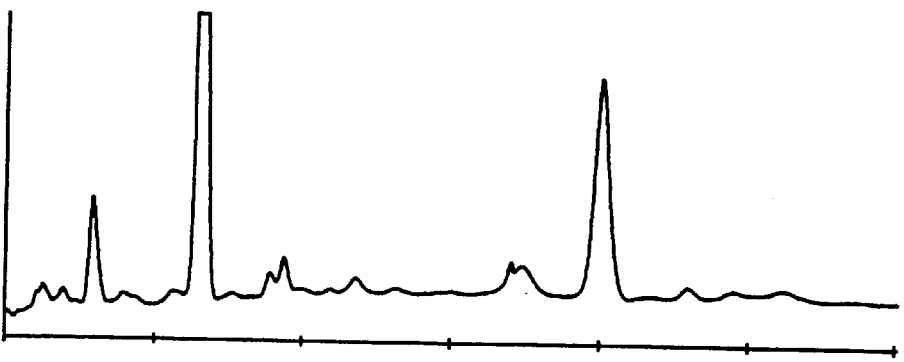
Figure 15C:
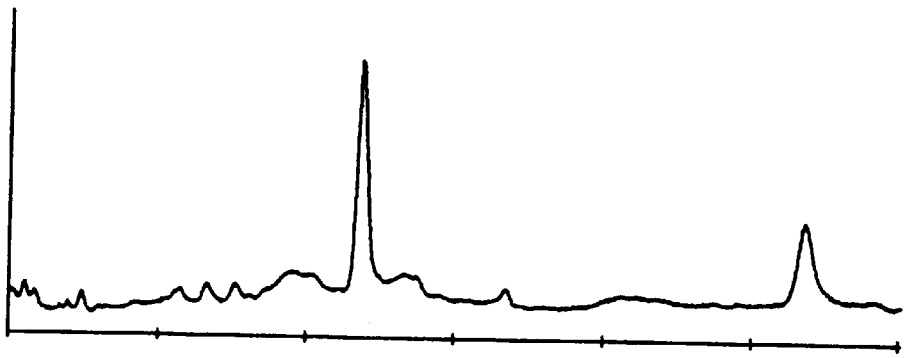
Figure 15D:
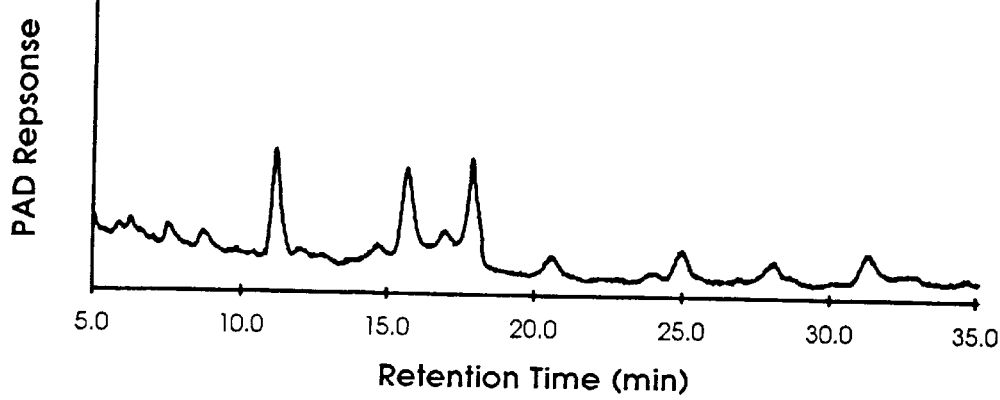
Figure 16A:
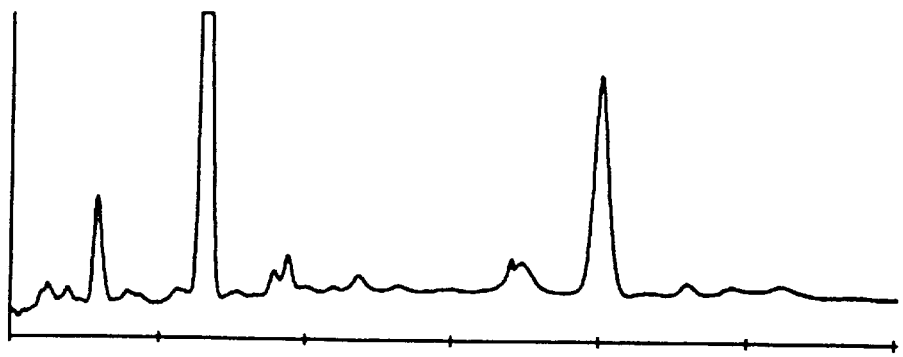
FIG. 16 shows high-performance anion-exchange chromatograms of glycan hydrazones and glycan alditols from bovine submaxillary mucin. Panel a: acetone azines from treatment of hydrazones with acetone; Panel b: acetone azines after reduction with sodium borohydride; Panel c: glycan alditols from reduction of reducing glycans; Panel d: glycan alditols from reductive elimination.
Figure 16B:
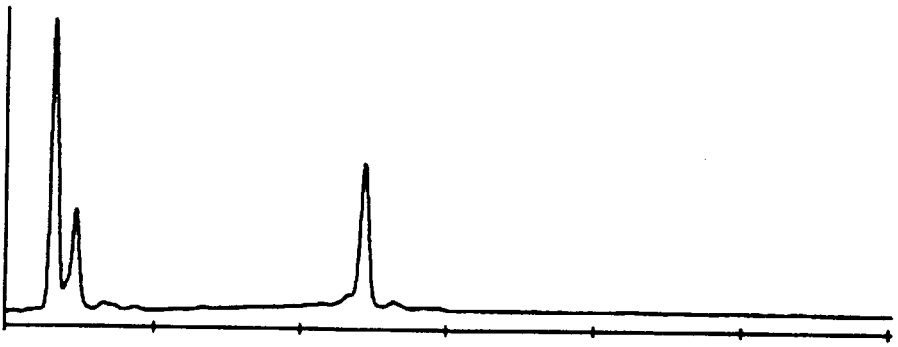
Figure 16C:
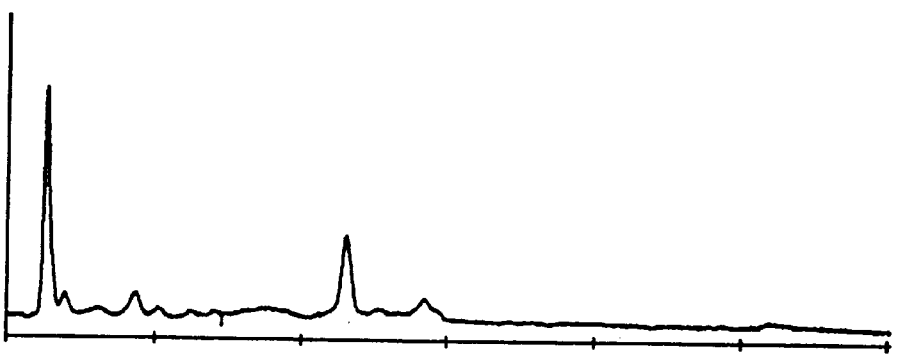
Figure 16D:
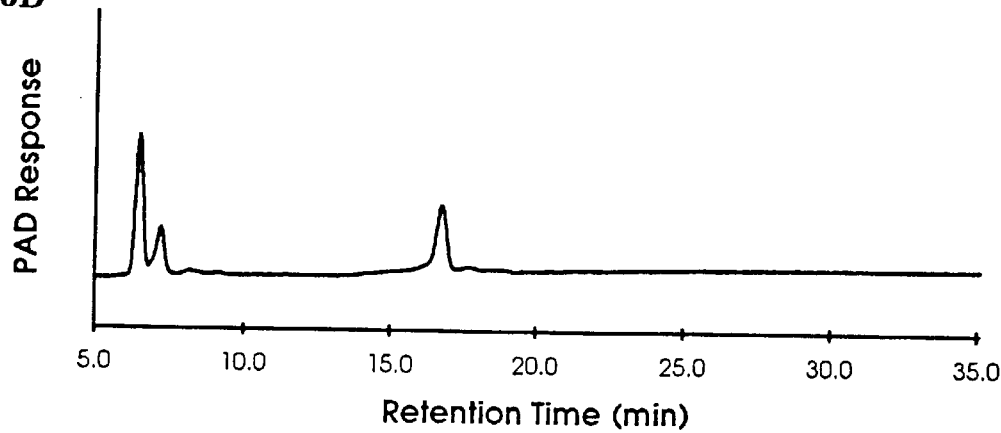

The glycosyl hydrazones were incubated in 50% aqueous acetone for 24 h at 55° C. After evaporation under reduced pressure, they were analysed by high-performance anion-exchange chromatography. The chromatogram (FIGS. 15,16) differed from that of the glycosyl hydrazones (FIG. 15a), but it was concluded that the free glycans had not been formed, as subsequent treatment with sodium borohydride produced chromatographic peaks (FIG. 16) which were not the same as those from the reductive elimination method (FIG. 16). The hydrazones were subjected to N-acetylation, followed by desalting, and once again incubated with aqueous acetone. This time, the altered chromatogram (FIG. 15) corresponded to the desired reducing glycans, as reduction with borohydride gave a chromatogram (FIG. 16) which corresponds to that obtained after reductive elimination (FIG. 16). The slight quantitative differences between these chromatograms are attributed to differences in the fractionation of the glycans in the reversed-phase separation of the glycan hydrazones.

The two groups of peaks at approx. 7 and 17 min (FIG. 16) correspond to acidic glycans containing N-acetylneuraminic acid and N-glycolylneuraminic acid, respectively. Assuming equal response factors for the glycans, glycans containing these acids are esimated to be present in the ratio of 1.98:1. The ratio of the neuraminic acids obtained by mild hydrolysis of the starting glycoprotein was 1.48:1.

Copper Acetate Method

When the glycan hydrazones were treated with copper acetate, followed by cation-exchange chromatography, the product mixture was complicated and contained the expected reducing glycans in disappointing yield, because of incomplete removal of the hydrazone groups and the associated loss of the basic hydrazones on the column (FIG. 16). When the hydrazones were N-acetylated and desalted before the copper acetate treatment, the glycans were obtained in good yield.

The standard procedure for the release of O-glycans from a glycoprotein involves the digestion of a glycoprotein with dilute alkali. The glycans are eliminated as reducing sugars, which are unstable in the alkali, and sodium borohydride is added in high concentration to convert them to the stable alditols before degradation occurs. The inclusion of the borohydride, however, is somewhat problematic, as it leads to significant release of N-linked glycans and some fragmentation of the protein chain [12, 13]. Tritium label is often added at this stage [4], using labelled borohydride, but its incorporation is inherently inefficient because of the high molarity of reducing agent which is required (typically $0.8^{-1}M$).

Both O- and N-linked glycans are released from glycoproteins by heating with anhydrous hydrazine at 95° C. or above [5], but the O-linked glycans can be released selectively by using milder conditions [5]. The release of the N-glycans results from the hydrazinolysis of the amide linkages of asparagine, but the removal of the O-glycans probably involves a beta-elimination process, promoted by the basicity of the hydrazine and analogous to that which occurs in aqueous alkali. An important advantage of using hydrazine is that, as the sugars are released, they are converted to the hydrazones and protected from degradation under the basic conditions.

It seemed possible that aqueous hydrazine might be sufficiently basic to promote beta-elimination, and that the glycans might be converted to the base-stable hydrazones as they are released. In exploratory experiments, the inventors observed no release of glycans from bovine mucin after extended incubation in 50% aqueous hydrazine, but the addition of 0.1M sodium hydroxide to the hydrazine led to smooth release of the O-glycans. After neutralisation of the alkali, the sample was fractionated by gel or reversed-phase chromatography. It was necessary to desalt the sugar-containing fractions by gel chromatography before analysis by high-performance anion-exchange chromatography. An improvement to the method used a volatile organic base, triethylamine, instead of sodium hydroxide. The elimination was equally effective, but a desalting step was no longer required.

Figure 17:
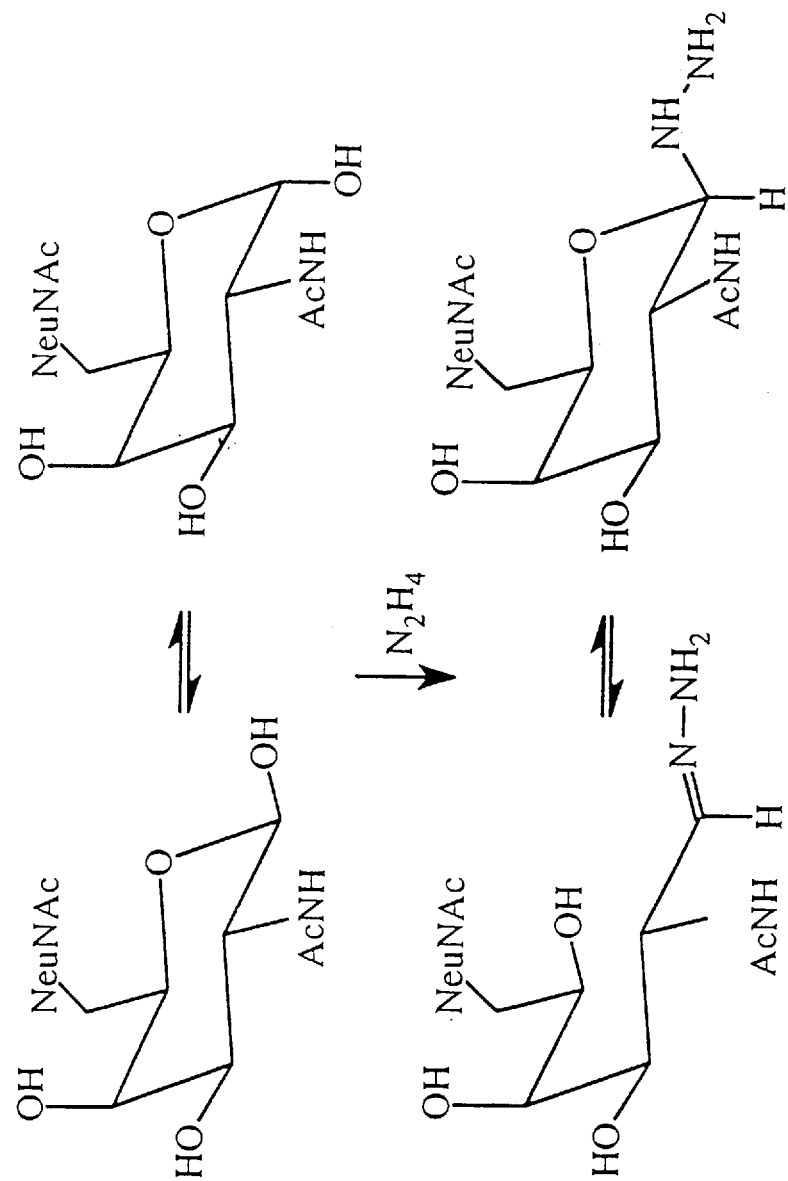
FIG. 17 shows hydrazone chemistry of a typical O-glycan. The equilibrium between the sugar hydrazone and hydrazine is also indicated.

For the complete success of any method which uses hydrazine for the release of glycans, it is essential to have available a method for regenerating the reducing glycans from the hydrazones. Sugar hydrazones are somewhat resistant to acidic hydrolysis, but can be hydrolysed to the parent glycans under mildly acidic conditions [14] if they are first converted to the acetohydrazones (FIG. 17). A disadvantage of such an acidic treatment is the concomitant loss of a small proportion of the labile neuraminic acid residues [15]. It is suspected that it might be possible to achieve deblocking of the hydrazones more conveniently and safely under neutral conditions, by employing ketone exchange of the hydrazine component with an excess of acetone. Accordingly, the mucin hydrazones were incubated with aqueous acetone. A change was observed in the chromatographic profile (compare FIG. 15), but this did not correspond to conversion to the reducing glycans, and probably indicates the conversion of the hydrazones to the acetone azines (FIG. 17). When the hydrazones were N-acetylated to the acetohydrazones (FIG. 17) before the treatment with acetone, however, complete conversion to the reducing glycans was observed (FIG. 15). On reduction, these were converted to the glycan alditols (FIG. 16c) which corresponded to the products of the standard reductive elimination method (FIG. 16).

Another mild procedure for the deblocking of glycan hydrazones [5] involves a brief treatment with copper acetate, followed by removal of cations on a mixed-bed cation-exchange column. When the inventors applied the method to the mucin hydrazones, the yield of reducing glycans was low (FIG. 15). After conversion to the acetohydrazones, however, the yield of deblocked glycans was almost as high as with the acetone method. An N-acetylation step is a recognised part of the published protocol using anhydrous hydrazine [4, 5], because of the complete loss of the N-acyl substituents in the hydrazine. Although some of the observed losses can be attributed to the loss of N-acyl substituents during the elimination, it appears that prior conversion of the hydrazones to the acetohydrazones is important to the success of the deblocking using copper acetate.

It should be noted that the classical procedure [4] for the isolation of N-glycans after hydrazinolysis does not include a specific step for the deblocking of the hydrazone groups. It does, however, require an extended preparative paper chromatography fractionation step, designed to remove the amino acid hydrazides. The time spent in such an aqueous environment probably also achieves a significant degree of hydrolysis of the hydrazones, which would explain why the step is essential for the effective incorporation of tritium label [4].

In common with the sodium hydroxide-sodium borohydride procedure, the glycans were isolated with the N-acyl groups intact. Two classes of acidic glycans were obtained: those containing N-acetylneuraminic. acid, which eluted first using high-performance anion-exchange chromatography, and those containing N-glycolylneuraminic acid, which are more retained (FIG. 16). The two classes were present in the ratio of 1.98:1, whereas the corresponding neuraminic acids in the starting glycoprotein were in the ratio of 1.48:1. A proportion of the N-acyl substituents had therefore been released under the elimination conditions, representing a loss of important structural information. This loss is complete when anhydrous hydrazine is used [4, 5].

III. BINDING OF CARBOHYDRATES TO SOLID SUPPORTS I: AS THIOSEMICARBAZONES

MATERIALS AND METHODS

Kinetics of Formation of Sugar Hydrazones in Hydrazine Hydrate

Glucose or N-acetylglucosamine (10 mg) was dissolved in 100% or 25% hydrazine hydrate (400 µl) and allowed to stand at room temperature for up to 6 h. The reagent was removed in a stream of dry nitrogen and the product dissolved in deuterium oxide for $^1$H nmr spectroscopy. The degree of conversion to the hydrazones and loss of N-acetyl groups were determined by comparison of the resonances (Table 1) corresponding to H-1 and the N-acetyl groups of N-acetylglucosamine, N-acetylglucosamine hydrazone and acetohydrazide.

TABLE 1

Nmr reporter resonances for analysis of sugar derivatives in deuterium oxide.

| Compound | Resonance | Assignment |
|---|---|---|
| glucose | 5.21 (d, J = 3.8) | H-1 α-pyranoside |
|  | 4.62 (d, J = 7.9) | H-1 β-pyranoside |
| N-acetylglucosamine | 5.19 (d, J = 3.4) | H-1 α-pyranoside |
|  | 4.70 (d, J = 8.4) | H-1 β-pyranoside |
| glucose hydrazone | 4.06 (d, J = 9.0) | H-1 β-pyranoside |
|  | 7.27 (d, J = 6.5) | H-1 open-chain E-isomer |
|  | 6.70 (d, J = 6.5) | H-1 open-chain Z-isomer |
| N-acetylglucosamine hydrazone | 2.03 and 2.04 (s, 3H) | N-acetyl |
|  | 4.08 (d, J = 9.6) | H-1 β-pyranoside |
|  | 7.24 (d, J = 5.3) | H-1 open-chain E-isomer |
|  | 6.55 (d, J = 7.4) | H-1 open-chain Z-isomer |
| acetohydrazide | 1.94 (s, 3H) | N-acetyl |
| 4-tolylthiosemicarbazide | 2.33 (s, 3H) | methyl |
|  | 7.26 (s, 4H) | aromatics |
| glucose | 2.35 (s, 3H) | methyl |
| 4-tolylthiosemicarbazone | 4.17 (d, 1H, J = 8.8) | H-1 b = 15-pyranoside |
|  | 7.26 (s, 4H) | aromatics |

Preparation of Labelled Sugar Hydrazones

A solution of $^{14}$C-glucose (approx 20 nmol) in 70% aqueous ethanol (0.10 ml) was evaporated to dryness in a 1.5 ml plastic centrifuge tube. The residue was dissolved in hydrazine hydrate (0.025 ml) and allowed to stand at room temperature for 30 min before evaporation in a vacuum desiccator containing concentrated sulfuric acid. The evaporation was complete after 2 h. To ensure effective removal of hydrazine, the residue was twice dissolved in water (0.050 ml) and re-evaporated. $^{14}$C N-acetylglucosamine was treated in the same way with 25% aqueous hydrazine hydrate for 6 h before evaporation. The sugar hydrazones were stored dry in the freezer for up to 2 months.

Preparation of 4-Tolylthiosemicarbazide

Tolyl isothiocyanate was prepared from 4-toluidine (10.7 g, 0.1 mol) as described [16] and dissolved in chloroform (75 ml). Hydrazine hydrate (50 ml, 1 mol) was added, followed by ethanol (50 ml) to form a homogeneous solution and the solution allowed to stand for 30 min. The white crystals were collected by filtration and crystallised from ethanol. The yield was 9.1 g (50%), m.p. 133°–134°.

Preparation of Glucose 4-Tolylthiosemicarbazone

Glucose (1 g, 5.56 mmol) and 4-tolylthiosemicarbazide (1 g, 5.52 mmol) were mixed with ethanol-water (1:1, 40 ml) and acetic acid (0.50 ml) to form a cloudy solution [14], which was refluxed for 1 h and left standing overnight at room temperature. A small amount of insoluble material was removed by filtration and the filtrate evaporated to give a foam (2.1 g), which was purified by flash chromatography on a silicic acid column. Unreacted 4-tolylthiosemicarbazide eluted with ethyl acetate and glucose 4-tolylthiosemicarbazone with ethanol:ethyl acetate (1:9). The yield was 0.80 g (40%).

Stability Preparation of Glucose 4-Tolythiosemicarbazone

A solution of glucose 4-tolylthiosemicarbazone (10 mg, 30 mmol) in D$_2$O (0.5 ml) was kept at 27° C. and its $^1$H-nmr spectrum measured at intervals over a period of 14 days. The solution was subsequently heated at 80° for 4 h and the spectrum again measured. The absence of glucose was judged by the lack of H-1 resonances (Table 1). Nmr studies of the stability of N-acetylglucosamine 4-tolylthiosemicarbazone in aqueous solution were not carried out because of its poor solubility in water.

Kinetics of Formation of Glucose 4-Tolylthiosemicarbazone

Glucose (1.53 mg, 8.5 mol) and 4-tolylthiosemicarbazide (1.54 mg, 8.5 mol) were dissolved in a 50 mM solution of potassium dihydrogen phosphate in $D_2O$ (0.5 ml, apparent pH 4.6) and maintained in an nmr tube at 80° for 16 h. $^1$H-nmr spectra were measured at intervals and the reporter groups (Table 1) for glucose, 4-tolylthiosemicarbazide and glucose 4-tolylthiosemicarbazone used to determine the course of the reaction.

Derivatisation of Polystyrene Beads

Aminopolystyrene beads were prepared as before [9] in batches of 500 beads and stored in 0.1M hydrochloric acid at 4°. They typically had 750–800 nmol amino groups per bead, as assessed by reaction with 4-nitrobenzaldehyde [9].

Isothiocyanatopolystyrene beads were obtained by washing batches of 50 aminopolystyrene beads with water and ethanol, adding them to a solution of thiophosgene (20 µl, 0.26 mmol) in ethanol (1.25 ml) and agitating gently for 2 h. They were then collected by filtration and washed several times with ethanol to remove all traces of excess reagent. The level of residual amino groups was determined by the 4-nitrobenzaldehyde method [4] and the difference between this level and that of the initial amino beads was taken to be the level of conversion to isothiocyanato groups. Commercial alkylamino beads were treated in the same way.

Thiosemicarbazido beads were prepared in batches from 50 isothiocyanatopolystyrene beads by washing with ethanol and agitating gently in a solution of hydrazine hydrate in ethanol (5%, 5 ml) for 30 min. The beads were collected by filtration, washed with ethanol and stored in 0.01M hydrochloric acid at 4° C.

Binding of Sugar Hydrazones to Isothiocyanatopolystyrene Beads

Before binding, the isothiocyanatopolystyrene beads were equilibrated with phosphate buffer (0.2M) of the same pH as was used for subsequent binding for 15 min and drained. In a typical experiment, duplicate sets of 3 beads were added to a solution of $^{14}$C glucose hydrazone (2 nmol) or $^{14}$C N-acetylglucosamine hydrazone (0.1 nmol) in buffer (200 µl) and agitated gently for the requisite time. Aliquots (2×50 µl) of the supernatants were taken for radiochemical counting. Binding was evaluated in buffers of different pH for 1 h and a detailed time course determined at pH 8.0.

Removal and Recovery of Bound Sugars from Isothiocyanatopolystyrene Beads

To establish the stability of binding of sugars at different pH values, 3 beads were added to 0.20 ml of specified buffer and agitated gently for 2 h. All experiments were performed in duplicate in sealed tubes and aliquots (2×0.050 ml) of supernatant were taken for radiochemical counting. To determine the efficiency of recovery of the sugars, the beads were exposed in the same way to 200 µl of 100% or 25% hydrazine hydrate, and aliquots of supernatants counted as before. More forcing conditions employed hydrazine hydrate, ethanolic benzaldehyde and aqueous acetone at higher temperatures.

Binding to Alkyl Isothiocyanato Beads

Before binding, the alkyl isothiocyanato beads were equilibrated with phosphate buffer (0.2M) for 15 min and drained. One bead was added to a tube containing a solution of $^{14}$C-N-acetylglucosamine hydrazone (0.5 nmol) in the same buffer (250 µl) and agitated gently for 1 h. Duplicate experiments were carried out and aliquots (2×50 µl) were taken for radiochemical counting.

RESULTS

Hydrolysis of Glucose 4-Tolylthiosemicarbazone

The $^1$H nmr spectrum of an aqueous solution of glucose 4-tolylthiosemicarbazone did not change after 14 days at 27° C. and subsequent heating at 80° C. for 4 h, indicating that no hydrolysis had taken place.

Kinetics of Formation of Glucose 4-Tolylthiosemicarbazone

The kinetic study of the reaction between glucose and 4-tolylthiosemicarbazide in deuterium oxide produced a straight-line plot using the linear form of the rate equation expected for an A+B=Z reaction approaching equilibrium. The equilibrium constant for the formation of the product was $38M^{-1}$. Assuming that the effective concentration of immobilized thiosemicarbazido groups is equivalent to that in a homogeneous solution containing the same total number of groups, a loading of 0.6 mmol of groups per bead would lead to 34% binding of glucose using 3 beads and 200 µl of buffer.

Derivatization of Polystyrene Beads

Polystyrene beads were nitrated and reduced as before [9]. Ethanol was a satisfactory solvent for the conversion to the isothiocyanate. Dioxan and tetrahydrofuran were evaluated, but they caused unacceptable softening of the beads.

When the amino content of beads was determined using 4-nitrobenzaldehyde [9], before and after treatment with thiophosgene, about 25% of the amino groups were still present after the reaction. The decrease in the level of amino groups was taken as a measure of the isothiocyanato loading (approximately 600 nmol/bead).

Binding of Reducing Sugars to Thiosemicarbazido Beads

The binding of glucose and N-acetylglucosamine to thiosemicarbazido beads was evaluated after heating under conditions similar to those used with amino beads [9], but the efficiency of uptake (Table 2) was poor. Moreover, only a low proportion of the bound sugars was removed by hydrazine, suggesting that the binding that had occurred was due mainly to Amadori attachment to the amino groups still present on the beads.

TABLE 2

| Direct binding [1] of $^{14}$C-glucose to thiosemicarbazido- and aminopolystyrene beads and its recovery[2] with hydrazine hydrate | | | |
|---|---|---|---|
| Thiosemicarbazidopolystyrene | | Aminopolystyrene | |
| bound (%) | recovery (%) | bound (%) | recovery (%) |
| 48 | 6 | 90 | 1 |
| 46 | 4 | 91 | 0 |

[1]0.2M sodium phosphate buffer pH 3, 100° C., 2 h.
[2]100% hydrazine hydrate, room temperature, 16 h.

Binding of Sugar Hydrazones to Isothiocyanato Beads

Glucose and N-acetylglucosamine were treated in 100% hydrazine hydrate at room temperature for various times, then evaporated under reduced pressure. The conversion to the hydrazones was complete after treatment for 30 min, but 21% of the N-acetyl groups were lost from the N-acetylglucosamine hydrazone. In 25% hydrazine hydrate, coversion to the hydrazones required treatment for 6 h, but the loss of N-acetyl group's was only 10%. As a general procedure, therefore, labelled N-acetylglucosamine was treated with 25% hydrazine hydrate for 6 h. The unpurified products were used to bind to isothiocyanato beads and no attempt was made to determine the yield of the hydrazones, but the high overall efficiency of immobilization of the sugars (Tables 3, 4) was consistent with a good conversion.

Binding of glucose and N-acetylglucosamine hydrazones at room temperature was optimal at a pH of 7–9 (Table 3).

Time course experiments (Table 4) at pH 8 showed 76% binding of glucose hydrazone and 83% binding of N-acetylglucosamine hydrazone after 24 h.

The binding to alkylisothiocyanato beads (Table 3) was inferior to that of the aryl isothiocyanato beads and was most efficient at low pH.

TABLE 3

Binding[1] of sugar hydrazones to isothiocyante- substituted beads as a function of pH

| pH | Glucose hydrazone (%) | N-Acetylglucosamine hydrazone (%)[2] | N-Acetylglucosamine hydrazone (%)[3] |
|---|---|---|---|
| 4 | nd[4] | nd[4] | 18 |
| 5 | 12 | 12 | 14 |
| 6 | 23 | 27 | 6 |
| 7 | 30 | 34 | 8 |
| 8 | 29 | 36 | 5 |
| 9 | 29 | 38 | 7 |

[1]0.2M sodium phosphate buffer, room temperature, 1 h.
[2]Isothiocyanatopolystyrene beads.
[3]Isothiocyanatoalkyl beads.
[4]not determined.

TABLE 4

Time course of binding of sugar hydrazones to isothiocyanatopolystyrene beads[1]

| Time (h) | Glucose hydrazone (%) | N-Acetylglucosamine hydrazone (%) |
|---|---|---|
| 0.5 | 16 | 20 |
| 1 | 29 | 34 |
| 2 | 40 | 48 |
| 4 | 54 | 81 |
| 8 | 72 | 71 |
| 24 | 76 | 83 |

[1]0.2M sodium phosphate buffer pH 8.0, room temperature.

Stability of Binding and Recovery of Bound Sugars

The attachment of the sugars was stable in buffers of pH 5–7.4 (Table 5). When the beads were treated with hydrazine hydrate at room temperature, there was a modest recovery of the sugar hydrazones (Table 6), but heating (Table 7) removed most of the bound sugars. These results suggest that there are more than one population of bound sugars, and that only some of them are released under mild conditions. Alternatively, the immobilized sugar hydrazones were treated with a solution of benzaldehyde or acetone at 100° C. (Table 7). Similar levels of recovery of the sugars were obtained.

TABLE 5

Loss of sugars bound as thiosemicarbazones to isothiocyanatopolystyrene beads on standing in aqueous buffers[1]

| Reagent | [14]C glucose (%) | [14]C N-acetyl glucosamine (%) |
|---|---|---|
| pH 2.2 citrate/phosphate | 11 | 6 |
| pH 3.0 citrate/phosphate | 6 | 6 |
| pH 4.0 citrate/phosphate | 4 | 4 |
| pH 5.0 phosphate | 3 | 1 |
| pH 6.0 phosphate | 1 | 0.6 |
| pH 7.0 phosphate | 0.5 | 0.3 |
| pH 7.4 phosphate-buffered saline | 0.7 | 0.7 |

[1]At room temperature, 2 h.

TABLE 6

Recovery at room temperature of sugars bound as thiosemicarbazones to isothiocyanatopolystyrene beads

| | Glucose removed (%) | | N-acetylglucosamine removed (%) | |
|---|---|---|---|---|
| Time (h) | 25% hydrazine hydrate | 100% hydrazine hydrate | 25% hydrazine hydrate | 100% hydrazine hydrate |
| 1 | 28 | 55 | 19 | 35 |
| 2 | 36 | 50 | 27 | 46 |
| 4 | 40 | 57 | 33 | 45 |
| 8 | 50 | 57 | 37 | 40 |
| 16 | 52 | 59 | 43 | 47 |

TABLE 7

Recovery under forcing conditions of sugars bound as thiosemicarbazones to isothiocyanatopolystyrene beads

| Bound sugar | hydrazone hydrate[1] 2 h | hydrazine hydrate[1] 24 h | benzaldehyde[2] 2 h | acetone[3] 2 h |
|---|---|---|---|---|
| glucose | 94 | 94 | 53 | 47 |
| N-acetyl-glucosamine | 81 | 96 | 67 | 45 |

[1]100% hydrazine hydrate at 50° C.
[2]25% benzaldehyde in 95% ethanol at 100° C.
[3]25% acetone in water at 100° C.

Figure 18:
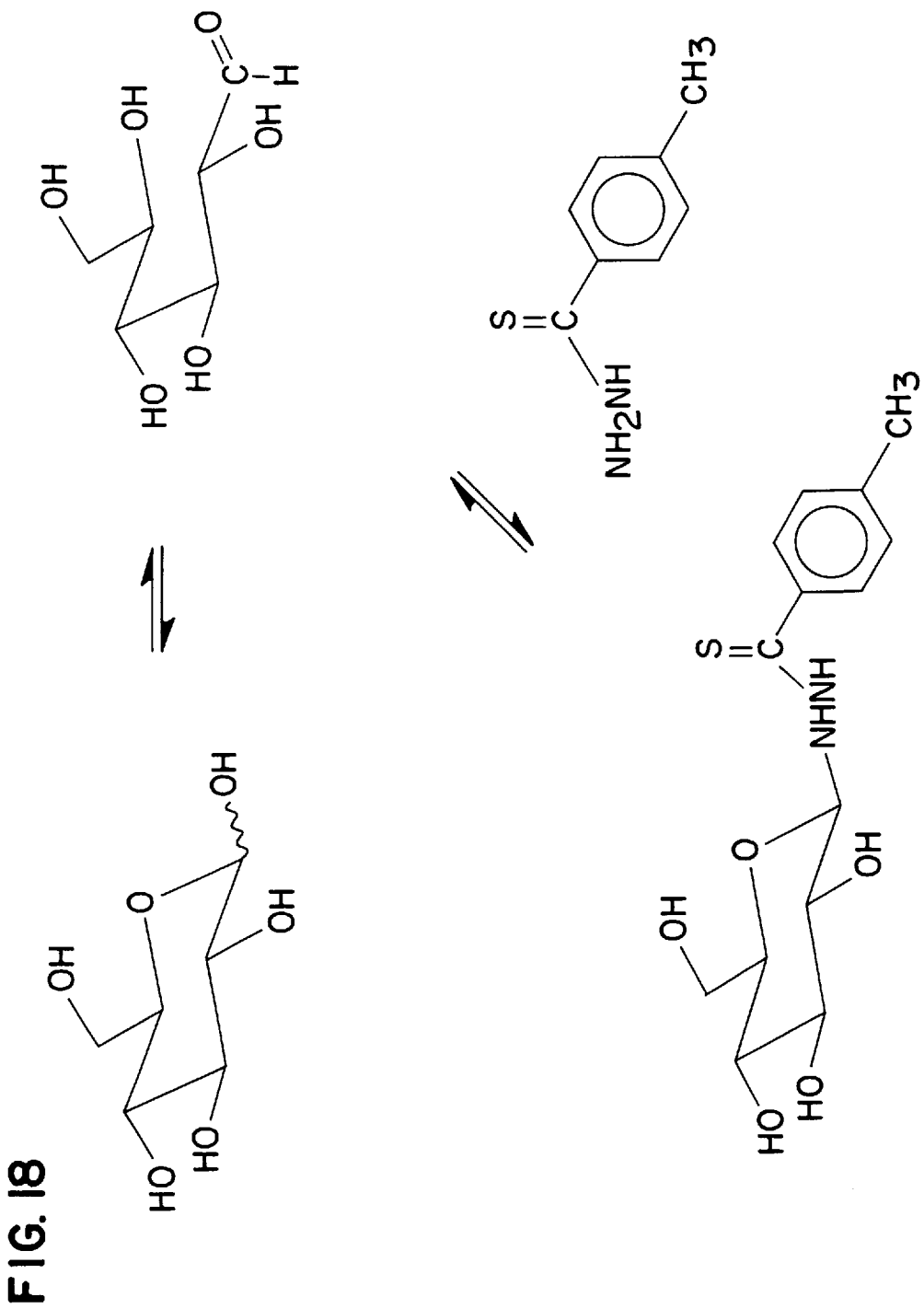
FIG. 18 shows direct formation of glucose 4-tolylthiosemicarbazone by condensation of N-glucose with 4-tolythiosemicarbazide.

Thiosemicarbazones have been prepared in good yield by condensation of reducing sugars with thiosemicarbazides [17]. In general, aldose hydrazones exist in aqueous solution primary in ring forms [18], especially the β-glycopyranosylhydrazines, but no information is available about their thermodynamic stability. The formation constant of a model compound, glucose 4-tolylthiosemicarbazone (FIG. 18), was determined by $^1$H nmr. Its low value (38$M^{-1}$) suggested that efficient binding of a sugar to thiosemicarbazide groups immobilised on a solid support would require relatively high concentrations of the functional groups on the support. Consistent with this, the direct binding of reducing sugars to thiosemicarbazido beads was poor (Table 2). Despite its modest thermodynamic stability, however, the good kinetic stability of glucose 4-tolylthiosemicarbazone on heating in unbuffered D20 suggested that the thiosemicarbazone linkage might still be suitable for immobilisation of sugars.

Figure 19:
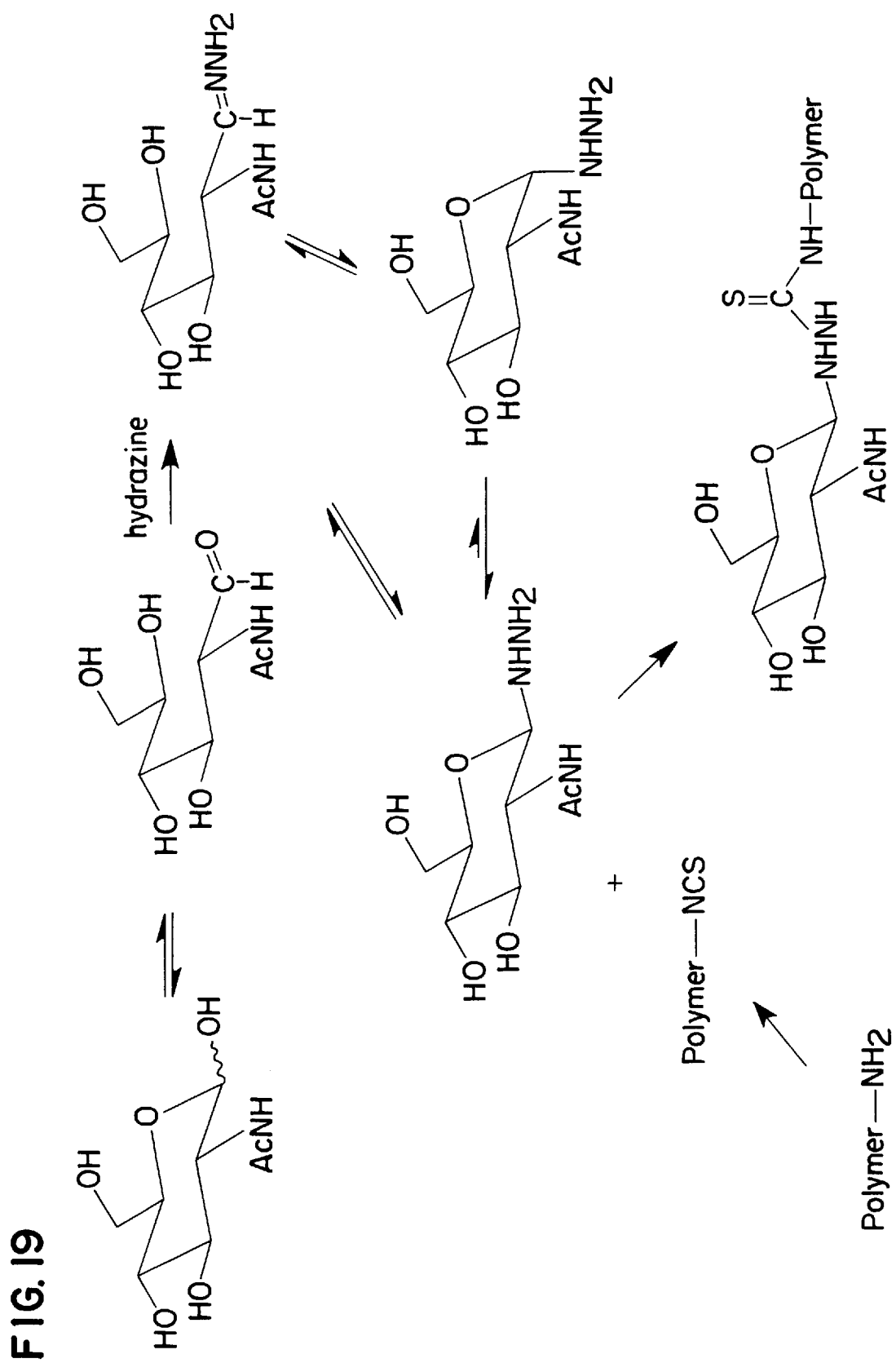
FIG. 19 shows formation of N-acetylglucosamine hydrazone and its reaction with an isothiocyanate-derivatived polymer to give the immobilized N-acetylglucosamine thiosemicarbazone.

An alternative method of immobilisation, employing reaction of preformed sugar hydrazones with isothiocyanato beads (FIG. 19) at room temperature, achieved good immobilisation within a few hours (Table 4). Model experiments were undertaken to determine the conditions required for efficient hydrazone formation. Glucose and N-acetylglucosamine were treated with 25% and 100% hydrazine hydrate for up to 6 h and the products examined by $^1$H nmr spectrometry. Both sugars were converted quantitatively to their hydrazones after 30 min (in 100% hydrazine hydrate) or 6 h (in 25% hydrazine hydrate).

There was a concomitant loss of N-acetyl groups from N-acetylglucosamine, which amounted to some 21% or 10%, respectively. Both hydrazone formation and deacetylation have first-order kinetics with respect to the sugar and these observations can be extrapolated to the nanomolar amounts of labelled sugars used in binding experiments.

Optimal binding of hydrazones to isothiocyanatopolystyrene beads occured in the pH range of 7–9 (Table 3), consistent with the requirement that the sugar hydrazones be deprotonated to enable nucleophilic attack on the isothiocyanates. The attached sugars were stable at room temperature under neutral conditions (Table 5), but hydrolysed slowly at pH 5 and below. Their stability under alkaline conditions was not tested.

Figure 20:
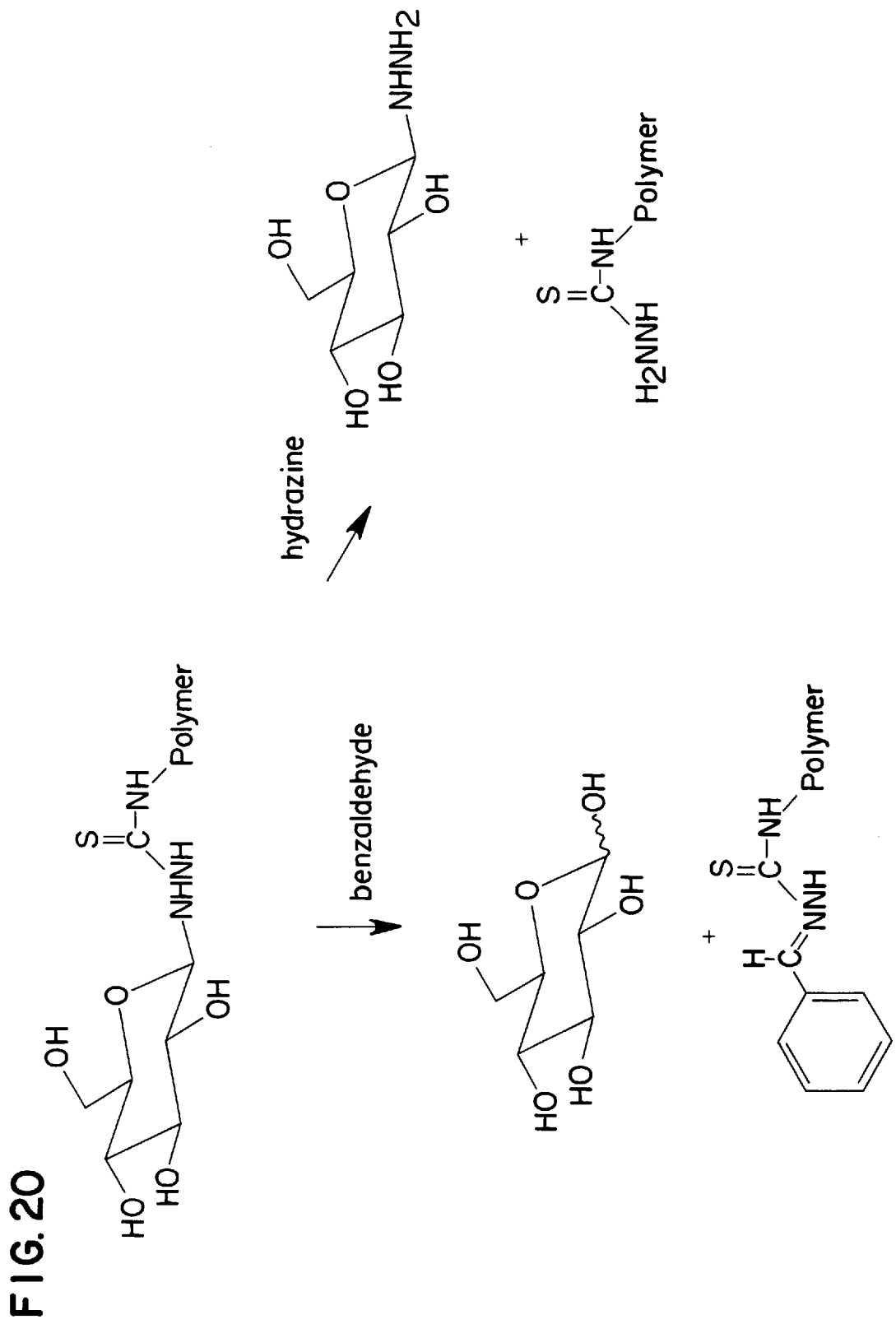
FIG. 20 shows liberation of immobilised glucose thiosemicarbazone by treatment with hydrazine to liberate glucose hydrazone and with benzaldehyde to form free glucose.

An advantage of this method of coupling is that it is possible to release the sugars using nucleophilic conditions (FIG. 20). Up to 59% recoveries of $^{14}C$ glucose, and 47% of $^{14}C$ N-acetylglucosamine, as the hydrazones, were obtained by treating the beads with hydrazine hydrate at room temperature (Table 6). Almost complete recovery (Table 7) was obtained at 100° C., but with the disadvantage that any N-acyl groups are lost. Cleavage under electrophilic conditions, by exchange onto an excess of benzaldehyde or acetone gave somewhat lower recoveries, but has the advantages that the free sugars are liberated (FIG. 20), rather than the hydrazones, and that there is no loss of N-acyl substituents.

Alkylaminopolystyrene beads are commercially available, and it was of interest to establish whether they are amendable to the binding of sugars by this isothiocyanate chemistry. In the event, the approach was only marginally successful (Table 3). Aliphatic isothiocyanate groups are less reactive to nucleophiles than their aromatic counterparts [19], which explains the more sluggish kinetics of coupling with the sugar hydrazones. The ehancement of coupling at low pH is indicative of acid catalysis, which may be exploited in some situations.

The present chemistry for the immobilisation of sugars as aryl thiosemicarbazones is similar to that in use for the covalent attachment of proteins for N-terminal analysis [20], whereby immobilised isothiocyanato groups are reacted with nucleophilic E-amino groups of lysine side chains. Isothiocyanate-substituted sugar derivatives have been employed [21] in the attachment of sugars to protein amino groups. With this strategy, however, the reactive ligand must be purified before coupling to the polymer, which is less convenient than the present approach.

The attachment of preformed sugar hydrazones to immobilized isothiocyanato groups represents a useful advance over other methods, in that it provides experimental simplicity, good binding under mild conditions and a reasonable level of recoverability. It is compatible with the presence of acid-labile sugar linkages, and retains the desirable structural characteristics [22–25] of a reducing terminal sugar in the β-pyranose ring form and a spacer arm between the polymer support and ligand. It therefore promises to be suitable for a number of solid-phase chemical and biochemical techniques, such as methylation analysis, sequencing [26] and stuctural modification [27].

IV. BINDING OF CARBOHYDRATES TO SOLID SUPPORTS II: BY AMADORI REARRANGEMENT

Nitration of Polystyrene Beads

Polystyrene beads (20 g) were added with stirring to a mixture of nitric acid (70%, 25 ml) and sulfuric acid (98%, 30 ml) which had been cooled to 5° C. in an ice bath. Stirring was continued at 5° C. for 4 h. The supernatant was poured off and the cream-colored beads washed well with water and dried.

Reduction of Nitropolystyrene Beads

Stannous chloride dihydrate (15 g) in hydrochloric acid (20 ml) was heated with stirring at 90° C. in an oil bath until dissolved. Nitropolystyrene beads (20 g) were added and stirring continued for 2 h at 90° C. The supernatant was poured off, and the beads washed several times with hot water, then twice with 1M NaOH (to break up any chlorostannate salt) then with water and 1M HCl. The beads were stored at 4° C. under 1M hydrochloric acid.

Estimation of the Degree of Derivatisation of Beads

The beads were shaken for 30 min in 5% sodium hydrogen carbonate solution and washed 3 times with water and then with ethanol. Four beads were added to each of a series of tubes, 1 ml of an ethanolic solution of 4-nitrobenzaldehyde (4 mM) in acetic acid (1%) added to each, the tubes capped and shaken gently at room temperature for up to 16 h. Aliquots (200 µl) were diluted to 3 ml with ethanol and the absorbance at 275 nm compared with that of the original aldehyde solution.

Binding of Sugars to Aminopolystyrene Beads (a) General

Figure 21:
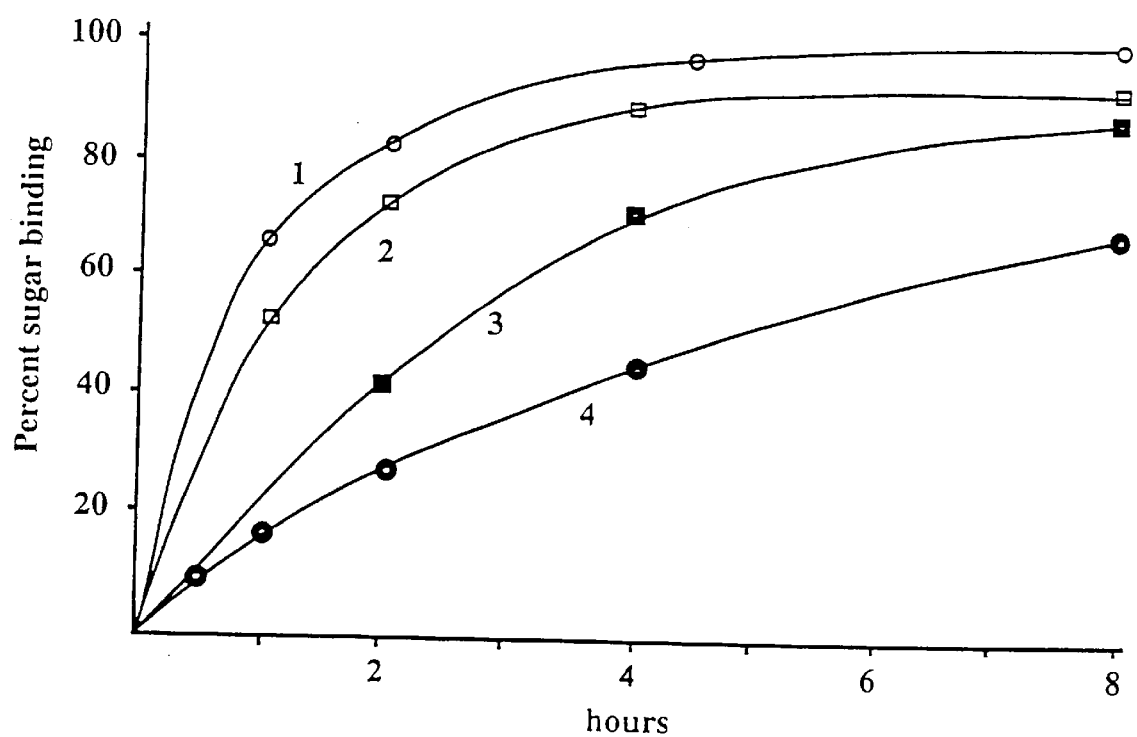
FIG. 21 shows binding of reducing sugars to aminopolystyrene as a function of time. Curve 1: $^{14}C$-glucose (approx. 100 nM) in phosphate buffer (0.1M, pH 4.3) at 100° C.; curve 2: 1 mM maltose in water at 100°, analysed by the phenol-sulfuric acid test; curve 3: 1 mM N-acetylglucosamine in water at 100° C., analysed by the Morgan-Elson test; curve 4: $^{14}$C-glucose (approx. 100 nM) in water at 75° C.

The aminopolystyrene beads were equilibrated with buffer for 1 h or washed well with water before use. In a general procedure, four aminopolystyrene beads were added to a 10 mm capped glass tube and incubated with 300 µl of a sugar solution. The binding of sugars was assessed by determining the amount of sugar remaining in the supernatant. Binding was studied as a function of time and temperature (FIG. 21). In all experiments, blanks were included to determine non-specific binding to beads and glassware.

(b) Radiochemical Analysis of Supernatants

After binding, aliquots (2×100 µl) of supernatants from duplicate tubes were mixed with scintillant (10 ml) and sugar binding calculated by comparison with counts in aliquots of the original sugar solution.

(c) Chemical Analysis of Supernatants

Phenol-Sulfuric Acid Test: Analysis of glucose and maltose was carried out by a modification of the method of Dubois [28]. Aliquots (3×75 µl) of supernatant were taken from each tube, mixed well with phenol solution (2.5%, 2 ml) and sulfuric acid (98%, 5 ml) added rapidly. The solutions were allowed to cool to room temperature and read at 490 nm. The sugars remaining in the supernatants were estimated by comparison with standard maltose solutions.

Morgan-Elson Test: Analysis of N-acetylglucosamine was carried out by a modification of the method of Strominger et al [29]. The stock Morgan-Elson reagent was prepared by dissolving dimethylaminobenzaldehyde (16 g) in glacial acetic acid (75 ml), adding concentrated hydrochloric acid (5 ml) and diluting to 100 ml with acetic acid. The stock reagent was diluted (2:5) with acetic acid before use. The beads were heated in maltose solutions in water. To aliquots (3×75 µl) of supernatant, disodium tetraborate solution in water (5%, 75 µl) was added and the tubes heated for 7 min at 100° C., followed by immediate cooling in an ice bath. Aliquots (700 µl) of diluted Morgan-Elson reagent were added to each tube and the mixed solutions were heated at 37° C. for 20 min and read immediately at 585 nm. The sugar remaining in the supernatants was estimated by comparison with standard N-acetylglucosamine solutions.

(d) Enzymatic Analysis of Bound and Unbound Maltose

Binding of maltose to beads, enzymatic hydrolysis and glucose analysis were all carried out in phosphate buffer (0.1M, pH 6.6). The binding supernatants were used for both enzymatic analysis [30] and a phenol-sulfuric acid measurement (Table 8).

TABLE 8

Binding of maltose to aminopolystyrene beads

| Detected sugar | Method of Analysis | Maltose (nmol) |
|---|---|---|
| Bound maltose | enzymatic | 176 |
| Bound maltose | chemical | 147 |
| Released glucose | enzymatic | 76 |

Enzymatic hydrolysis of Maltose: Treatments with α-glucosidase were carried out in glass tubes using the following samples: 1. Replicates of one maltose-substituted bead, immersed in buffer (100 μl); 2. Aliquots (100 μl) of the binding supernatant; and 3. Maltose standard solutions in buffer (200 μM, 100 μl). The samples were incubated with α-glucosidase solution (1 U/ml, 10 μl) with shaking at 37° C. for 1.5 h.

Enzymatic analysis of glucose: A stock enzyme solution contained glucose oxidase (0.9 U/ml) and horseradish peroxidase (0.4 U/ml) in phosphate buffer. The test reagent was prepared immediately before use by mixing enzyme solution (6 ml) with a solution of ABTS substrate (0.115 mM, 12 ml). The solutions from the hydrolysis step were tested directly, together with a series of glucose standards containing 1 to 9 μg glucose in buffer (100 μl). Aliquots (750 μl) of test reagent were added to each tube, then incubated at 37° C. for 20 min and read at 420 nm.

(e) Immunochemical Analysis of Bound Maltose

Phosphate-buffered saline (PBS-T) was 0.14M NaCl containing phosphate buffer (0.01M pH 7.4) and 0.05% Tween-20. Beads were incubated with 0.1 mM maltose or lactose solutions in phosphate buffer (pH 4.3) at 100° C. for 3 h.

The beads were blocked for 2 h with either 1% gelatin or 10% Boehringer Mannheim Blocking Reagent, followed by 4 washes with PBS-T, and incubated for 2 h with a $\frac{1}{50}$ dilution of Concanavalin A in PBS-T containing 0.1 mM $Mn^{2+}$ and $Ca^{2+}$. The beads were again washed 4 times with PBS-T and incubated for 2 h with a $\frac{1}{20}$ dilution of rabbit anti-Concanavalin A, washed 4 times with PBS-T and incubated for 2 h with a $\frac{1}{1000}$ dilution of sheep anti-rabbit IgG-horseradish peroxidase conjugate, washed 4 times with PBS-T and the beads transferred to a microtitre plate, with 1 bead per well. A solution of mannose (0.5M in PBS-T, 100 μl) was added to each well and incubated at 25° for 15 min. The beads were then removed and ABTS substrate solution (100 μl) added [31]. The mixture was incubated with shaking and the color development stopped by addition of sodium azide (1 mM, 50 μl) after an appropriate time (30–60 min). The results were expressed as ratios of absorbances obtained from the maltose-substituted beads to those from the lactose-substituted beads as a negative control (Table 9).

TABLE 9

Immunochemical analysis of polymer-bound maltose

| Bound sugar | Absorbance (412 nm) ratio | Maltose/Lactose |
|---|---|---|
| maltose | 0.948 | 13.2 |
| lactose | 0.072 | |
| maltose | 1.044 | 8.2 |
| lactose | 0.128 | |
| maltose | 1.288 | 7.0 |
| lactose | 0.183 | |
| maltose | 1.154 | 8.3 |
| lactose | 0.139 | |

Derivatisation of Polystyrene Beads

Nitration was carried out at a low temperature to minimise physical damage to the beads. If the temperature of the reaction mixture was allowed to rise to 20° C., the beads adhered in clumps, resulting in uneven nitration of the surface. Consistent results were obtained with a reaction for 3 h at 5° C. Longer times resulted in more deeply colored beads, because of a higher degree of nitration; if the temperature was maintained below 3° C., the rate of nitration was quite slow.

Reduction with stannous chloride was carried out at between 75° C. and 90° C. for 2–3 h. Higher temperatures gave more efficient reduction but, above 90° C., the beads became soft and sticky, although they maintained acceptable sugar-binding properties. The degree of derivatisation was typically 500–700 nmol of amino groups per bead after reduction at 90° C. Milder chemical reductions, such as with dithionite or titanium(III) chloride, were also explored, but the degree of reduction was much lower. The reduced beads were stored at 4° C. under 1M HCl to prevent oxidation of the amino groups. The sugar-binding characteristics of the beads were stable over several months.

Binding of Sugars to Derivatised Polystyrene Beads

Figure 22:
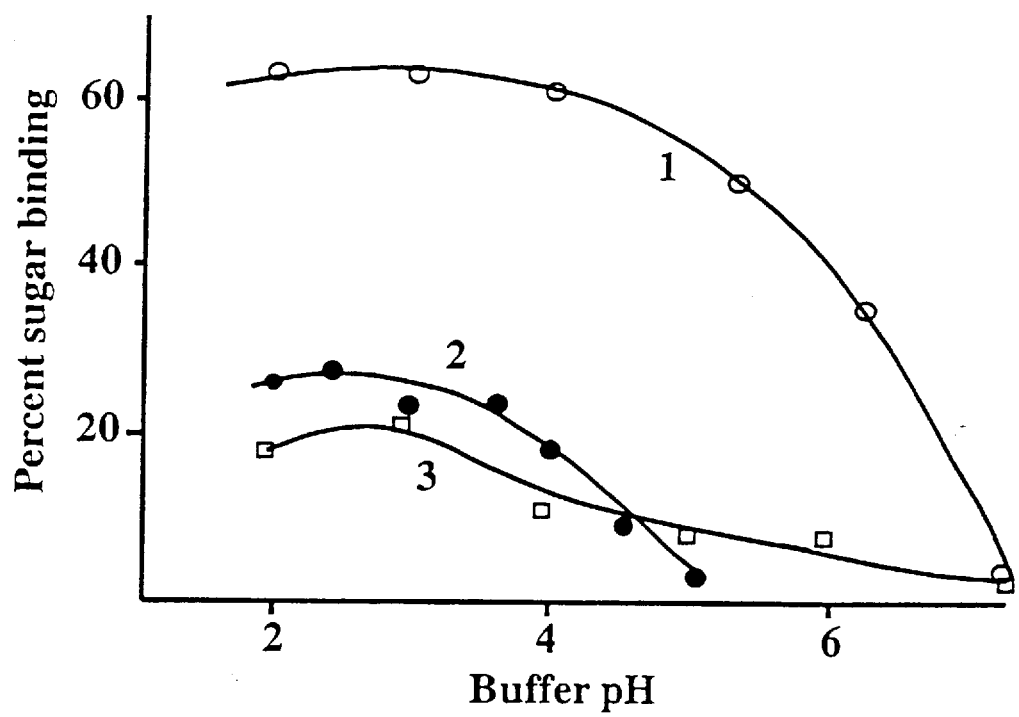
FIG. 22 shows binding of reducing sugars to aminopolystyrene at 100° C. as a function of pH in 0.1M citrate-0.2M phosphate buffers. Curve 1: 1 mM maltose for 2 h, analysed by the phenol-sulfuric acid test; Curve 2: $^{14}$C-glucose for 0.5 h; Curve 3: $^{14}$C-N-acetylglucosamine for 2 h.

Monosaccharide analysis: The binding of $^{14}$C-glucose and $^{14}$C-N-acetylglucosamine to aminopolystyrene beads was determined by heating the beads with solutions of the labelled sugars and measuring the activity left in the supernatants. The influence of the buffer pH on the rate of binding (FIG. 22) was determined for short heating times, to approximate initial-rate conditions. The extent of binding of sugars was also investigated for different heating times (FIG. 21).

The stability of binding of $^{14}$C-glucose and $^{14}$C-N-acetylglucosamine to beads, after heating at 100° C. for 2 h in buffers from pH 2.0 to 7.0, was investigated by allowing them to stand first in PBS-T for 16 h, to assess whether the sugar binding was adequate for immunochemical experiments, and then in 3M acetic acid for 4 h to release any glycosylamine present. At no stage was significant radioactivity was observed in the supernatants.

The extent of binding of solutions of maltose and N-acetylglucosamine to aminopolystyrene beads under various conditions was determined by analysis of the supernatants by the phenol-sulfuric acid [28] and Morgan-Elson [29] tests, respectively. The extent of binding (FIG. 21) was consistent with those obtained by radiochemical analysis.

Maltose Analysis: The kinetics of binding maltose were similar to those for glucose and, under optimal conditions, binding was essentially complete (FIG. 21). The accessibility of the bound maltose was determined by an assay of glucose released from the beads by α-glucosidase. The results (Table 8) show that 43–52% of the bound maltose was accessible to hydrolysis by the enzyme.

The binding of maltose was also assessed by an enzyme-linked lectin-binding assay. The lectin, Concanavalin A (Con A), which has a specificity for α-D-mannopyranosides>α-D-glucopyranosides>α-N-acetyl-D-glucosaminides, was used to demonstrate the presence of maltose on the beads, using bound lactose as a control.

Non-specific binding of proteins to the polystyrene matrix proved troublesome, and was aggravated by the introduction of the amino groups. Modification of the amino groups, by acetylation or coupling with erythrose, had no effect. Several methods of protein blocking, such as 2% bovine serum albumin and 1% gelatin, were used, but 10% Boehringer Mannheim Blocking Reagent proved the most effective. Alternatively, high background readings were obviated by means of hapten displacement of the Concanavalin A-antibody complex, using methyl α-D-mannopyranoside or mannose (Table 9).

Figure 23:
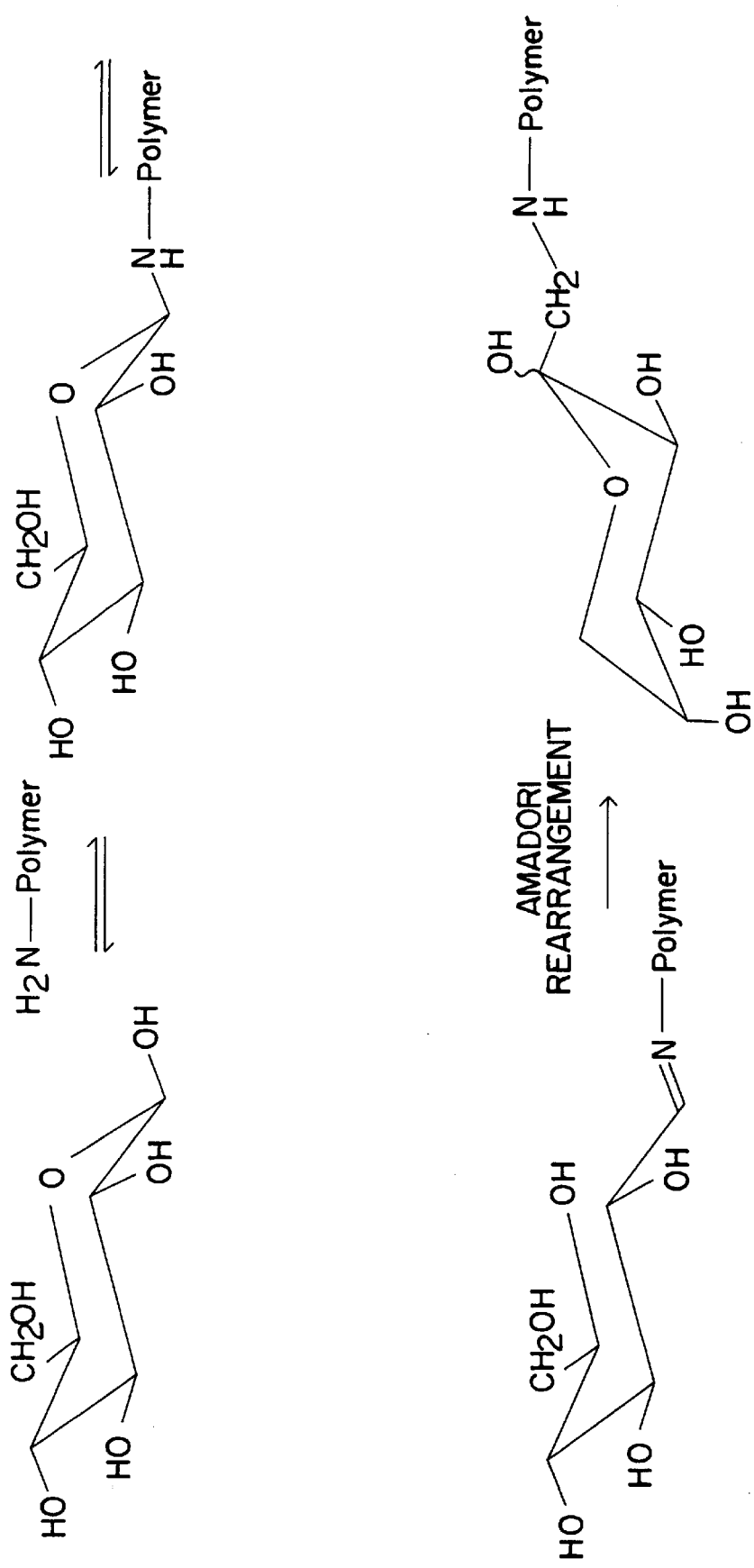
FIG. 23 shows steps in the reversible formation of an aminopolystyrene-bound glycosylamine of glucose and its irreversible conversion to an Amadori product.

The binding of the sugars is most effective under mildly acidic conditions (FIG. 22), which are known to favour the Amadori rearrangement [32]. It is likely that the sugars undergo a rapid and reversible formation of glycosylamines, which are converted irreversibly, through the open-chain imino form and a slave Amadori rearrangement (FIG. 23), to 1-aminodeoxyketoses which are not liable to hydrolysis.

V. SEPARATION OF SITE SPECIFIC CARBOHYDRATE FROM A GLYCOPROTEIN/ GLYCOPEPTIDE

MATERIALS

Glycoproteins

Several different glycoproteins including those available as commercial preparations have been analysed; human Glycophorin A (Sigma G 9266)[33] and bovine k-casein macroglycopeptide (Sigma C 7278) are both inexpensive sources of O-glycosylated domains and the trypsin inhibitor, ovomucoid (Sigma) is a source of N-linked oligosaccharides. Both Glycophorin A and ovomucoid contain glycosylated amino acids in the first ten amino acids from the N-terminus. Other sources of glycoprotein include Human Casebrook serum albumin (Asp494→Asn, creates an N-linked glycosylation site)[10] and the Dictyostelium recombinant glycoprotein PsA, which contains O-linked GlcNAc[34,35].

Covalent attachment of glycoproteins to immobilised isothiocyanate and amine

Glycopeptides generated by endoproteinase Lys-C digests are optimal for solid-phase sequencing as they are coupled to immobilise isothiocyanate (such as Sequelon-DITC™) via their C-terminal ε-amino group. However, not all glycoproteins will contain a convenient Lys for this strategy. A more generic approach is to attach peptides via the a-carboxyl group to an immobilised amine (such as Sequelon-AA™), using water soluble carbodiimide [36]. One precaution that is necessary with Sequelon-AA™ immobilisation is to manipulate the sialic acid on glycopeptides, because in addition to the amino acid side chain and C-terminal carboxyls, the terminal sialic acid carboxyl groups of the oligosaccharide also form amide bonds with the immobilised amine, hence immobilising the ATZ-sialylamino acid [10].

Desialylation

Glycopeptides/proteins are desialylated in 200 μl of 0.1M trifluoroacetic acid (TFA) and incubated at 80° C. for 40 min. Most of the TFA is removed in the vacuum centrifuge but it is not necessary to remove all traces before covalent immobilisation.

Amidation

An alternative procedure to removal of the sialic acid involves amidation of the sialic acid terminal carboxyl with a soluble amine and water soluble carbodiimide. The intact glycoprotein, or peptides which contain a C-terminal lysine (or arginine which can be converted to ornithine) are reacted with 10% (v/v) diethylamine and 5 mg of water soluble N-ethyl-N'-dimethylaminopropylcarbodiimide (EDC) for 30 min at room temperature. Amidated glycopeptides are separated from the reaction mixture via HPLC. Amidated glycoproteins are then subjected to endoproteinase digestion (preferably Endo Lys-C or trypsin) and the glycopeptides separated by HPLC.

Covalent attachment and solid-phase Edman degradation

Human glycophorin A (GpA)

Between 0.5–2 nmol of desialylated human glycophorin A was dissolved in 20% (v/v) acetonitrile and covalently attached to Sequelon AA™ membranes via the side-chain carboxyl groups using water soluble EDC. The coupling reaction was carried out by the addition of 5 μl of coupling buffer (0.1M MES 15% (v/v) acetonitrile pH 5.0+1 mg EDC), at 4° C. for 15 min as described previously [37]. The coupling reaction was terminated by vortexing the Sequelon AATM membranes in 1ml of 50% (v/v) methanol, followed by 1ml of methanol then drying the membranes at 55° C.

Bovine K-casein glycopeptides and tryptic peptides of serum albumin Casebrook and rPsA Between 0.2–1 nmol of desialylated glycopeptides were covalently attached to Sequelon AA™ membranes as described above. The amidated Casebrook albumin tryptic peptide (Arg484-Lys500, ~500 pmol in 15% v/v acetonitrile) was pipetted onto 1,4-phenylenediisothiocyanate derivatised membranes (Sequelon-DITC) wetted in 5 μl of wetting solution of 2% N-methylmorpholine/49% 2-propanol/49% water (v/v/v). The disk was allowed to dry at 55° C. (~5 min) before a second addition of the wetting solution. The disk was allowed to dry prior to Edman degradation.

Edman Degradation

Sequelon-AA and -DITC coupled protein/peptide membranes were subjected to automated solid-phase Edman degradation using a MilliGen ProSequencer™ 6600 where the ATZ-glycoamino acid is extracted from the reaction cartridge in anhydrous TFA. The PTH-glycoamino/amino acid derivatives were transferred directly from the conversion flask to the on-line HPLC system.

On line HPLC

The on-line HPLC system consisted of a Waters 600 multisolvent pump delivery system supported by a Waters 600-MS system controller and a Waters 490E programmable multiwavelength detector set at 269 nm and 313 nm. The PTH-amino acids were separated by on-line reversed-phase chromatography using a 3.9 mm×300 mm $C_{18}$ Nova-Pak™ (Waters) column. The typical tetrahydrofuran/sodium acetate PTH-amino acid analysis buffers are not compatible with the carbohydrate analysis of the PTH-glycoamino acids due to their high content of extraneous carbohydrate (either glucose or a glucose polymer) and sodium ions which interfere with mass spectrometry. The present inventors have used several acidic low ionic strength buffers such as 2 mM formic acid and 2 mM acetic acid for separation of PTH-glycoamino acids in a chromatographic space separate from the normal PTH-amino acids. The ideal buffer is 5 mM triethylammonium formate (TEAF) which provides a defined chromatographic space for the PTH-glycoamino acids as well as good separation of all 20 common protein amino acids. The TEAF buffer was prepared by the addition of 300 μl of formic acid to 1.2 l of degassed MilliQ water and the pH was adjusted to pH 4.0 with the addition of triethylamine (620 μl). Solvent B: 100% acetonitrile (Ajax chemicals, Australia); both solvent A and solvent B reservoirs were kept under constant helium head pressure of approximately 20 kPa during HPLC operation. Optimal separation of PTH-glycoamino/amino acids was achieved by the following gradient.

| Time | Solvent A | Solvent B |
| --- | --- | --- |
| initial | 95 | 5 |
| 0.7 | 80 | 20 |
| 1.4 | 73 | 27 |
| 2.8 | 73 | 27 |
| 5.7 | 55 | 45 |
| 7.4 | 55 | 45 |
| 8.1 | 53 | 47 |
| 12 | 20 | 80 |
| 20 | 95 | 5 |

For glycosylation site identification as little as 50–100 pmol of glycoprotein can be used for covalent attachment. However, for analysis of the oligosaccharide attached to individual glycoamino acids approximately 1–2 nmol of glycoprotein/glycopeptide was found necessary to obtain 400–800 pmole of PTH-glycoamino acid.

Analysis of the monosaccharide composition of PTH-glycoamino acids

The PTH-glycoamino acids collected from the HPLC in the formic acid buffer (approximately 400 pmol) and were hydrolysed in 2M TFA at 100° C. for 4 h. After vacuum evaporation of the acid, the liberated monosaccharides were analysed by High Performance Anion Exchange Chromatography (HPAEC) using a CarboPac PA1™ column (4 mm×250 mm, Dionex Corp., USA) on a Waters 625 LC system and Waters 464 pulsed amperometric electrochemical detector. Electrospray Ionisation Mass Spectrometry of PTH-glycoamino acids Mass spectra were acquired on a Perkin Elmer/Sciex API III triple quadrupole mass spectrometer (PE/Sciex, Ontario, Canada), equipped with an ionspray atmospheric pressure ionization source. Samples of PTH-Asn(Sac) (200 pmol in 50 $\mu$l) were flow injected into a moving solvent [10 $\mu$l min$^{-1}$; 50% (v/v) acetonitrile, 0.5% (v/v) TFA], whereas PTH-Thr (Sac) was analysed by liquid chromatography mass spectrometry (LCMS) on an Aquapore RP-300 C8 column (7$\mu$ 100×2.1 mm) using a 0.2% (v/v) formic acid buffer system and an acetonitrile gradient. The flow injection and LC were coupled directly to the ionization source via a fused silica capillary interface (50 $\mu$m i.d.×50 cm length). Sample droplets were ionized at a positive potential of 5 kV and entered the analyser through an interface plate and subsequently through an orifice (100–120 $\mu$m diameter) at a potential of 80 V (a sufficient potential to induce a limited amount of dissociation within the molecule). Full scan spectra were acquired over the mass range 400 to 2200 daltons with a scan step size of 0.1 dalton.

RESULTS

Glycopeptide/glycoprotein sequencing

Figure 24A:
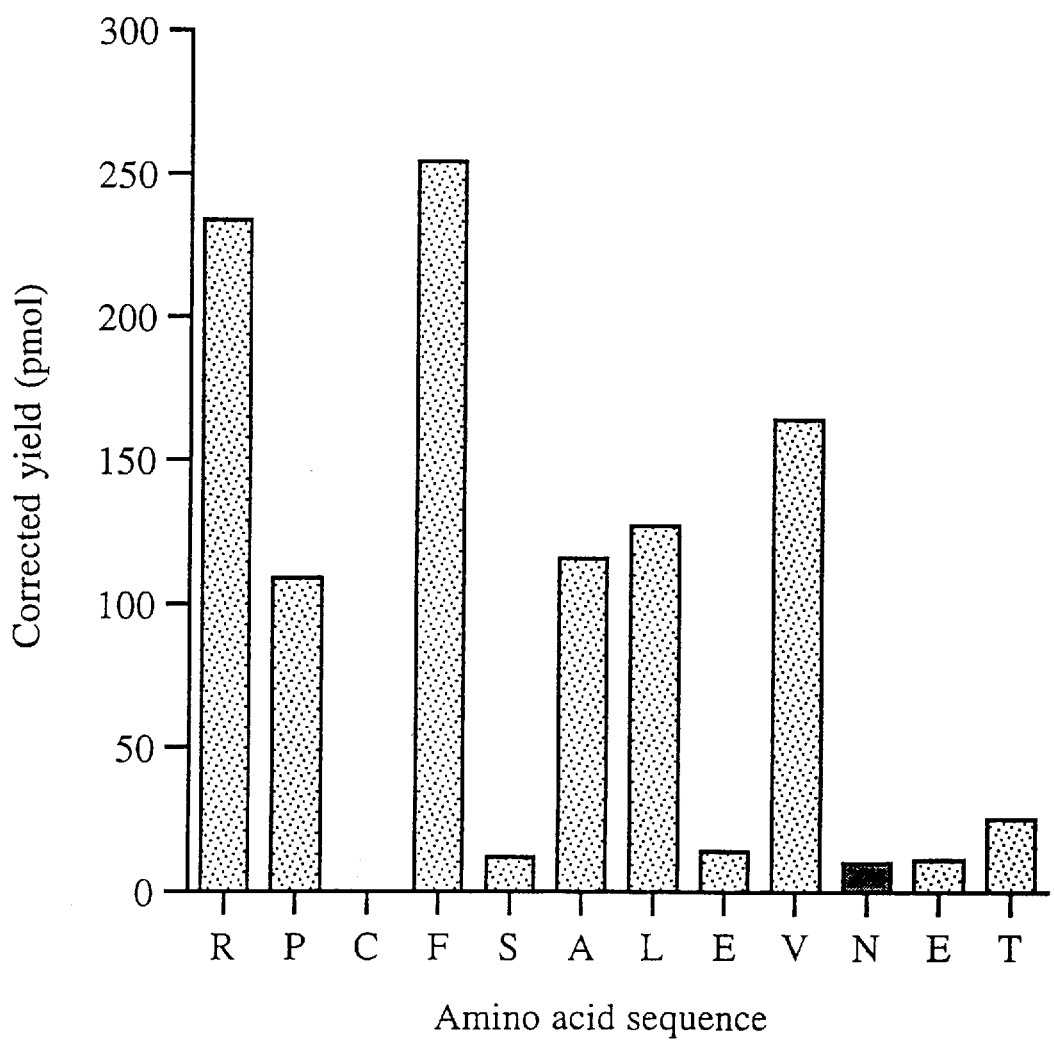
FIG. 24 shows corrected yields for PTH-amino acids from the solid-phase Edman degradation of the sialylated (a) and desialylated (b) Casebrook tryptic glycopeptides Arg485-Thr496. Non-glycosylated amino acids are shown by shaded bars and glycoamino acids by solid bars.
Figure 24B:
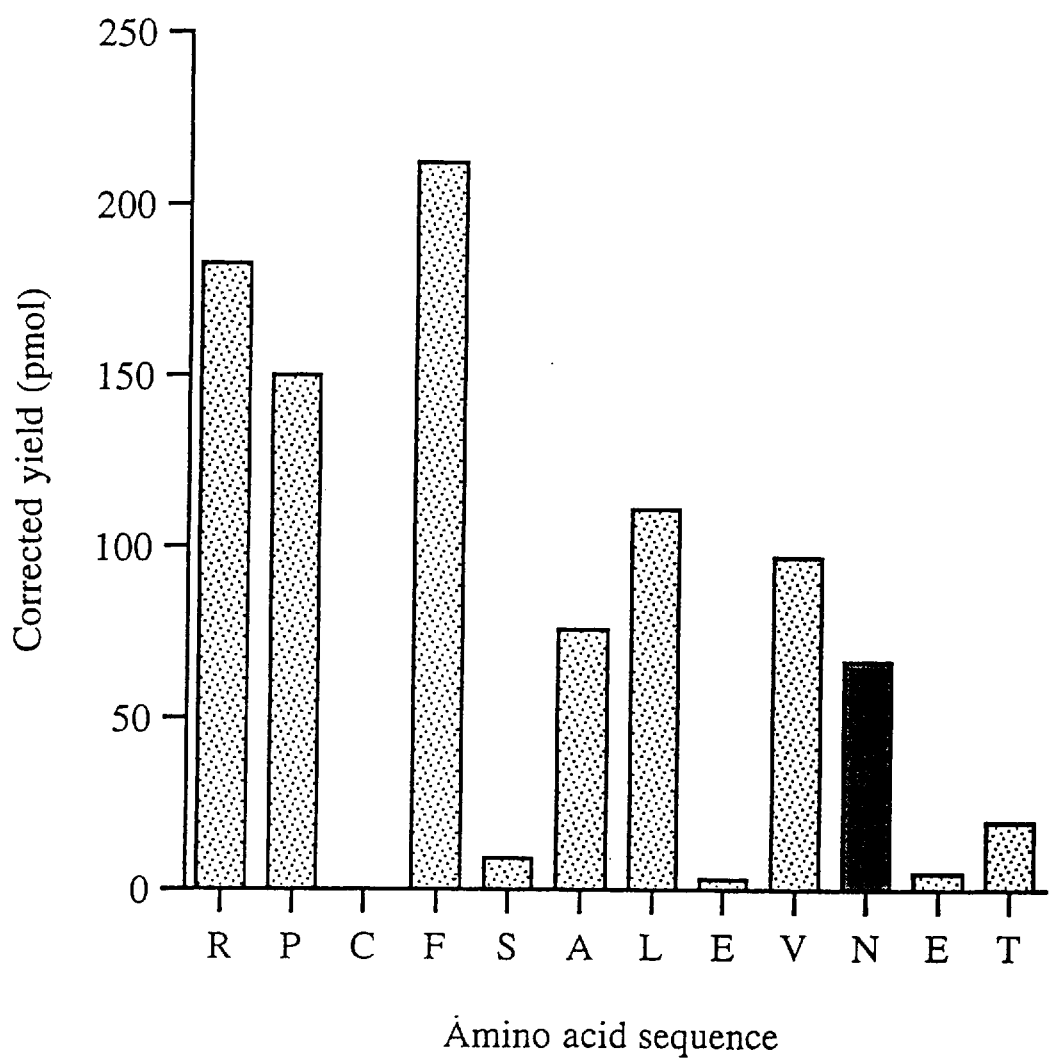

Glycopeptides were covalently bound to an arylamine derivatised membrane support at 4° C. Although the initial yields were encouraging, the corrected yield for Asn(Sac) 494 (FIG. 18 A, cycle 10) was disappointing. The low yield of PTH-Asn(Sac) (FIG. 24a) suggested to us that in addition to the a- and d-carboxyls, the terminal sialic acid carboxyl of the oligosaccharide also formed an amide bond with the arylamine membrane, hence immobilising the ATZ-Asn (Sac) to the PVDF disk. To test this, the tryptic peptide was subjected to mild acid hydrolysis to remove terminal sialic acid, bound to Sequelon-AA, and subjected to solid-phase Edman degradation. The yield of PTH-Asn(desialSac) was significantly increased (FIG. 24b), with a comparable yield to that obtained for PTH-Val in cycle 9.

Oligosaccharide composition after Edman degradation

Figure 25A:
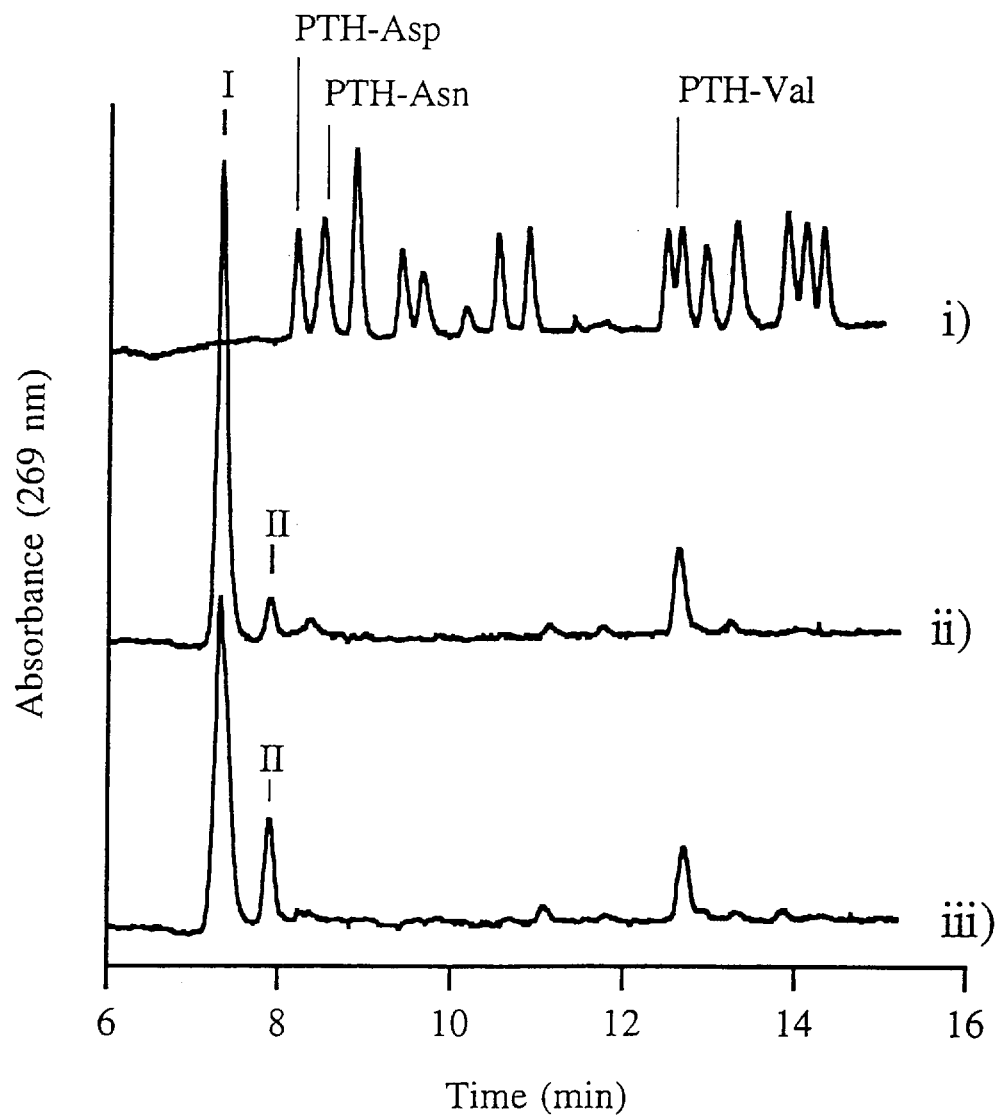
FIG. 25 shows high performance liquid chromatography chromatograms of PTH-Asn(Sac) released after Edman degradation of the Casebrook endoproteinase Glu-C fragment Val493-Glu495 (Aii) and tryptic fragment Arg485-Lys500 (Aiii). PTH-Thr(Sac) released after Edman degradation of the k-Casein peptide, Val139-Thr145, is shown in Bii. Chromatography conditions were; solvent A: 2 mM formic acid; solvent B 100% acetonitrile. The flow rate was 0.7 mlmin$^{-1}$ and column oven temperature 50° C. Ai and Bi are 35 pmol PTH-amino acid standard chromatograms. C and D: High performance anion exchange chromatograms using pulsed amperometric detection of monosaccharides released by 2M TFA hydrolysis of peak I 400 pmol of PTH-Asn494 (Sac) released at cycle 2 of the V8 peptide (C) and both PTH-Thr(Sac) peaks (D). The sugars were eluted isocratically with 15 mM NaOH and post-column addition of 0.4M NaOH, and identified by comparison with standards. An internal standard of 2-deoxyglucose was used for quantitation. Abbreviations are GlcNH$_2$ (glucosamine), Gal (galactose), Glc (glucose), Man (mannose).
Figure 25B:
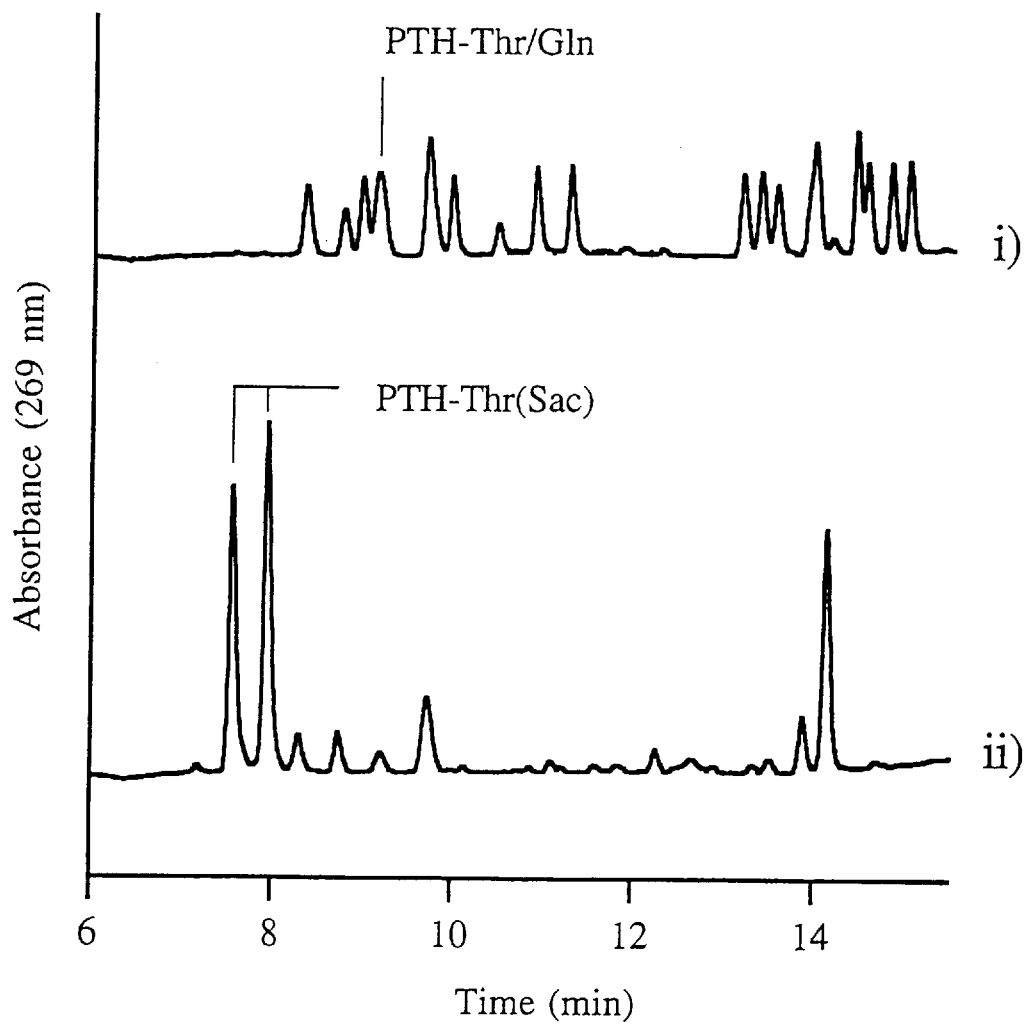
Figure 26:
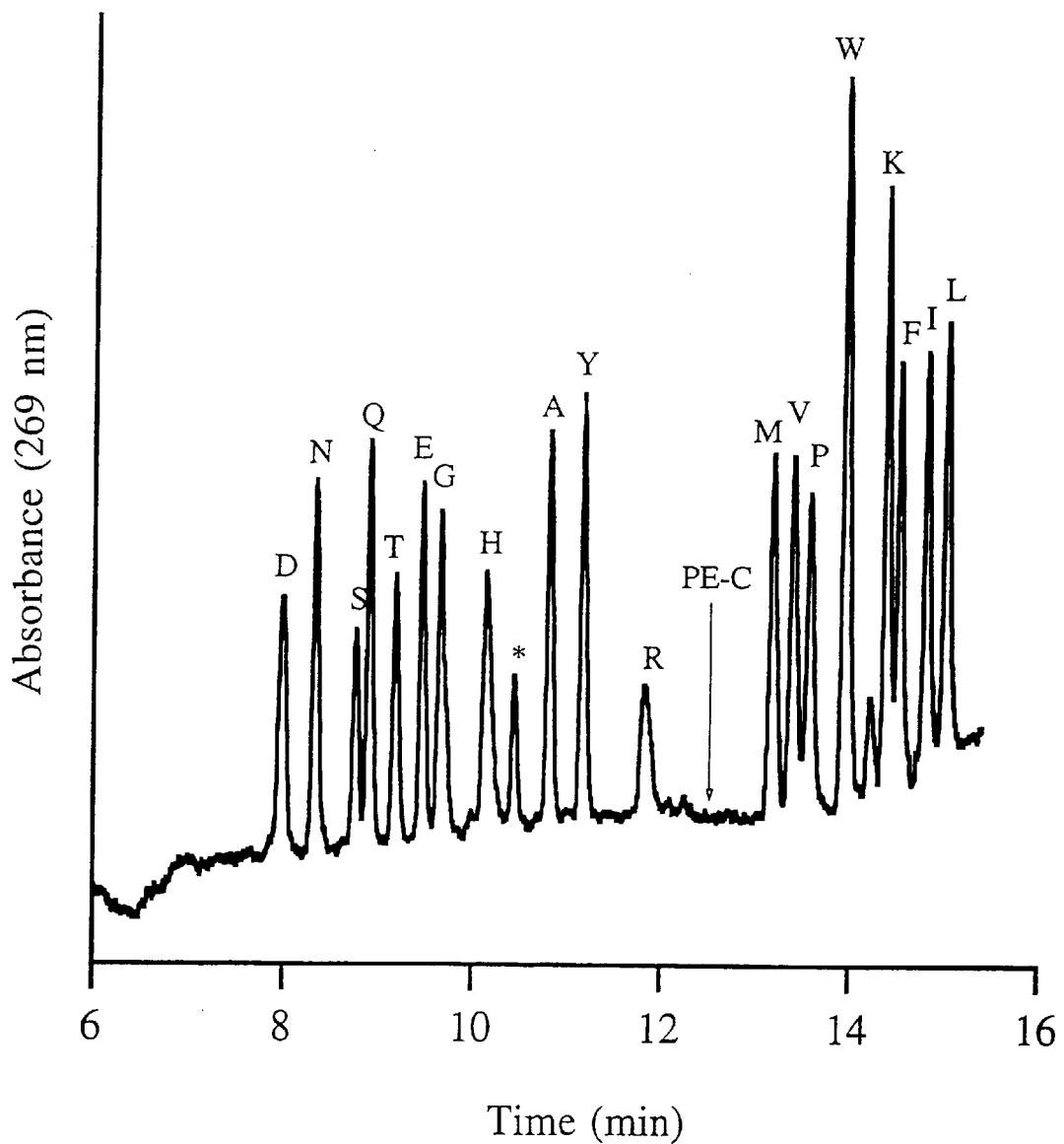
FIG. 26 shows high performance liquid chromatography chromatograms of 19 PTH-amino acid standards routinely encountered in N-terminal sequence analysis. The PTH-amino acids are (in order of elution): Asp (D), Asn (N), Ser (S), Gln (Q), Thr (T), Glu (E), Gly (G), His (H), DMPTU at 10.4 min, Ala (A), Tyr (Y), Arg (R), Met (M), Val (V), Pro (P), Trp (W) which co-elutes with DPTU, Lys (K), Phe (F), Ile (I) and Leu (L). PE-Cys (PE-C) is not routinely included in PTH-amino acid standards mixture and subsequently its elution time was identified separately. The elution position of PE-Cys is indicated on the elution profile by an arrow. The PTH-amino acids were separated using 5 mM TEAF, pH 4.0 as solvent A and acetonitrile as solvent B. The column was a NovaPak C$_{18}$ 3.9 mm×300 mm (4 micron, 60 Angstrom).
Figure 27:
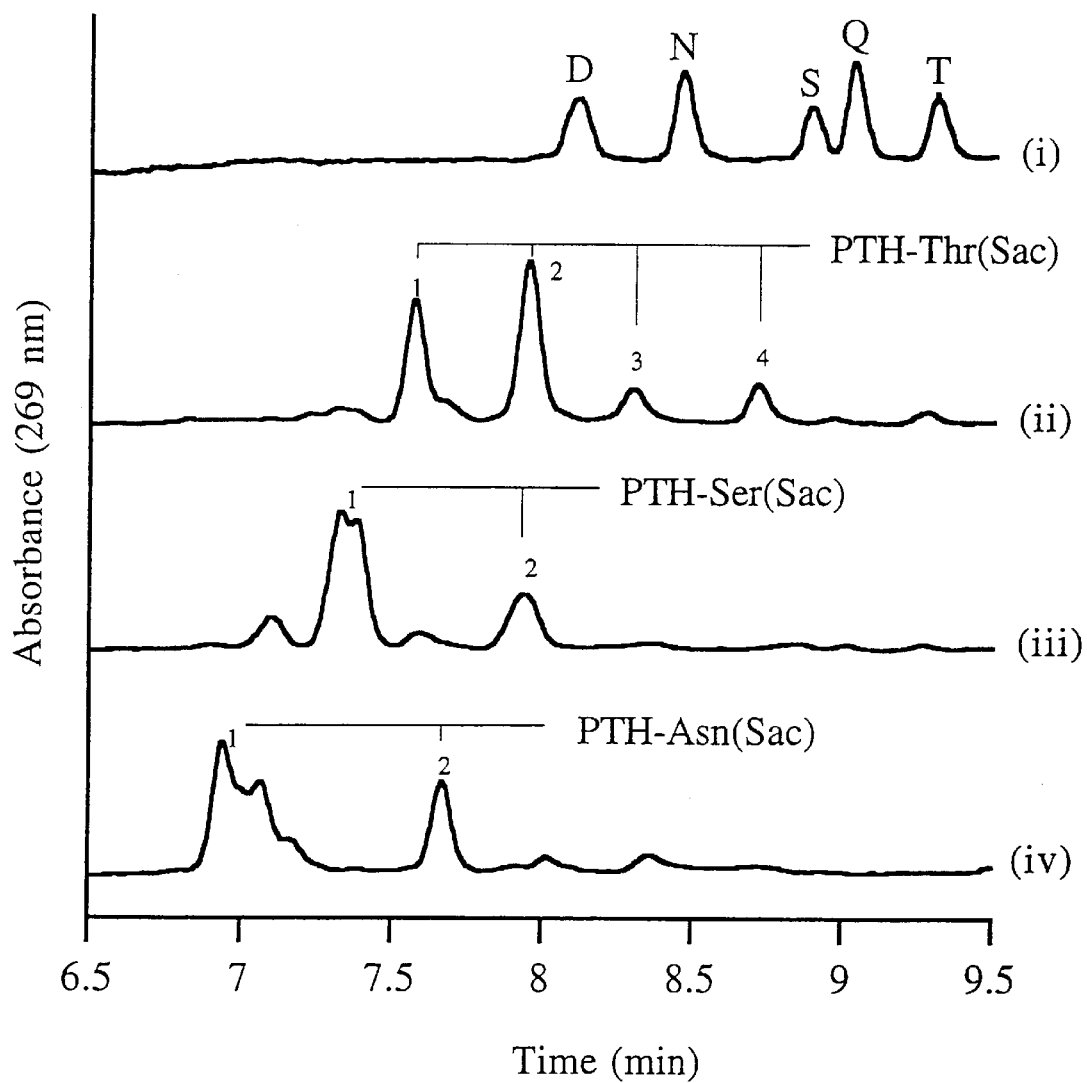
FIG. 27 shows high performance liquid chromatography chromatograms of all three major PTH-glycoamino acids. A comparison of the C$_{18}$ HPLC elution profiles for the three main groups of PTH-glycoamino acids: Asn(Sac), Ser(Sac) and Thr(Sac) separated with solvent A as 5 mM TEAF buffer, pH 4.0 (a) First five PTH-amino acids to elute from the column: Asp (at 8.0 min); Asn (at 8.3 min); Ser (8.75 min), Gln (8.89 min) and Thr (at 9.2 min). (b) PTH-Thr(Sac) and (c) PTH-Ser(Sac) from the N-terminal sequence of human glycophorin A after 4 and 2 cycles of Edman degradation, respectively. (d) PTH-Asn(Sac) and the albumin Casebrook tryptic glycopeptide following 10 cycles of Edman degradation.

With conditions optimised for PTH-Asn(desialSac) yield, attempts were made to obtain compositional analysis on the recovered oligosaccharide. Following 2M TFA hydrolysis of PTH-Asn494(desialSac), the yields of monosaccharides were dwarfed by a high glucose contamination. Glucose is a ubiquitous contaminant, which is difficult to exclude from any compositional assay. The principal source of glucose contamination was localised to the HPLC buffer, ammonium acetate, and the plastic tubes used to collect the PTH-amino acids. Tissue paper fines were the principal source of glucose contamination in the plastic tubes and must be kept in a paper/cardboard free environment. Rather than search for a new source of glucose free ammonium hydroxide/acetic acid, the present inventors established an alternative separation system, using a slightly acidic buffer system 5 mM formic acid. One advantage of the new buffer conditions resulted in an earlier elution of the PTH-Asn(desialSac) from the amino acids PTH-Asp and PTH-Asn (FIG. 25a) and PTH-Thr(desialSac) from PTH-Thr (FIG. 25b) using the 2 mM formic acid buffer and separation of PTH-Asn (desialSac), PTH-Thr(desialSac) and PTH-Ser(desialSac) as well as all 20 protein PTH-amino acids using the 5 mM TEAF buffer (FIG. 26 and 27).

After 10 cycles of Edman degradation of the Casebrook albumin tryptic peptide Arg485-Lys500, there is chromatographic evidence for heterogeneity. This is indicative of some degradation of the oligosaccharide, with the increase in yield of PTH-Asn(Sac) II after 10 cycles (14% of total yield) compared to PTH-Asn(Sac) II (5% of total yield) after 2 cycles of the Casebrook albumin V8 peptide Val493-Glu495 (FIG. 25aii and iii). However, the combined yields of the major (I) and minor (II) peaks for PTH-Asn(Sac) from cycle 2 (V8 glycopeptide) and cycle 10 (tryptic glycopeptide) were essentially identical.

Figure 25C:
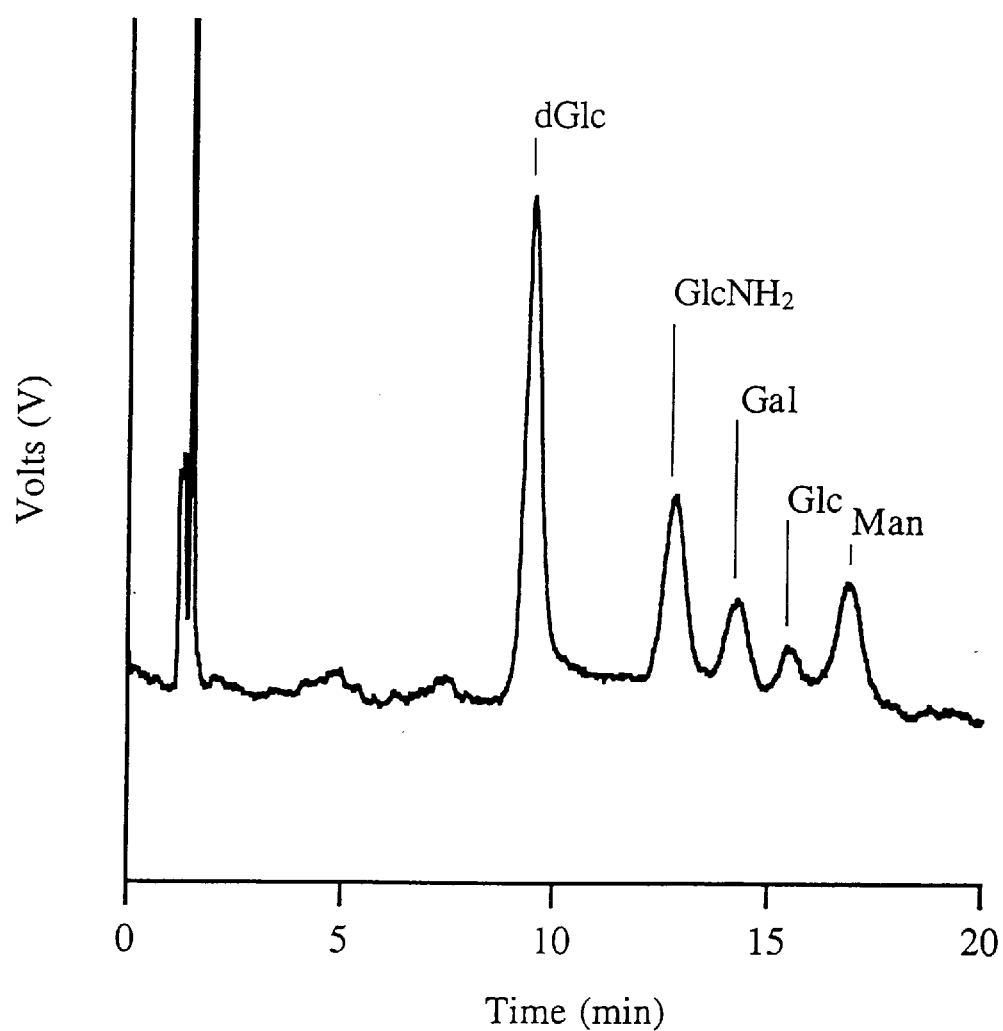
Figure 25D:
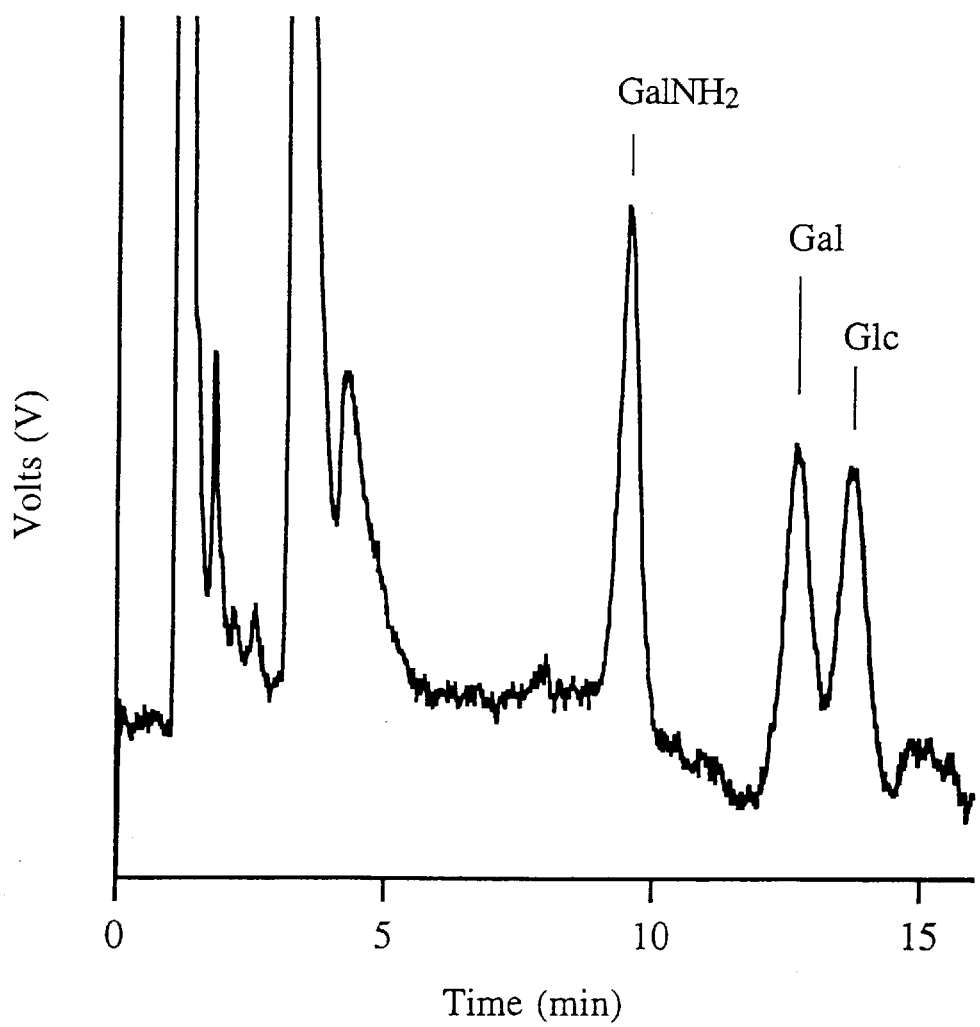

The major PTH-Asn(Sac) peak from cycle 10 of the Casebrook albumin tryptic glycopeptide (360 pmol) and PTH-Thr(Sac) peaks of the k-Casein peptide Val139-Thr145 (400 pmol) were collected and subjected to compositional analysis by HPAEC-PAD (FIG. 25c and 25d respectively). The observed compositions were consistent with the presence of a complex biantennary oligosaccharide for PTH-Asn(Sac), GlcNAc$_4$:Man$_3$:Gal$_2$, and the disaccharide Gal-NAc:Gal for PTH-Thr(Sac) (Table 10). Hence, much of the desialylated oligosaccharide structure remains intact on the glycosylated Asn and Thr during as many as 10 cycles of Edman degradation. The pattern of glycosylated PTH-Thr (Sac) peaks (FIG. 25bii) is identical to that observed in the rat CD8α hinge peptide [34] and glycophorin A [33], with two major peaks The stability of Asn(desialSac) to repeated cycles of Edman degradation was also examined by sequencing both the V8 peptide, where Asn(desialSac) appears in cycle 2, and the tryptic peptide where Asn (desialSac) appears in cycle 10.

TABLE 10

Monosaccharide composition of isolated glycoamino acids

| | Composition mol/mol[a] | | |
| --- | --- | --- | --- |
| | Casebrook Albumin | | k-Casein |
| Sugar constituent | [b]Asn494(Sac) | [c]Asn494(Sac) | Thr142(Sac) |
| glucosamine | 3.8 | 3.2 | 0 |
| galactosamine | 0 | 0 | 1.0 |

TABLE 10-continued

Monosaccharide composition of isolated glycoamino acids

| | Composition mol/mol[a] | | |
|---|---|---|---|
| | Casebrook Albumin | | k-Casein |
| Sugar constituent | [b]Asn494(Sac) | [c]Asn494(Sac) | Thr142(Sac) |
| galactose | 2.2 | 1.7 | 0.9 |
| mannose | 2.6 | 2.9 | 0 |

Figure 28:
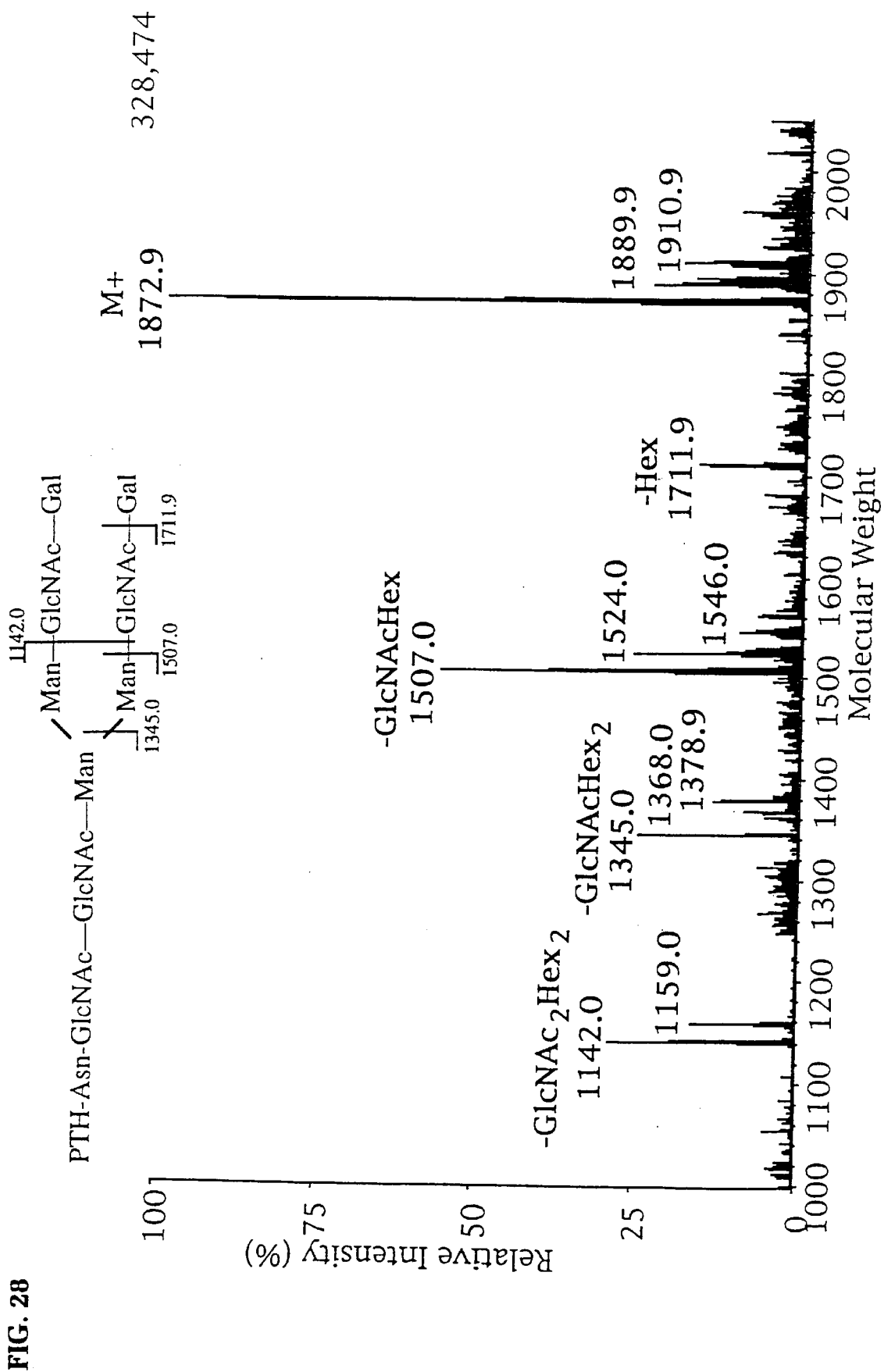
FIG. 28 shows the reconstructed ion-spray mass spectrum for PTH-Asn494(sac). PTH-Asn(sac) was released at cycle 10 from the peptide Arg485-Lys500 (see FIG. 25 Aiii), Mass of PTH-Asn=249.3, x-axis is adjusted to molecular mass.
Figure 29:
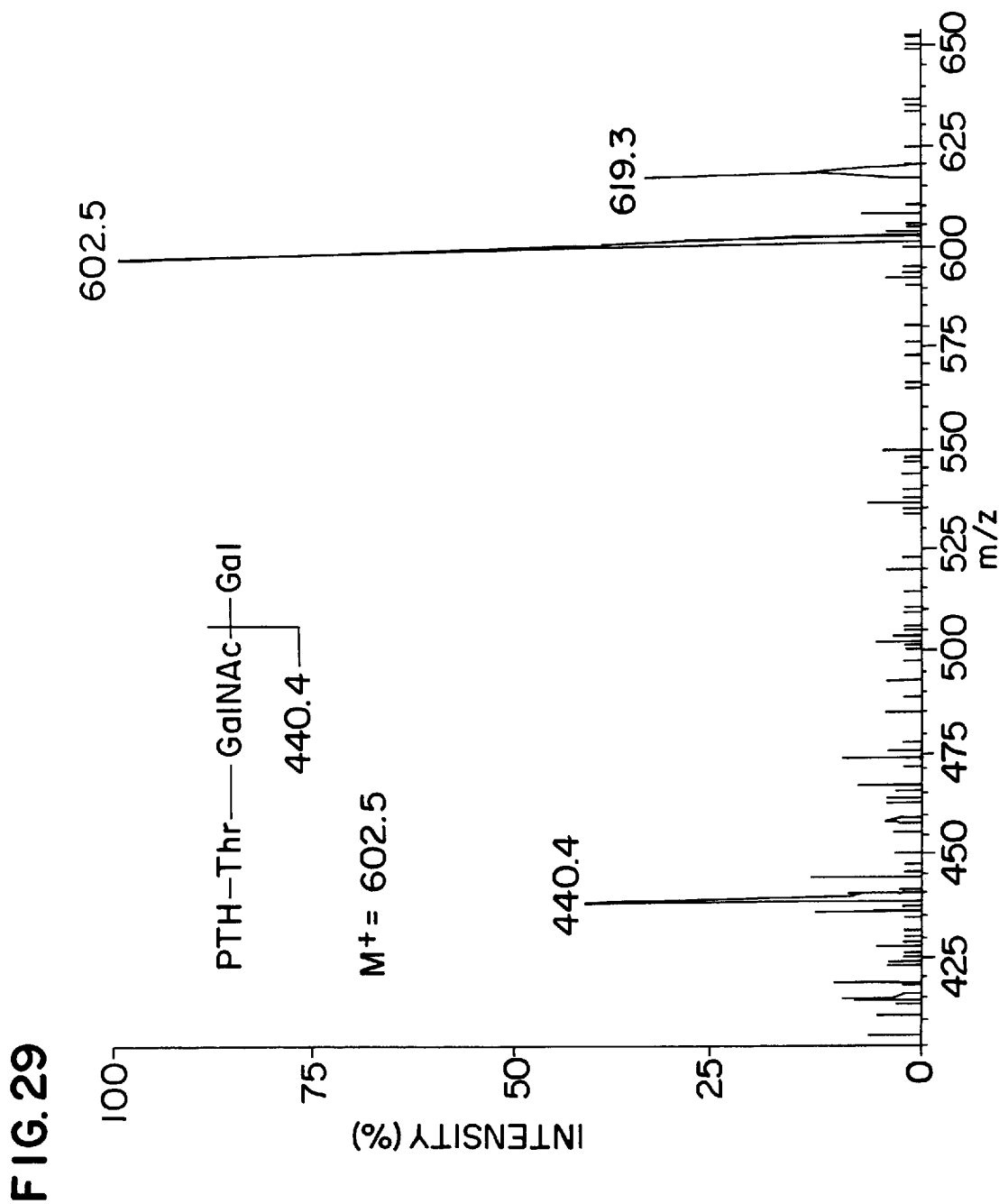
FIG. 29 shows the reconstructed ion-spray mass spectrum for PTH-Thr142 (sac). Mass of PTH-Thr=236.5, x-axis is mass/charge.

[a]Normalised on the amount (400 pmol) of PTH-Xaa(Sac) collected Monosaccharide composition was quantified by the inclusion of 1 μg of the internal standard deoxyglucose
[b]Peak I of the PTH-Asn(Sac) recovered from cycle 2 of the V8 glycopeptide
[c]Peak I of the PTH-Asn(Sac) recovered from cycle 10 of the tryptic glycopeptide Ionspray mass spectrometry of PTH-glycoamino acids Additional evidence concerning the nature of the oligosaccharide attached to Casebrook albumin PTH-Asn494 and k-Casein PTH-Thr142 was obtained by ionspray mass spectrometry. The determined mass for PTH-Asn-GlcNAc$_4$:Man$_3$:Gal$_2$ was 1,872.9 daltons (FIG. 28, 1,872.8 daltons expected) and for PTH-Thr-GalNAc:Gal 601.5 daltons (FIG. 29, 601.4 expected). Limited structural information was obtained by increasing the orifice potential; for example the 1507.0 ion (FIG. 28) results from the loss of a single hexosamine-hexose (366 daltons) and the 440.4 ion (FIG. 29) results from the loss of a hexose (162 daltons). Interpretation of the spectrum, however, is difficult because of the likelihood that some of the fragment ions arose from products of degradation during Edman sequencing.

Figure 30:
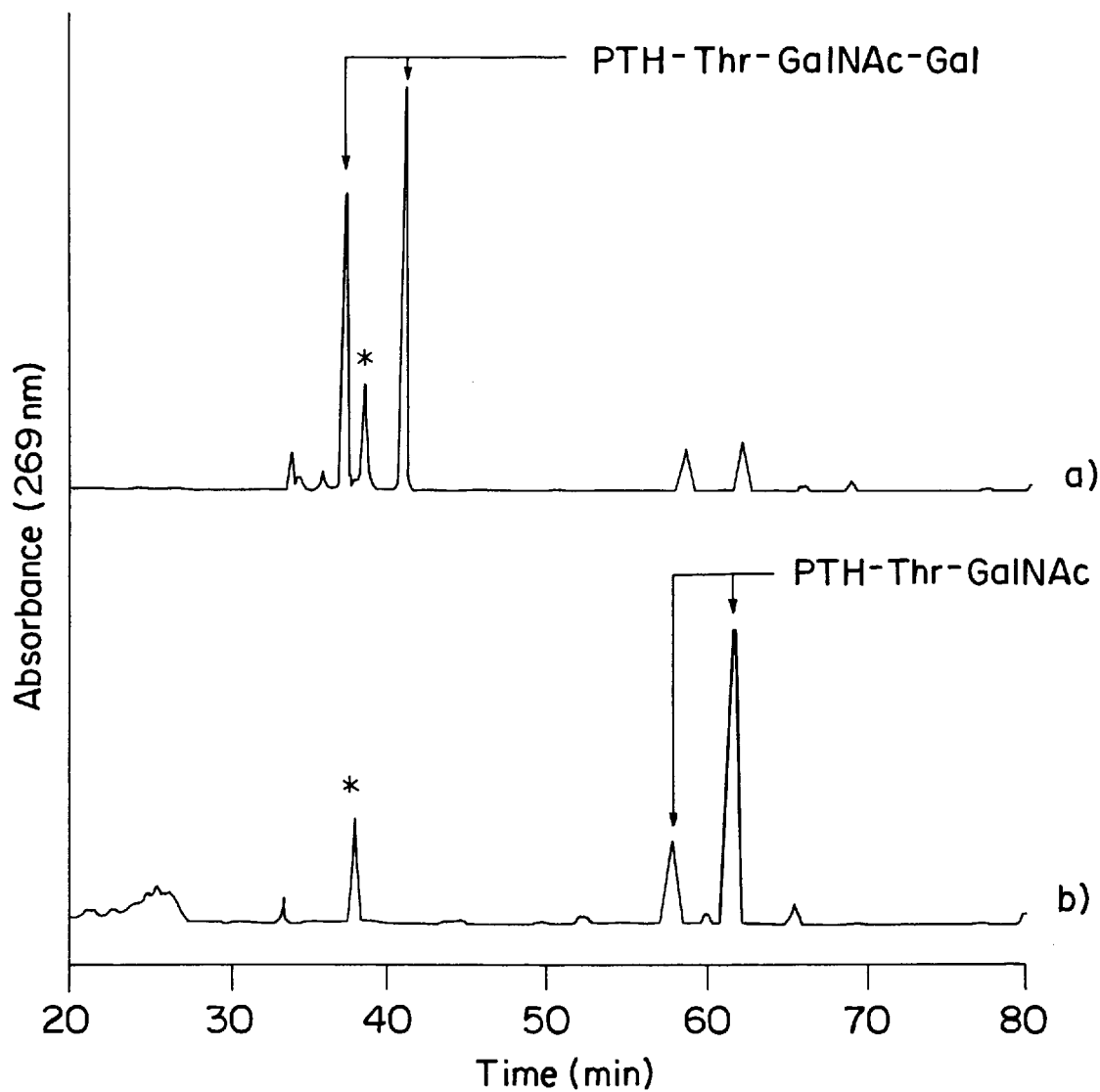
FIG. 30 shows high performance liquid chromatography chromatograms of PTH-Thr(GalNAc-Gal) before (a) and after (b) β-galactosidase treatment. Chromatography conditions were; solvent A: 0.05% (v/v) TFA; solvent B 60% (v/v) acetonitrile/0.045% (v/v) TFA. The flow rate was 0.1 ml min$^{-1}$.
Figure 31:
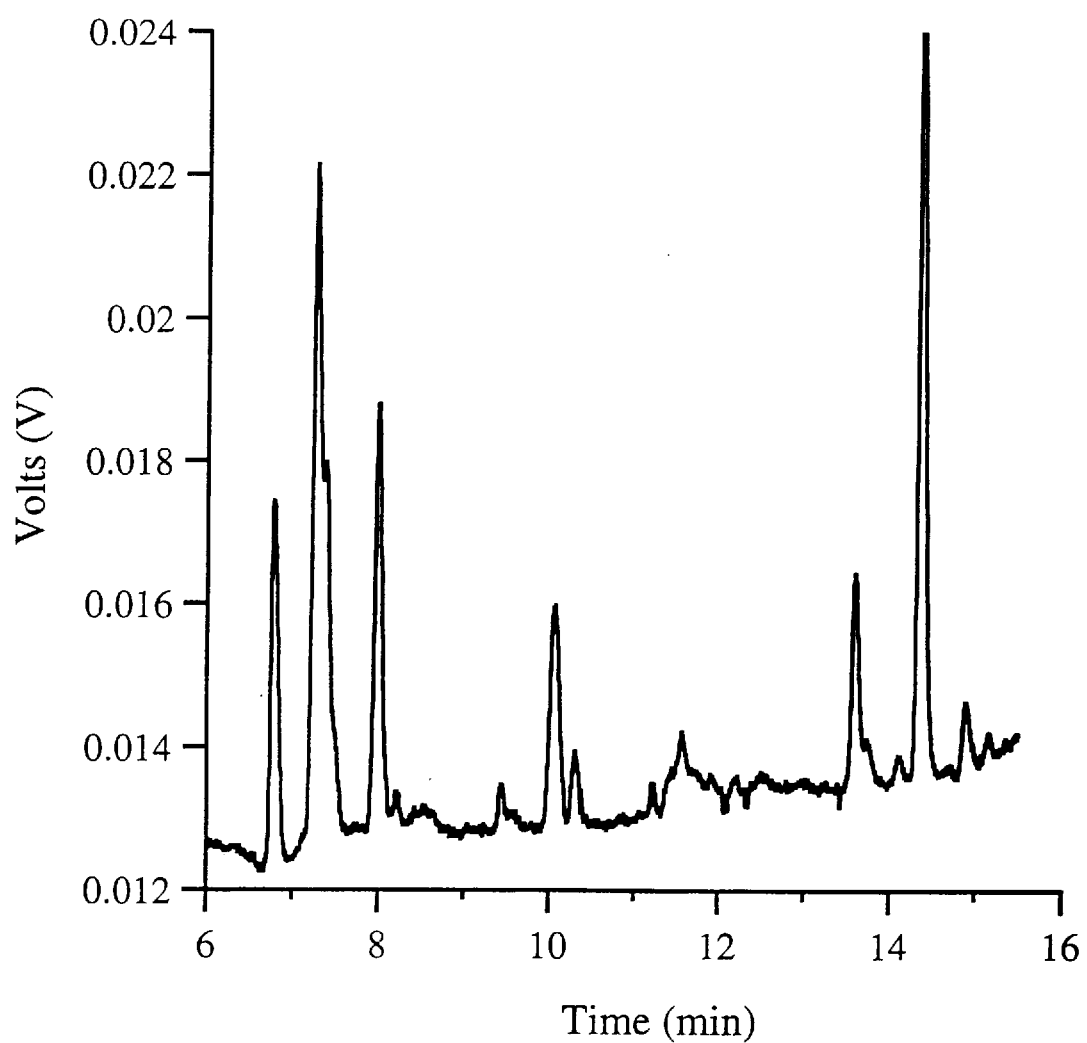
FIG. 31 shows the high performance liquid chromatogram of PTH-Asn494(Sac) released after Edman degradation of the amidated Casebrook tryptic fragment Arg485-Lys500. The amidated PTH-Asn(sac) is indicated at 6.75 min. Chromatography conditions were; solvent A: 2 mM formic acid; solvent B 100% acetonitrile. The flow rate was 0.7 ml min$^{-1}$ and column oven temperature 50° C.

Chromatographic analysis of PTH-Thr(GalNAc-Gal) Following B-galactosidase Treatment PTH-Thr3(GalNAc-Gal) from cycle 3 of the Edman degradation of immobilised glycophorin A was collected following HPLC and subjected to β-galactosidase treatment. Intact PTH-Thr3(GalNAc-Gal) and β-galactosidase treated PTH-Thr3(GalNAC-Gal) was subjected to reversed-phase HPLC analysis. There was a major shift in retention time following β-galactosidase treatment from 37 mins and 41 mins (FIG. 30) to 58 mins and 61 mins (FIG. 30). Amidation of sialylated oligosaccharides confers stability of the oligosaccharide during Edman degradation Amidation of the Casebrook albumin tryptic peptide Arg485-Lys500 modifies the sialylated oligosaccharide attached to Asn494. Prior to Edman degradation the peptide was immobilised via coupling the C-terminal Lys(500) to Sequelon-DITC™. In the HPLC chromatogram of tenth cycle of Edman degradation a new peak corresponding to the amidated oligosaccharide attached to PTH-Asn(494) was identified at 6.75 mins (FIG. 31).

The major advantage of the method is the analysis of a specific glycoconjugate attached to an amino acid in a domain of clustered glycosylation sites. Clustered glycosylation sites are typical of heavily O-glycosylated proteins such as the mucins and proteoglycans. The present inventors have demonstrated the efficiency of solid-phase Edman degradation by sequencing through the N-terminal domain of the "mucin-like" red blood cell glycoprotein GpA. As demonstrated by the present inventors, solid-phase Edman degradation in combination with techniques associated with the improved sensitivity of carbohydrate analysis (such as HPAEC and mass spectrometry), will allow a new approach into the characterisation of heavily glycosylated proteins previously thought too difficult for protein chemistry studies.

References

1. Montreil J (1982) in *Comprehensive Biochemistry* (Florkin G and Stoltz H E, eds) vol 19B, part II, pp 1–88, Elsevier, London
2. Damm J B L, Kamerling J P, van Dedem G W K, Vliegenthart J F G (1987) *Glycoconjugate J*. 4:129–144
3. Umemoto J, Bhavanandan V P, Davidson E A (1977) *J. Biol. Chem.* 252:8609–8614
4. Takasaki S, Mizuochi T, Takasaki A (1982) *Methods Enzymol*. 83:263–268
5. Patel T, Bruce J, Merry A, Bigge C, Wormald M, Jacques A, Parekh R (1993) *Biochemistry* 32:679–693
6. Carbuelli R, Bhavanandan V P, Gottschalk A (1965) *Biochim. Biophys. Acta* 101:67–82
7. Kallin E, Lonn H, Norberg T (1986) Glycoconjugate J 3:311–319
8. Blomberg L, Wieslander J, Norbert T (1993) J Carbohydr Chem 12:265–276
9. Tweeddale H J, Batley M, Mei X G, Redmond J W (1994) Glycoconjugate J 11:11–16
10. Gooley A, Pisamo A, Packer N, Ball M, Jones A, Alewood P, Redmond J, Williams K (1994) Glycoconjugate J. 11:180–186
11. Schmidt R, Kary J, Guillard W (1975) Angew.Chem. Int. Ed. Eng. 14:64–65
12. Bertolini M, Pigman W (1976) *J. Biol. Chem.* 242:3776–3781
13. Shimamura M, Inoue Y, Inoue S (1984) *Arch. Biochem. Biophys*. 232:669–706
14. Williams J M (1983) *Carbohydr. Res.* 117:89–94
15. Bendiak B, Cumming D A (1985) *Carbohyd. Res.* 144:1–12
16. Hodgkins J E, Reeves W P (1964) J Org Chem 29:3098–3099
17. Gardner T S, Smith F A, Wenis E, Lee J (1952) J Am Chem Soc 74:2106–7.
18. Williams J M (1983) Carbohydr Res 117:89–94
19. Drobnica L, Kristian P, Augustin J. (1977) In The Chemistry of Cyanates and Their Thio Derivatives, Part 2, (Patai S, ed) pp 1108–9. Chichester: John Wiley.
20. Aebersold R H, Pipes G D, Nika H, Hood L E, Kent S B H,(1988) Biochem 27:6860–6867
21. Mellet C O, Blanco J L J, Fernandez J M G, Fuentes J (1993) J Carbohydr Chem 12:487–505.
22. Manger I D, Rademacher T W, Dwek R A, (1992) Biochem 31:10724–10732
23. Manger I D, Wong S Y C, Rademacher T W, Dwek R A, (1992) Biochem 31:10733–10740
24. Yammamoto K, Tsuji T, Osawa T (1982) Carbohydr Res 110:283–289
25. Stowell C P, Lee Y C (1980) Adv Carbohydr Chem Biochem 37:225–281
26. Kobata A (1979) Anal Biochem 100:1–14
27. Palcic M M, Heerze L D, Pierce M, Hindsgaul O (1988) Glyconjugate J 5:49–63
28. Dubois M, Gilles K A, Hamilton J K, Rebers P A and Smith F (1956) Anal. Chem. 28:350–356.
29. Strominger J L, Park J T and Thompson R E (1959) J. Biol. Chem. 234:3263–3268.
30. Ngo T T and Lenhoff H M (1980) Anal. Biochem. 105:389–397.
31. Porstmann B, Porstmann T and Nuget (1981) J. Clin. Chem. Clin. Biochem. 19:435–439.
32. Hodge J E (1955) Adv. Carbohydr. Chem. 10:169–205.
33. Pisano A, Redmond J W, Williams K L, Gooley A A (1993) Glycobiology 3, 429–435.
34. Gooley A A, Classon B J, Marschalek R, Williams K L (1991) Biochem. Biophys. Res. Commun. 178, 1194–1201.

35. Gooley A A and Williams K L (1994) Glycobiology 4 (in press)
36. Coull J M, Pappin D J C, Mark J, Aebersold R, Koester H (1991) Analytical Biochem. 194, 110–120.
37. Laursen R A, Lee T T, Dixon J D, Liang S-P (1991) In: Jornvall H, Hoog J-O nd Gustvasson, A-M (ed's.) Methods in Protein Sequence Analysis. Birkhauser Verlag, Switzerland, pp. 47–54.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A method for the production of a sugar hydrazone comprising reacting an aqueous hydrazine hydrate with a reducing sugar in the presence of a further base, wherein the reaction does not require addition of acid to form the sugar hydrazone.

2. The method of claim 1 wherein said further base is sodium hydroxide.

3. The method of claim 2 wherein the sodium hydroxide is used at a concentration of 0.1M.

4. The method of claim 1 wherein said further base is triethylamine.

5. The method of claim 4 wherein the triethylamine is used at a concentration of 0.2M.

6. The method of claim 1 wherein the hydrazine hydrate and the base are removed after the production of the sugar hydrazone.

7. A method for the production of a sugar pyrazolone comprising reacting a sugar hydrazone produced by the method of claim 1 with a beta-dicarbonyl compound.

8. The method of claim 7 wherein the beta-dicarbonyl compound is acetyl acetone.

9. A method for the production of an 1-glycosylpyrazolone by reacting the sugar hydrazone produced by the method of claim 1 with a derivative of a beta-keto acid.

10. The method of claim 8 wherein the derivative of the beta-keto acid is ethyl acetoacetate or an activated ester of acetoacetic acid.

11. A method for the production of an azoglycan dye comprising subjecting a 1-glycosylpyrazolone produced by the method of claim 9 to azo coupling.

12. The method of claim 11 wherein the azo coupling is achieved by reacting the 1-glycosylpyrazolone with a diazotised primary aromatic amine.

13. The method of claim 12 wherein the diazotised primary aromatic amine is sulfanilic acid (4-aminobenzenesulfonic acid).

14. A method for the production of an hydrazoglycan dye comprising reacting an azoglycan dye produced by the method of claim 11 with a reducing agent such that the azo linkage of the dye is not cleaved.

15. The method of claim 14 wherein the reducing agent is selected from the group consisting of hydrosulfide, diimide, and formamidinesulfinic acid.

16. A method for the production of a reduced hydrazoglycan dye comprising treating the azoglycan dye produced by the method of claim 11 with a reducing agent such that the azo linkage of the dye is cleaved.

17. The method of claim 16 wherein the reducing agent is selected from the group consisting of dithionite in neutral or alkaline solution, sulfide, and polysulfide.

18. A method for the production of a glycoazomethine dye derivative comprising reacting at the 4-position of a 1-glycosypyrazolone produced by the method of claim 9 with an aromatic C-nitroso compound, or by oxidative coupling with a primary aromatic amine.

19. The method of claim 18 wherein the oxidative coupling is in the presence of a silver salt, hypochlorite or ferricyanide.

20. A method for the production of an azoglycan dye comprising the following steps:
    (i) reacting an aqueous hydrazine hydrate with a reducing sugar to form a glycosylhydrazone;
    (ii) reacting the glycosylhydrazone of step (i) with a derivative of a beta-keto acid to form a glycosylpyrazolone; and
    (iii) subjecting the glycosylpyrazolone of step (ii) to azocoupling to form an azoglycan dye.

21. The method of claim 20 wherein step (i) further includes sodium hydroxide.

22. The method of claim 21 wherein the sodium hydroxide is included at a concentration of 0.1M.

23. The method of claim 20 wherein step (i) further includes triethylamine.

24. The method of claim 23 wherein the triethylamine is included at a concentration of 0.2M.

25. The method of claim 20 wherein the derivative of the beta-keto acid is ethyl acetoacetate or an activated ester of acetoacetic acid.

26. The method of claim 20 wherein the azocoupling is achieved by reacting the glycosylpyrazolone with a diazotised primary aromatic amine.

27. The method of claim 26 wherein the diazotised primary aromatic amine is sulfanilic acid (4-aminobenzenesulfonic acid).

28. A method for the production of an hydrazoglycan dye comprising reacting the azoglycan dye of claim 11 or 20 with a reducing agent such that the azo linkage of the dye is not cleaved.

29. The method of claim 28 wherein the reducing agent is selected from the group consisting of hydrosulfide, diimide, and formamidinesulfinic acid.

30. A method for separation and analysis of a glycan which comprises of:
    (1) producing a glycan hydrazone derivative by the method of claim 1 or producing an azoglycan dye by the method of claim 20;
    (2) separating the glycan-hydrazone derivative or azoglycan dye by a separation method selected from the group consisting of high-performance liquid chromatography, open-column liquid chromatography, capillary electrophoresis and gel electrophoresis;
    (3) subjecting the glycan-hydrazone derivative or azoglycan dye to mass spectral analysis.

31. A method for the removal of O-glycans from a glycopeptide or glycoprotein having O-glycans comprising reacting the glycopeptide or glycoprotein with aqueous hydrazide hydrate in the presence of an additional base at an elevated temperature for a period sufficient to remove the O-glycans in the form of glycan hydrazones without releasing N-glycans from the glycopeptide or glycoprotein.

32. The method of claim 31 wherein the additional base is sodium hydroxide.

33. The method of claim 32 wherein the sodium hydroxide is used at a concentration of 0.1M.

34. The method of claim 31 wherein the additional base is triethylamine.

35. The method of claim 34 wherein the triethylamine is used at a concentration of 0.2M.

36. The method of claim 31 wherein the elevated temperature is about 45° C.

37. The method of claim 31 wherein the removed glycan hydrazones are further converted to heterocyclic pyrazole derivatives by treating the glycan hydrazones with a beta-dicarbonyl compound at room temperature.

38. The method of claim 37 wherein the beta-dicarbonyl compound is acetyl acetone.

39. The method of claim 31 wherein the removed glycan hydrazones are converted to reducing sugars.

40. The method of claim 39 wherein the conversion is by N-acetylating the removed glycan hydrazones with acetic anhydride and a mild base followed by treatment with acetone.

41. A method of immobilizing a reducing sugar onto a solid support having primary or secondary amine groups comprising converting the reducing sugar to a sugar hydrazone, converting the amine groups on the solid support to isothiocyanate groups and reacting the sugar hydrazone with the isothiocyanate-substituted support so as to cause the binding of the sugar to the support.

42. The method of claim 41 wherein the solid support is a chemically inert polymer support.

43. The method of claim 42 wherein the polymer support is a polystyrene support.

44. The method of claim 41 wherein the sugar hydrazone is produced by the method of claim 1.

45. The method of claim 41 wherein the reducing sugar is bound irreversibly to the solid support by heating the solid support at slightly acidic pH.

* * * * *